United States Patent
Stewart et al.

(10) Patent No.: US 11,788,064 B2
(45) Date of Patent: Oct. 17, 2023

(54) METHOD OF INCREASING PROLIFERATION OF PANCREATIC BETA CELLS, TREATMENT METHOD, AND COMPOSITION

(71) Applicant: ICAHN SCHOOL OF MEDICINE AT MOUNT SINAI, New York, NY (US)

(72) Inventors: Andrew F. Stewart, New York, NY (US); Courtney Ackeifi, New York, NY (US); Peng Wang, New York, NY (US); Bob Devita, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 16/959,390

(22) PCT Filed: Jan. 5, 2019

(86) PCT No.: PCT/US2019/012442
§ 371 (c)(1),
(2) Date: Jun. 30, 2020

(87) PCT Pub. No.: WO2019/136320
PCT Pub. Date: Jul. 11, 2019

(65) Prior Publication Data
US 2021/0032601 A1 Feb. 4, 2021

Related U.S. Application Data

(60) Provisional application No. 62/614,136, filed on Jan. 5, 2018.

(51) Int. Cl.
| | | |
|---|---|---|
| *C12N 5/00* | (2006.01) | |
| *C12N 5/071* | (2010.01) | |
| *A61P 5/48* | (2006.01) | |
| *A61P 3/10* | (2006.01) | |
| *A61K 31/437* | (2006.01) | |
| *A61K 38/22* | (2006.01) | |

(52) U.S. Cl.
CPC .......... *C12N 5/0676* (2013.01); *A61K 31/437* (2013.01); *A61K 38/22* (2013.01); *A61P 3/10* (2018.01); *A61P 5/48* (2018.01); *C12N 2501/335* (2013.01); *C12N 2501/727* (2013.01)

(58) Field of Classification Search
CPC .... C12N 5/0676; A61K 31/437; A61K 38/22; A61P 5/48
See application file for complete search history.

(56) References Cited

U.S. PATENT DOCUMENTS

| | | |
|---|---|---|
| 9,951,050 B2 | 4/2018 | Aberger et al. |
| 11,266,647 B2 | 3/2022 | Stewart et al. |
| 11,547,712 B2 | 1/2023 | Devita et al. |
| 2004/0116474 A1 | 6/2004 | Munchhof et al. |
| 2004/0192583 A1 | 9/2004 | Medicherla et al. |
| 2005/0032869 A1 | 2/2005 | Berta et al. |
| 2007/0060619 A1 | 3/2007 | Burns et al. |
| 2007/0208053 A1 | 9/2007 | Arnold et al. |
| 2008/0221171 A1 | 9/2008 | Eberle et al. |
| 2009/0196912 A1 | 8/2009 | Eickhoff et al. |
| 2009/0312322 A1 | 12/2009 | Berg et al. |
| 2010/0173931 A1 | 7/2010 | Ellies et al. |
| 2010/0184758 A1 | 7/2010 | Dobbelaar et al. |
| 2010/0197562 A1 | 8/2010 | De Lera Ruiz et al. |
| 2011/0053930 A1 | 3/2011 | Yu et al. |
| 2011/0123651 A1 | 5/2011 | Mower et al. |
| 2012/0071512 A1 | 3/2012 | Hu et al. |
| 2013/0023491 A1 | 1/2013 | Annes et al. |
| 2013/0102627 A1 | 4/2013 | Higgins et al. |
| 2013/0210060 A1 | 8/2013 | Hosoya et al. |
| 2014/0275064 A1 | 9/2014 | Leblond et al. |
| 2014/0288068 A1 | 9/2014 | Ellies et al. |
| 2015/0174034 A1 | 6/2015 | Hu et al. |
| 2015/0266878 A1 | 9/2015 | Yang et al. |
| 2015/0297573 A1 | 10/2015 | Dalle et al. |
| 2016/0038500 A1 | 2/2016 | Klein et al. |
| 2016/0039845 A1 | 2/2016 | Wang et al. |
| 2016/0122361 A1 | 5/2016 | Reddy et al. |
| 2016/0186143 A1 | 6/2016 | Melton et al. |
| 2016/0289315 A1 | 10/2016 | Mirza et al. |
| 2017/0056379 A1 | 3/2017 | Chen et al. |
| 2017/0280720 A1 | 10/2017 | Chesworth et al. |

(Continued)

FOREIGN PATENT DOCUMENTS

| | | |
|---|---|---|
| CN | 102977096 A | 3/2013 |
| CN | 105884767 A | 8/2016 |

(Continued)

OTHER PUBLICATIONS

International Search Report and Written Opinion for corresponding Application No. PCT/2019/012442 (dated Apr. 24, 2019).
Shah et al., "The DPP-4 Inhibitor Linagliptin Restores Beta-Cell Function and Survival in Human Isolated Islets through GLP-1 Stabilization," J. Clin. Endocrinol. Metabol. 98(7):1163-1172 (2013).
Navarro et al., "Genetic Disruption of Adenosine Kinase in Mouse Pancreatic Beta-Cells Protects Against High-Fat Diet-Induced Glucose Intolerance," Diabetes 66(7):1928-1938 (2017).
Office Action in Europe Application No. 17863636.1, dated Jan. 12, 2021.

(Continued)

*Primary Examiner* — Gyan Chandra
(74) *Attorney, Agent, or Firm* — Troutman Pepper Hamilton Sanders LLP (Rochester)

(57) ABSTRACT

Disclosed herein are methods of increasing cell proliferation in a population of pancreatic beta cells. Also disclosed are methods of treating a subject for a condition associated with insufficient insulin secretion. Also disclosed is a composition comprising a DYRK1A inhibitor and a GLP1R agonist. The disclosure further describes a method of regenerating pancreatic beta cells in a transplant patient.

13 Claims, 16 Drawing Sheets
Specification includes a Sequence Listing.

(56) References Cited

U.S. PATENT DOCUMENTS

| | | |
|---|---|---|
| 2017/0281607 A1 | 10/2017 | Davies |
| 2018/0216076 A1 | 8/2018 | Hebrok et al. |
| 2019/0328738 A1 | 10/2019 | Stewart et al. |
| 2020/0306257 A1 | 10/2020 | Devita et al. |
| 2021/0094950 A1 | 4/2021 | Kumar et al. |
| 2022/0064146 A1 | 3/2022 | Devita et al. |
| 2022/0162182 A1 | 5/2022 | Devita et al. |

FOREIGN PATENT DOCUMENTS

| | | |
|---|---|---|
| GB | 2447791 A | 9/2008 |
| WO | 2010/123583 A2 | 10/2010 |
| WO | 2010/137350 A1 | 12/2010 |
| WO | 2011/075665 A2 | 6/2011 |
| WO | 2011/133795 A2 | 10/2011 |
| WO | 2011/133882 A1 | 10/2011 |
| WO | 2011/133888 A1 | 10/2011 |
| WO | 2011/138421 A1 | 11/2011 |
| WO | 2011/161256 A1 | 12/2011 |
| WO | 2012/024433 A2 | 2/2012 |
| WO | 2013/119518 A1 | 8/2013 |
| WO | 2014/004857 A1 | 1/2014 |
| WO | 2014/058080 A1 | 4/2014 |
| WO | 2014/063477 A1 | 5/2014 |
| WO | 2014/153203 A2 | 9/2014 |
| WO | 2014/202638 A1 | 12/2014 |
| WO | 2014/203217 A1 | 12/2014 |
| WO | 2015/011331 A1 | 1/2015 |
| WO | 2015/058031 A1 | 4/2015 |
| WO | 2015/157093 A1 | 10/2015 |
| WO | 2016/064676 A1 | 4/2016 |
| WO | 2016/161410 A2 | 10/2016 |
| WO | 2017040993 A1 | 3/2017 |
| WO | 2017/085198 A1 | 5/2017 |
| WO | 2017/106630 A1 | 6/2017 |
| WO | 2017/117556 A1 | 7/2017 |
| WO | 2017/168245 A1 | 10/2017 |
| WO | 2017/197151 A1 | 11/2017 |
| WO | 2018/081401 A1 | 5/2018 |
| WO | 2018/083157 A1 | 5/2018 |
| WO | 2018/098561 A1 | 6/2018 |
| WO | 2018/210994 A1 | 11/2018 |
| WO | 2019/100062 A1 | 5/2019 |
| WO | 2019/183245 A1 | 9/2019 |
| WO | 2020/142485 A1 | 7/2020 |
| WO | 2020/142486 A1 | 7/2020 |

OTHER PUBLICATIONS

Wang et al., "Diabetes Mellitus—Advances and Challenges in Human β-Cell Proliferation," Nat. Rev. Endocrinol. 11:201-212 (2015).
EP Search Report and Opinion for EP Application No. 178636361.1, dated May 6, 2020.
Shen et al., "Inhibition of DYRK1A and GSK3B induces human β-Cell Proliferation," Nature Comm. 6:8372 (2015).
Madhu et al., "Dual Inhibition of Activin/Nodal/TGF-β and BMP Signaling Pathways by SB431542 and Dorsomorphin Induces Neuronal Differentiation of Human Adipose Derived Stem Cells," Stem Cells Int. 1-13 (2016).
Vogt et al., "The Specificities of Small Molecule Inhibitors of the TGFβ and BMP Pathways," Cell. Signal. 23 (11):1831-1842 (2011).
Wang et al., "Combined Inhibition of DYRK1A, SMAD, and Trithorax Pathways Synergizes to Induce Robust Replication in Adult Human Beta Cells," Cell Metab. 29(3):638-652 (2019).
Nassar et al. "A TGF-Beta Receptor 1 Inhibitor for Prevention of Proliferative Vitreoretinopathy," Experimental Eye Research, 2014, vol. 123, pp. 72-86 (Year: 2014).
Wang et al., "A High-throughput Chemical Screen Reveals That Harmine-mediated Inhibition of DYRK1A Increases Human Pancreatic Bela Cell Replication," Nature Medicine 21(4):383-388 (2015).
Huynh et al., "Screening and Identification of a Novel Class of TGF-[beta] Type 1 Receptor Kinase Inhibitor," Journal of Biomolecular Screening 16(7):724-733 (2011).
Dhawan et al., "Inhibition of TGF-beta Signaling Promotes Human Pancreatic Bela Cell Replication," Diabetes 65 (5):1208-1218 (2016).
Pagliuca et al., "Generation of Functional Human Pancreatic [beta] Cells In Vitro," Cell 159(2):428-439 (2014).
PCT International Search Report and Opinion for International Application No. PCT/US2017/058498, dated Jan. 9, 2018.
Xiao et al., "Resveratrol Attenuates Renal Injury and Fibrosis by Inhibiting Transforming Growth Factor β Pathway on Matrix Metalloproteinase 7," Experimental Biology and Medicine, Jan. 2016, vol. 241, pp. 140-146. (Year: 2016).
Office Action in Europe Application No. 17863636.1, dated Oct. 22, 2021.
Restriction Requirement in U.S. Appl. No. 16/344,230 (dated Feb. 6, 2020).
Office Action in U.S. Appl. No. 16/344,230 (dated May 4, 2020).
Office Action in U.S. Appl. No. 16/344,230 (dated Nov. 2, 2020).
Office Action in U.S. Appl. No. 16/344,230 (dated Apr. 13, 2021).
International Search Report and Written Opinion for International Application No. PCT/US2018/062023 (dated Feb. 4, 2019).
Chunduru et al., "One-Pot Synthesis of 1,3.4-Tliiadiazin-5-yl-chromen-2-one Derivatives via Three-Component Reaction," Synthetic Communications 42:1454-1460 (2012).
Kumar et al., "Novel Selective Thiadiazine DYRK1A inhibitor Lead Scaffold with Human Pancreatic B-Cell Proliferation Activity," European Journal of Medicinal Chemistry 157:1005-1016 (2018).
PubmedCompound Summary for CID 17565749, "PNJQHHXWPZEHTA-UHFFFAOYSA-N," U.S. National Library of Medicine, pp. 1-10 (2007).
Extended European Search Report in EPO Application No. 18878625.5 (dated Feb. 23, 2021).
Restriction Requirement in U.S. Appl. No. 16/765,542 (dated Nov. 27, 2020).
Office Action in U.S. Appl. No. 16/765,542 (dated Feb. 18, 2021).
Office Action in U.S. Appl. No. 16/765,542 (dated May 24, 2021).
Office Action in U.S. Appl. No. 16/765,542 (dated Nov. 8, 2021).
Supplementary European Search Report and Written Opinion in EP 19735846.8 (dated Aug. 18, 2021).
Kumar et al., "Development of Kinase-Selective, Harmine-Based DYRK1A Inhibitors that Induce Pancreatic Human β-Cell Proliferation," J. Med. Chem. 61(17):7687-7699 (2018) [Author Manuscript].
Amisten et al., "An Atlas and Functional Analysis of G-Protein Coupled Receptors in Human Islets of Langerhans," Pharmacology & Therapeutics 139:359-391 (2013).
Zhao et al., "Repurposing cAMP-Modulating Medications to Promote β-Cell Replication," Mol. Endocrinol. 28 (10):1682-1697 (2014).
Reimann & Gribble, "G Protein-Coupled Receptors as New Therapeutic Targets for Type 2 Diabetes," Diabetologica 59:229-233 (2016).
Bachem, "Peptides for Diabetes Research," Peptides and Diabetes, published by Global Marketing Bachem Group (2017).
Nance et al., "Discovery of a Novel Series of Orally Bioavailable and CNS Penetrant Glucagon-Like Peptide-1 Receptor (GLP-1R) Noncompetitive Antagonists Based on a 1,3-Disubstituted-7-Aryl-5,5-Bis(Trifluoromethyl)-5,8-Dihydropyrimido[4,5-d]Pyrimidine-2,4(1H,3H)-Dione Core," J. Med. Chem. 60:1611-1616 (2017).
International Search Report and Written Opinion for International Application No. PCT/US2019/023206, dated Jul. 29, 2019.
Ishida et al., "Antitumor Agents 201. Cytotoxicity and B-Carboline Analogs," Bioorg. Med. Chem. Lett. 9:3319-3324 (1999).
International Search Report and Written Opinion for International Application No. PCT/US2019/069057 (dated Mar. 9, 2020).
Multhoff et al., "Chronic Inflammation in Cancer Development," Front. Immunol. 2(98):1-17 (2012).
International Search Report and Written Opinion for International Application No. PCT/US2019/069059, dated Mar. 9, 2020.
Dirice, E., et al., "Inhibition of DYRK1A Stimulates Human beta-Cell Proliferation," Diabetes, 65:1660-1671 (2016).
Pubchem CID 53496098, pp. 1-9 (2011).

(56) References Cited

OTHER PUBLICATIONS

Pubchem CID 116977135, pp. 1-7 (2016).
Pubchem CID 84152473, pp. 1-7 (2104).
Pubchem CID 66793828, pp. 1-9 (2012).
Pubchem CID 20199687, pp. 1-9 (2007).
Pubchem CID 68046670, pp. 1-8 (2012).
Pubchem CID 76281619, pp. 1-10 (2014).
Tahtouh et al., "Selectivity, Cocrystal Structures, and Neuroprotective Properties of Leucettines, a Family of Protein Kinase Inhibitors Derived from the Marine Sponge Alkaloid Leucettamine B," J. Med. Chem. 55:9312-9330 (2012).
Office Action in U.S. Appl. No. 16/765,542 (dated Apr. 8, 2022).
Supplementary Partial European Search Report and Opinion in EP Application No. 19771612.9, dated Dec. 20, 2021.
Balint et al., "Structure-Based Design and Synthesis of Harmine Derivatives with Different Selectivity Profiles in Kinase versus Monoamine Oxidase Inhibition," ChemMedChem. 12(12):932-939 (2017).
Drung et al., "Computational & Experimental Evaluation of the Structure/Activity Relationship of β-Carbolines as DYRK1A Inhibitors," Bioorg. Med. Chem. Lett. 24(20):4854-4860 (2014).
Yadav and Nandi, "QSAR and Anticancer Drug Design of β-Carboline Compounds Utilizing Computed Molecular Descriptors," Journal of Computational Methods in Molecular Design 4(3):92-105 (2014).
Frederick et al., "Novel Trisubstituted Harmine Derivatives with Original in Vitro Anticancer Activity," J. Med. Chem. 55(14):6489-6501 (2012).
Cuny et al., "Structure-Activity Relationship Study of Beta-Carboline Derivatives as Haspin Kinase Inhibitors," Bioorg. Med. Chem. Lett. 22(5):2015-2019 (2012) [Author Manuscript].
Filali et al., "Synthesis of New Harmine Isoxazoles and Evaluation of their Potential Anti-Alzheimer, Anti-inflammatory, and Anticancer Activities," Med. Chem. 12(2):184-190 (2016).
Filali et al., "Synthesis of New Isoxazoline Derivatives from Harmine and Evaluation of their Anti-Alzheimer, Anti-Cancer and Antiinflammatory Activities," 30(3):371-376 (2015).
European Search Report and Opinion in EP Application No. 19771612.9, dated Mar. 22, 2022.
International Search Report and Written Opinion International Application No. PCT/US21/39132 (dated Dec. 7, 2021).
Gupta et al., "Models for the Prediction of Receptor Tyrosine Kinase Activity of Substituted 3-Aminoindazole Analogues," Sci. Pharm. 79:239-257 (2011).
Pubchem SID 194152017, pp. 1-7 (2014).
Pubchem SID 245038163, pp. 1-7 (2015).
Bresson et al., "Anti-CD3 and Nasal Proinsulin Combination Therapy Enhances Remission from Recent-Onset Autoimmune Diabetes by Inducing Tregs," J. Clin. Invest. 116(5):1371-1381 (2006).
Herold et al., "An Anti-CD3 Antibody, Teplizumab, in Relatives at Risk for Type 1 Diabetes," N. Engl. J. Med. 381:603-613 (2019).
Sims et al., "Teplizumab Improves and Stabilizes Beta Cell Function in Antibody Positive High-Risk Individuals," Sci. Transl. Med. 13(583):eabc8980 (2021) [Author Manuscript].
Heagopian et al., "Teplizumab Preserves C-Peptide in Recent-Onset Type 1 Diabetes: Two-Year Results from the Randomized, Placebo-Controlled Protégé Trial," Diabetes 62(11):3901-3908 (2013).
Herold et al., "Teplizumab (Anti-CD3 mAb) Treatment Preserves C-Peptide Responses in Patients With New-Onset Type 1 Diabetes in a Randomized Control Trial: Metabolic and Immunologic Features at Baseline Identify a Subgroup of Responders," Diabetes 62(11):3766-3774 (2013).
Sherry et al., "Teplizumab for Treatment of Type 1 Diabetes (Protégé Study): 1 Year Results from a Randomised, Placebo-Controlled Trial," Lancet 378:487-497 (2011).
Bluestone et al., "Immunotherapy: Building a Bridge to a Cure for Type 1 Diabetes," Science 373:510-516 (2021).
von Herrath et al., "Anti-Interleukin-21 Antibody and Liraglutide for the Preservation of β-Cell Function in Adults with Recent-Onset Type 1 Diabetes: A Randomised, Double-Blind, Placebo-Controlled, Phase 2 Trial," Lancet Diabetes Endocrinol. 9:212-224 (2021).
Rosselot et al., "Human Beta Cell Mass Expansion in Vivo with a Harmine and Extendin-4 Combination: Quantification and Visualization by iDISCO+ 3D Imaging," bioRxiv preprint (2021).
European Search Report and Opinion in EP Application No. 19907897.3, dated Sep. 12, 2022.
Gupta et al., "Synthesis of 4-Aryl and Unsymmetrical 4,6-Diarylpyrimidines by the Suzuki-Miyaura Cross-Coupling Reaction," Heterocycles 96(9):1549-1569 (2018).
Coombs et al., "Small-Molecule Pyrimidine Inhibitors of the CDC2-Like (Clk) and Dual Specificity Tyrosine Phosphorylation-Regulated (Dyrk) Kinases: Development of Chemical Probe ML315," Bioorganic & Medicinal Chemistry Letters 23(12):3654-3661 (2013) [Author Manuscript].
European Search Report and Opinion in EP Application No. 19907044.2, dated Aug. 5, 2022.
Pu et al., "Design, Synthesis and Biological Evaluation of Indole Derivatives as Vif Inhibitors," Bioorganic & Medicinal Chemistry Letters 27(17):4150-4155 (2017).
Willard et al., "Tirzepatide is an Imbalanced and Biased Dual GIP and GLP-1 Receptor Agonist," JCI Insight 5(17):e140532 (2020).
Wang et al., "Induction of Human Pancreatic Beta Cell Replication by Inhibitors of Dual Specificity Tyrosine Regulated Kinase," Nat. Med. 21(4):383-388 (2015).
Annes et al., "Adenosine Kinase Inhibition Selectively Promotes Rodent and Porcine Islet β-cell Replication," PNAS 109:3915-3920 (2012).
Abdolazimi et al., "CC-401 Promotes β-Cell Replication via Pleiotropic Consequences of DYRK1A/B Inhibition," Endocrinology 159(9):3143-3157 (2018).
Screenshot of the MedChem Express webpage identifying CC-401 by structure and as CAS No. 395104-30-0.
Parnaud et al., "Proliferation of Sorted Human and Rat Beta Cells," 51(1):91-100 (2008).
Dai et al., "Age-Dependent Human Beta Cell Proliferation Induced by Glucagon-Like Peptide-1 and Calcineurin Signaling," J. Clin. Invest. 127(10):3835-3844 (2017).
Examination Report in EP Application No. 17863636.1, dated Aug. 11, 2022.
Coskun et al., "LY3298176, A Novel Dual GIP and GLP-1 Receptor Agonist for the Treatment of Type 2 Diabetes Mellitus: From Discovery to Clinical Proof of Concept," Mol. Metab. 18:3-14 (2018).
Office Action and Search Report in JP 2020-527899 (dated Oct. 18, 2022).
"5-(2-Benzylimino-3,6-dihydro-1,3,4-thiadiazin-5-yl)-1,3-dihydrobenzimidazol-2-one," Web page <https://pubchem.ncbi.nlm.nih.gov/compound/135783279>, 11 pages, Jan. 17, 2019, retrieved from <https://pubchem.ncbi.nlm.nih.gov/compound/135783279> on Oct. 24, 2022.
Office Action and Search Report in CN 201980017277.6 (dated Oct. 25, 2022).
Office Action and Search Report in JP 2020-537237 (dated Dec. 26, 2022).
Office Action and Search Report in JP 2020-550798 (dated Feb. 9, 2023).
Examination Report in EP Application No. 19771612.9, dated May 12, 2023.
First Office Action for CN201980032475.X, dated Mar. 19, 2023.
Examination Report for EP19907044.2, dated May 10, 2023.
First Office Action for CN201980093305.2, dated Mar. 22, 2023.
STN Search Results, CN Office Action for 201980093305.2 (dated Mar. 22, 2023).
Decision of Rejection in Japan Application No. JP 2020-537237 (dated Jul. 27, 2023).

*p<0.02
** p<0.001

* p<0.05
** p<0.005

METHOD OF INCREASING PROLIFERATION OF PANCREATIC BETA CELLS, TREATMENT METHOD, AND COMPOSITION

This application is a national stage application under 35 U.S.C. § 371 of PCT Application No. PCT/US2019/012442, filed Jan. 5, 2019, which claims the priority benefit of U.S. Provisional Patent Application Ser. No. 62/614,136, filed Jan. 5, 2018, which is hereby incorporated by reference in its entirety.

This invention was made with government support under T32 GM062754, DK105015, DK105015-01A1S1, P30 DK 020541, and UC4 DK 104211 awarded by National Institutes of Health. The government has certain rights in the invention.

FIELD

Described are methods of increasing cell proliferation in a population of pancreatic beta cells, methods of treating a subject for a condition associated with insufficient insulin secretion, and compositions comprising a dual-specificity tyrosine phosphorylation-regulated kinase 1A inhibitor and a glucagon-like peptide-1 receptor agonist.

BACKGROUND

Diabetes affects 422 million people globally, is increasing in prevalence (World Health Organization Global Report on Diabetes, 2016), and ultimately results from inadequate numbers of functional, insulin-producing beta cells (Butler et al., "Beta Cell Deficit and Increased Beta Cell Apoptosis in Humans with Diabetes," *Diabetes* 52(1):102-110 (2003) and Campbell-Thompson et al., "Insulitis and Beta Cell Mass in the Natural History of Type 1 Diabetes," *Diabetes* 65(3):719-731 (2016)).

Both Type 1 and Type 2 diabetes ultimately result from inadequate numbers of functional, insulin-secreting pancreatic beta cells. Replacing or regenerating human beta cell mass and function, therefore, are principal goals of diabetes research. Unfortunately, inducing adult human beta cells to replicate has proven to be challenging: After early childhood, human beta cells fail to replicate at therapeutically relevant rates, and they have proven recalcitrant to efforts to induce their expansion in response to drugs, growth factors, nutrients, or other approaches (Gregg et al., "Formation of a Human Beta Cell Population within Pancreatic Islets is Set Early in Life," *J. Clin. Endocrinol Metab.* 97(9):3197-3206 (2012) and Wang et al., "Advances and Challenges in Human Beta Cell Proliferation for Diabetes," *Nat. Rev. Endocrinol.* 11(4):201-212 (2015)).

Drugs that act directly or indirectly to activate the glucagon-like peptide-1 receptor ("GLP1R") are among the current most widely prescribed diabetes drugs in the world. The GLP1R agonist family includes GLP1(7-36) itself, the more stable reptilian homologue, exenatide, as well as modified exenatide analogues such as liraglutide, lixisenatide, semaglutide, and others (Drucker D J, "Mechanisms of Action and Therapeutic Application of Glucagon-Like Peptide-1," *Cell Metab.* 27(4):740-756 (2018) and Guo X-H, "The Value of Short- and Long-Acting Glucagon-Like Peptide Agonists in the Management of Type 2 Diabetes Mellitus: Experience with Exenatide," *Curr. Med. Res. Opin.* 32(1):1, 67-76 (2016)). These GLP1R agonists, and additional agents that prevent degradation of endogenous GLP1 by the enzyme dipeptidylpeptidase IV ("DPP4") (exemplified by sitagliptin, vildagliptin, saxagliptin, and others (Drucker D J, "Mechanisms of Action and Therapeutic Application of Glucagon-Like Peptide-1," *Cell Metab.* 27(4):740-756 (2018) and Deacon et al., "Dipeptidyl Peptidase-4 Inhibitors for the Treatment of Type 2 Diabetes: Comparison, Efficacy and Safety," *Expert Opin. Pharmacother.* 14(15):2047-2058 (2013)) induce proliferation in rodent beta cells, but have repeatedly failed to activate beta cell replication in adult human islets (Parnaud et al., "Proliferation of Sorted Human and Rat Beta Cells," *Diabetologia* 51(1):91-100 (2008) and Dai et al., "Age-Dependent Human Beta Cell Proliferation Induced by Glucagon-Like Peptide-1 and Calcineurin Signaling," *J. Clin. Invest.* 127(10):3835-3844 (2017)). However, they have a beneficial "incretin" effect, inducing beta cells to accentuate insulin secretion when blood glucose is elevated (Drucker D J, "Mechanisms of Action and Therapeutic Application of Glucagon-Like Peptide-1," *Cell Metab.* 27(4):740-756 (2018)). In the current context, although GLP1R agonists fail to induce human beta cell proliferation, the GLP1R has a limited tissue distribution and is particularly highly expressed in the beta cell (Drucker D J, "Mechanisms of Action and Therapeutic Application of Glucagon-Like Peptide-1," *Cell Metab.* 27(4):740-756 (2018); Pyke et al., "GLP1 Receptor Localization in Monkey and Human Tissue: Novel Distribution Revealed With Extensively Validated Monoclonal Antibody," *Endocrinology* 155(4):1280-90 (2014); and Amisten et al., "An Atlas and Functional Analysis of G-Protein Coupled Receptors in Human Islets of Langerhans," *Pharmacol. Ther.* 139(3):359-391 (2013)). It thus provides a currently unique degree of beta cell specificity.

Dual-specificity Tyrosine-Regulated Kinase 1A ("DYRK1A") is a downstream component of a signaling cascade that is able to induce human and rodent beta cell proliferation according to the following scenario (Wang et al., "A High-Throughput Chemical Screen Reveals that Harmine-Mediated Inhibition of DYRK1A Increases Human Pancreatic Beta Cell Replication," *Nat. Med.* 21(4): 383-388 (2015); Gallo et al., "Lymphocyte Calcium Signaling from Membrane to Nucleus," *Nat. Immunol.* 7(1):25-32 (2006); Heit et al., "Calcineurin/NFAT Signaling Regulates Pancreatic β-cell Growth and Function," *Nature* 443(7109): 345-349 (2006); and Goodyer et al., "Neonatal Beta Cell Development in Mice and Humans is Regulated by Calcineurin/NFaT," *Dev. Cell* 23:21-34 (2012)). Increases in intracellular calcium (induced, e.g., by glucose, drugs, etc.) lead to sequential activation of calmodulin and calcineurin, the latter of which dephosphorylates the cytoplasmic pool of transcription factors named Nuclear Factors in activated T-cells ("NFaTs"). This permits the NFaTs to translocate to the nucleus where they transactivate cell cycle activator genes and repress cell cycle inhibitor genes, resulting in beta cell proliferation. The nuclear kinase DYRK1A acts as a "brake" on this process, re-phosphorylating nuclear NFaTs, forcing them to exit the nucleus, thereby terminating their mitogenic signal. The harmine analogue family ("harmalogs") inhibits DYRK1A, removing the "brakes" on proliferation in beta cells, thereby permitting cell cycle entry.

The DYRK1A inhibitor class of drugs include harmine (Wang et al., "A High-Throughput Chemical Screen Reveals that Harmine-Mediated Inhibition of DYRK1A Increases Human Pancreatic Beta Cell Replication," *Nat. Med.* 21(4): 383-388 (2015)), INDY (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015)), leucettine (Tahtouh et al., "Selectivity, Co-Crystal Structures and Neuroprotective Properties of Leucettines, a Family of Protein Kinase Inhibitors Derived from the Marine Sponge Alkaloid Leucettamine B," *J. Med. Chem.* 55(21):9312-9330 (2012), GNF4877 (Shen et al., "Inhibition of DYRK1A and GSK3B Induces Human Beta Cell Proliferation," *Nat. Commun.* 6:8372 (2015)), 5-iodotubericidin ("5-IT") (Dirice et al., "Inhibition of DYRK1A Stimulates Human Beta Cell Proliferation," *Diabetes* 65(6):1660-1671 (2016)); CC-401 (Abdolazimi et al., "CC-401 Promotes Beta Cell Replication via Pleiotropic Consequences of DYRK1A/B Inhibition," *Endocrinology* 159(9):3143-3157 (2018)), and others (Wang et al., "A High-Throughput Chemical Screen Reveals that Harmine-Mediated Inhibition of DYRK1A Increases Human Pancreatic Beta Cell Replication," *Nat. Med.* 21(4): 383-388 (2015); Shen et al., "Inhibition of DYRK1A and GSK3B Induces Human Beta Cell Proliferation," *Nat. Commun.* 6:8372 (2015); Dirice et al., "Inhibition of DYRK1A Stimulates Human Beta Cell Proliferation," *Diabetes* 65(6): 1660-1671 (2016); Abdolazimi et al., "CC-401 Promotes Beta Cell Replication via Pleiotropic Consequences of DYRK1A/B Inhibition," *Endocrinology* 159(9):3143-3157 (2018); Aamodt et al., "Development of a Reliable Automated Screening System to Identify Small Molecules and Biologics that Promote Human Beta Cell Regeneration," *AJP Endo. Metab.* 311:E859-68 (2016); and Wang et al., "Single Cell Mass Cytometry Analysis of Human Endocrine Pancreas," *Cell Metab.* 24(4):616-626 (2016)). These drugs induce proliferation in human beta cells via their ability to induce nuclear translocation of nuclear factor of activated T-cells ("NFaTs"), transcription factors that then transactivate cell cycle-activating genes and repress cell cycle inhibitor genes (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human Beta Cell Proliferation," *Nat. Commun.* 6:8372 (2015); and Dirice et al., "Inhibition of DYRK1A Stimulates Human Beta Cell Proliferation," Diabetes 65(6):1660-1671 (2016)).

While the mitogenic capability of the harmalog family is encouraging, two difficulties remain. First the rates of proliferation observed in response to the harmine family, assessed by Ki67 or BrdU/EdU beta cell labeling indices is in the 1-3%/day range (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human Beta Cell Proliferation," *Nat. Commun.* 6:8372 (2015); Dirice et al., "Inhibition of DYRK1A Stimulates Human Beta Cell Proliferation," *Diabetes* 65(6):1660-1671 (2016); Aamodt et al., "Development of a Reliable Automated Screening System to Identify Small Molecules and Biologics That Promote Human Beta Cell Regeneration," *AJP Endo. Metab.* 311: E859-68 (2016); and Wang et al., "Singe Cell Mass Cytometry Analysis of Human Endocrine Pancreas," *Cell Metab.* 24(4):616-626 (2016)). While this mimics the physiological rates of proliferation described in normal juvenile pancreata in the first year of life (Gregg et al., "Formation of a Human Beta Cell Population within Pancreatic Islets is Set Early in Life," *J. Clin. Endocrinol Metab.* 97(9):3197-3206 (2012) and Wang et al., "Advances and Challenges in Human Beta Cell Proliferation for Diabetes," *Nat. Rev. Endocrinol.* 11(4): 201-212 (2015)), this rate is unlikely to lead to rapid repletion of beta cell mass in people with Type 1 diabetes whose beta cell mass is reduced by 80-99% (Meier et al., "Sustained Beta Cell Apoptosis in Patients with Longstanding Type 1 *Diabetes: Indirect* Evidence for Islet Regeneration?," *Diabetologia* 48:2221-2228 (2005) and Keenan et al., "Residual Insulin Production and Beta Cell Turnover after 50 Years of Diabetes: Joslin Medalist Study," *Diabetes* 59:2853 (2010)). Thus, higher rates of proliferation are desirable. Second, the biologic effects of the harmine family are not limited to proliferation in beta cells: This class of drugs leads to proliferation in other islet cell types (alpha cells, etc.) (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015); Dirice et al., "Inhibition of DYRK1A Stimulates Human Beta Cell Proliferation," *Diabetes* 65(6):1660-1671 (2016); and Wang et al., "Single Cell Mass Cytometry Analysis of Human Endocrine Pancreas," *Cell Metab.* 24(4):616-626 (2016)) and, since the calcium-calmodulin-calcineurin-NFaT pathway is ubiquitous, presumably other cell types as well. Further, harmine is a CNS-active drug with well-known psychoactive and hallucinogenic properties (Brierley et al., "Developments in Harmine Pharmacology—Implications for Ayahuasca Use and Drug Dependence Treatment," *Prog. Neuro-Psychopharmacol Biol. Psych.* 39:263-272 (2012) and Heise et al., "Ayahuasca Exposure: Descriptive Analysis of Call to US Poison Control Centers from 2005-2015," *J. Med. Toxicol.* 13:245-8 (2017)). Thus, there is a need to identify methods to target or confine the mitogenic activity of the harmine class to the human beta cell, limiting off-target adverse effects.

Whether combination therapy using a GLP1R agonist could further enhance the mitogenic efficacy of the harmine class of drugs has not been investigated.

The disclosure provided herein is directed to overcoming deficiencies in the art.

SUMMARY

One aspect of the disclosure relates to a method of increasing cell proliferation in a population of pancreatic beta cells. This method involves contacting a population of pancreatic beta cells with a dual-specificity tyrosine phosphorylation-regulated kinase 1A (DYRK1A) inhibitor and a glucagon-like peptide-1 receptor (GLP1R) agonist, where said contacting is carried out under conditions effective to cause a synergistic increase in cell proliferation in the population of pancreatic beta cells.

Another aspect of the disclosure relates to a method of treating a subject for a condition associated with insufficient insulin secretion. This method involves administering to a subject in need of treatment for a condition associated with an insufficient level of insulin secretion a dual-specificity tyrosine phosphorylation-regulated kinase 1A (DYRK1A) inhibitor and a glucagon-like peptide-1 receptor (GLP1R) agonist, where the administering is carried out under conditions effective to cause a synergistic increase in pancreatic beta cell mass in the subject to treat the subject for an insufficient level of insulin secretion.

A further aspect of the disclosure relates to a composition comprising a dual-specificity tyrosine phosphorylation-regulated kinase 1A (DYRK1A) inhibitor and a glucagon-like peptide-1 receptor (GLP1R) agonist.

Yet another aspect of the disclosure relates to a method of regenerating pancreatic beta cells in a transplant patient. This method involves administering to a transplant patient a dual-specificity tyrosine phosphorylation-regulated kinase 1A (DYRK1A) inhibitor and a glucagon-like peptide-1 receptor (GLP1R) agonist, wherein said administering is carried out under conditions effective to cause a synergistic increase in pancreatic beta cell mass in the transplant patient to regenerate pancreatic beta cells in the patient.

Another aspect of the disclosure relates to a method of treating a subject for a condition associated with insufficient insulin secretion. This method involves administering to a subject in need of treatment for a condition associated with an insufficient level of insulin secretion a dual-specificity tyrosine phosphorylation-regulated kinase 1A (DYRK1A) inhibitor and a dipeptidylpeptidase IV (DPP4) inhibitor, where the administering is carried out under conditions effective to cause a synergistic increase in pancreatic beta cell mass in the subject to treat the subject for an insufficient level of insulin secretion.

GLP1R agonists and DPP4 inhibitors are among the most widely prescribed Type 2 diabetes drugs. Although they increase insulin secretion from beta cells (Reimann et al., "G Protein-Coupled Receptors as New Therapeutic Targets for Type 2 Diabetes," *Diabetologia* 59(2):229-233 (2016), which is hereby incorporated by reference in its entirety), they fail to increase human beta cell proliferation (Drucker D J, "Mechanisms of Action and Therapeutic Application of Glucagon-Like Peptide-1," *Cell Metab.* 27(4):740-756 (2018); Parnaud et al., "Proliferation of Sorted Human and Rat Beta Cells," *Diabetologia* 51(1):91-100 (2008); and Dai et al., "Age-Dependent Human Beta Cell Proliferation Induced by Glucagon-Like Peptide-1 and Calcineurin Signaling," *J. Clin. Invest.* 127(10):3835-3844 (2017), which are hereby incorporated by reference in their entirety). Small molecule inhibitors of DYRK1A represent the first class of drugs that are able to induce adult human beta cell proliferation, but the rates are modest (~2%/day) (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human Beta Cell Proliferation," *Nat. Commun.* 6:8372 (2015); Dirice et al., "Inhibition of DYRK1A Stimulates Human Beta Cell Proliferation," *Diabetes* 65(6):1660-1671 (2016); Abdolazimi et al., "CC-401 Promotes Beta Cell Replication via Pleiotropic Consequences of DYRK1A/B Inhibition," *Endocrinology* 159(9):3143-3157 (2018); Aamodt et al., "Development of a Reliable Automated Screening System to Identify Small Molecules and Biologics that Promote Human Beta Cell Regeneration," *AJP Endo. Metab.* 311:E859-68 (2016); and Wang et al., "Single Cell Mass Cytometry Analysis of Human Endocrine Pancreas," *Cell Metab.* 24(4):616-626 (2016), which are hereby incorporated by reference in their entirety).

Described infra is the demonstration that combining any GLP1R agonist with any DYRK1A inhibitor surprisingly induces synergistic rates (5-6%/day) of human beta cell replication as well as increases in actual numbers of human beta cells. The synergy requires combined inhibition of DYRK1A and increases in cAMP. Treatment does not lead to beta cell de-differentiation, and provides a degree of human beta cell specificity not previously achieved. These beneficial effects extend from normal human beta cells to those derived from people with Type 2 diabetes. This disclosure demonstrates that these effects apply not only to normal human beta cells, but also to beta cells from humans with Type 2 diabetes.

As surprisingly disclosed herein, by combining any one of a large group of currently widely used diabetes drugs that directly (the GLP1 analogues) or indirectly (the DPP4 inhibitors) activate the GLP1R to an orally active, small molecule DYRK1A inhibitor (such as harmine, INDY, leucettine, 5-IT, GNF4877, or others), one is able to induce "rates" or "labeling indices" of human beta cell replication. These rates exceed those of DYRK1A inhibitors alone, and are in the range one might envision as being necessary for restoration of normal beta cell mass in people with Type 2 diabetes and perhaps Type 1 diabetes. The increase in human beta cell proliferation markers is accompanied by actual increases in numbers of adult human beta cells. The increase in proliferation is synergistic in a rigorous pharmacological sense, and even extends to doses of harmine and GLP1 that have no proliferative effect on their own.

BRIEF DESCRIPTION OF THE DRAWINGS

FIG. 1A is a graph showing the effects of the indicated drug treatments on dispersed human islet cells treated for 96 hours, and immunolabeled for Ki67 and insulin. "DMSO" indicates control vehicle, at 0.1%. The bars indicate mean±SEM, and the numbers within the bars indicate the number of human islet preparations studied at each dose. A minimum of 1000 beta cells was counted for each bar. * indicates ** $p<0.05$ and indicates $p<0.001$ vs. harmine alone. FIG. 1B shows examples of Ki67 and insulin immunolabeling used in FIG. 1A. FIG. 1C is a graph showing a negative control which demonstrates the quantitation of FACS-quantified human beta cells in response to progressive lowering of the numbers of human islets. FIG. 1D is a graph showing a second negative control which demonstrates a reduction in human beta cell numbers in response to treatment with cytokines (1000 IU/ml each TNFα, IL1β and IFNγ). FIG. 1E is a graph showing an increase in human beta cell numbers within 96 hours of treatment in seven of eight human islet preparations treated with vehicle (0.1% DMSO) or the combination of harmine (10 μM) and GLP1 (5 nM). In FIGS. 1C-1E, * indicates $p<0.0.05$, $p<0.001$, and *$p<0.02$. FIG. 1F is a graph showing the results of the treatment of dispersed human islets with a variety of DYRK1A inhibitors with or without GLP1, as indicated. The bars indicate mean±SEM, and the numbers within the bars indicate the number of human islet preparations studied at each dose. A minimum of 1000 beta cells was counted for each bar. In FIGS. 1F-1G, # indicates $p<0.025$ and ** indicates $p<0.01$ vs. DYRK1A inhibitor alone. Note that proliferation with each DYRK1A inhibitor was normalized to a value of 1, and the GLP1 combination is expressed as a function of the DYRK1A inhibitor proliferative effects, as detailed in FIG. 4. The actual Ki67% values were: Harmine, 2.1%, INDY 1.7%, leucettine 2.8%, 5-IT 2.6%, and GNF4788 2.9%. These values approximately doubled when GLP1 5 nM was administered. FIG. 1G is a graph showing the results of treatment of dispersed human islets with harmine with or without the GLP1R agonists as indicated. Data are expressed as in FIG. 1F; the actual Ki67% value for harmine was 2.2%, so that raw Ki67 values from each GLP1R agonist were approximately double the harmine value. The bars indicate mean±SEM, and the numbers within the bars indicate the number of human islet preparations studied at each dose. A minimum of 1000 beta cells was counted for each bar. * indicates $p<0.05$ and ** indicates $p<0.03$ vs. harmine alone.

FIG. 3A is a graph showing the results of the same experiments as shown in FIG. 1A and FIG. 2, adjusted such that percent of Ki67$^+$/insulin$^+$ cells/total insulin$^+$ immunolabeled cells are all normalized to the values in the harmine group, which is defined as "1". Since not every human islet preparation can be assayed at every dose of every drug, this permits adjustment of each dataset to all experiments performed in the same human islet donor. This adjustment is used for each subsequent panel where Ki67 immunolabeling is displayed. Bars indicate mean±SEM. * indicates p<0.02 and ** indicates p <0.001. The numbers of islet donors used in each experiment are the same as in FIG. 1A. FIG. 3B is a graph showing BrdU incorporation into beta cells in dispersed islets in response to the conditions shown. BrdU was added to the cultures 18 hours prior to fixation. Bars indicate mean±SEM. The numbers within or above the bars indicate the numbers of human islet donors used for each condition. FIG. 3C are images showing an example of BrdU incorporation in human islet treated with control vehicle or the 10 µM harmine-5 nM GLP1 combination. FIGS. 3D-3E are graphs showing the same type of experiments as shown in FIGS. 1A and 3A, except that lower doses, 3 µM (FIG. 3D) and 1 µM (FIG. 3E) harmine are used. Again, note that clear synergy is evident, particularly in FIG. 3E, where harmine and GLP1 induce little or no proliferation, but the combination induces the same degree of proliferation as the 10 µM harmine dose (2.7%). Bars indicate mean±SEM. The numbers within or above the bars indicate the numbers of human islet donors used for each condition. * indicates p<0.05 and ** indicates p <0.01.

FIGS. 5A-5C are graphs showing the results of experiments in which agents that increase cAMP (forskolin, di-butyryl cAMP, and the phosphodiesterase inhibitors, isobuytlmethyxanthine (IBMX) and dipyridamole (DPD), have no effect on proliferation when administered alone, but can replace GLP1 when administered together with harmine. FIG. 5D is a graph showing the results of an experiment in which the PKA inhibitor H89 has no effect on its own, but blocks the synergistic proliferation induced by harmine and GLP1. Thus, the synergy is mediated in part by PKA. See FIGS. 5F-5H for additional evidence of PKA and EPAC mediation of the synergy. FIG. 5E is a graph showing the effect of the PKA activator 6-bnz-cAMP on harmine-induced human beta cell proliferation. FIG. 5F is a graph showing the effects of the EPAC2 activator, 8-CPT-cAMP, on the harmine-induced proliferation. FIG. 5G is a graph demonstrating that EPAC2 is the most abundant EPAC in FACS-sorted human beta cells and also in other islet cell types (see RNA sequencing data from Wang et al., "Insights into Human Beta Cell Regeneration for Diabetes via Integration of Molecular Landscapes in Human Insulinomas. *Nat. Comm.* 8(1):767 (2017), which is hereby incorporated by reference in its entirety). In contrast, EPAC1 is only marginally detectable. FIG. 5H is a graph showing the effects of the EPAC2 inhibitor ESI-05 on the harmine combination. In FIGS. 5E, 5F, and 5H, bars indicate mean±SEM. The numbers within or above the bars indicate the numbers of human islet donors used for each condition.

FIG. 6A is a graph showing the results of an experiment in which dispersed human islets were treated as indicated. "GLP1" indicates 5 nM GLP1, "Har" indicates harmine 10 µM, "Con.sh" indicates a control adenovirus expressing an shRNA against beta galactosidase, and "DYRK1A-sh" indicates an adenovirus expressing a shRNA directed against DYRK1A, as described previously (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015), which is hereby incorporated by reference in its entirety) and in FIGS. 5E-5G and 6D-6F (infra). Note that silencing DYRK1A adenovirally achieves the same GLP1 synergy observed with GLP1 and harmine. FIG. 6B is a graph showing the converse experiment to FIG. 6A. Here, either a DYRK1A cDNA or a control (Cre) were adenovirally (CMV promoter) overexpressed in human islets. Note that DYRK1A overexpression blocks both the effect of harmine and of the harmine-GLP1 combination. FIG. 6C shows examples of immunolabeling for insulin and Ki67 in FIGS. 6A-6B. FIG. 6D is a graph showing the results of quantitative PCR display of adenoviral overexpression of DYRK1A in four sets of dispersed human islets. DYRK1A silencing increases DYRK1A mRNA expression by ~25-fold. FIG. 6E shows immunohistochemistry demonstrating DYRK1A overexpression at the protein level in beta cells in response to the Ad.DYRK1A. FIG. 6F is a graph showing that adenoviral silencing of DYRK1A in human islets reduces DYRK1A expression in human islets by ~80%. Bars indicate mean±SEM. The numbers within or above the bars indicate the numbers of human islet donors used for each condition. * indicates p<0.01. In all panels, the bars indicate mean±SEM, and the number of separate human islets is shown within the bars. p-values are as indicated. As in earlier figures, the value for harmine is normalized to 1.0 and the other values expressed as a function of that value.

FIG. 7A is a graph showing the effects on cell cycle activators, 72 hours after exposure to the four conditions. FIG. 7B shows the effects on cell cycle inhibitors on the same samples. The gene names for the cell cycle inhibitors are CDKN2B, CDKN2A, CDKN2C, CDKN2D, CDKN1A, CDKN1B, and CDKN1C, for p15$^{INK4}$, p16$^{INK4}$, p18$^{INK4}$, p19$^{INK4}$, p21$^{CIP}$, p27$^{CIP}$, and p57$^{KIP}$, respectively. Bars indicate mean±SEM. The numbers within or above the bars indicate the numbers of human islet donors used for each condition. * indicates p<0.05 and ** indicates p<0.005.

FIG. 8A is a graph showing the effects of control vehicle (DMSO, 0.1%), GLP1 5 nM, harmine 10 µM, or the combination on markers of beta cell differentiation as assessed using qPCR. The bars indicate mean±SEM, and the numbers within or above the bars indicate the number of human islet preparations studied under each condition. * indicates p<0.05 and

** indicates p<0.008 vs. control vehicle treatment. FIG. 8B shows images of immunolabeling of beta cells for PDX1, MAFA, and NKX6.1 from experiments shown in FIG. 8A. Note that each increases in beta cell nuclei with harmine or the combination. Representative of experiments in four human islet preparations. FIG. 8C is a graph showing insulin secretion from human islets from four different donors in response to low (2.8 mM, grey bars) and high (16.8 mM, black bars) glucose following 72 hr treatment with vehicle, GLP1 (5 nM), harmine (10 µM), or the combination. Data are represented as fold increase in insulin following high glucose stimulation. The insulin concentration (mean±SEM) in the 2.8 mM glucose control (DMSO) wells was 19.9±9.1 pmol/islet, and at 16.7 mM glucose was 33.3±12.6 pmol/islet.

FIG. 9A is a graph showing the effects of harmine with or without GLP1 on the same differentiation markers shown in FIG. 8A. The harmine or the harmine-GLP1 combination did not have adverse effects on differentiation. Rather, it appears to increase PDX1, MAFB, NKX6.1, GLUT2, GLP1R, and PCSK1 in islets from people with T2D. The bars indicate mean±SEM, and the numbers within or above the bars indicate the number of human islet preparations studied under each condition. * indicates $p<0.05$ and ** indicates $p<0.008$ vs. control vehicle treatment. FIG. 9B presents images showing examples of PDX1, MAFA, and NKX6.1 immunolabeling of dispersed human T2D islets following the treatments shown. Note that all three increase at the protein level within beta cells. The increase is apparent for MAFA even in the absence of an increase at the mRNA level in FIG. 9A. FIG. 9C is a graph showing the insulin secretion in response to low (2.8 mM, grey bars) and high (16.8 mM, black bars) glucose in three different T2D islet preparations pre-treated with vehicle, GLP1, harmine, or the combination for 72 hrs. Data are represented as fold increase in insulin following high glucose stimulation. The average insulin concentration in the 2.8 mM glucose control (DMSO) wells was 18.1±3.2 pmol/islet, and at 16.7 mM glucose was 32.2±4.6 pmol/islet. Error bars indicate the mean±SEM. * indicates $p<0.01$ vs low glucose ** indicates $p<0.02$ vs vehicle treated, high glucose response. FIG. 9D is a graph showing human T2D beta cell proliferation in response to vehicle, GLP1, harmine, or the combination. The bars indicate mean±SEM, and the numbers within or above the bars indicate the number of human islet preparations studied under each condition. * indicates $p<0.01$ and ** indicates $p=0.02$ vs. control vehicle treatment and vs. harmine alone. FIG. 9E shows examples of insulin and Ki67 immunolabeling in beta cells derived from donors with T2D.

FIG. 10A is a graph showing the proliferation as assessed using BrdU labeling in beta (INS), alpha (GCG), delta (SST), and ductal (CK19$^+$) cells in response to the treatments shown in the insert. Note that harmine activates proliferation in all four cell types, as reported previously (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015), which is hereby incorporated by reference in its entirety), and GLP1 accentuates this on beta and ductal cells that contain GLP1 receptors. Bars indicate mean±SEM. The numbers below the bars indicate the numbers of human islet donors used for each condition. FIG. 10B shows examples of BrdU immunolabeling in human islet cell subtypes in response to the agents shown. FIG. 10C is a graph showing the effects of the harmine-GLP1 combination on cell death as assessed by TUNEL assay. The cytokine cocktail in the second bar is a positive control, and contains IFNγ, TNFα, and IL1β as described in the Examples (infra). Bars indicate mean±SEM. The numbers within the bars indicate the numbers of human islet donors used for each condition. FIG. 10D shows examples of TUNEL responses to the conditions shown in FIG. 10C.

DETAILED DESCRIPTION

Figures 1A, 1B, 1C, 1D, 1E:
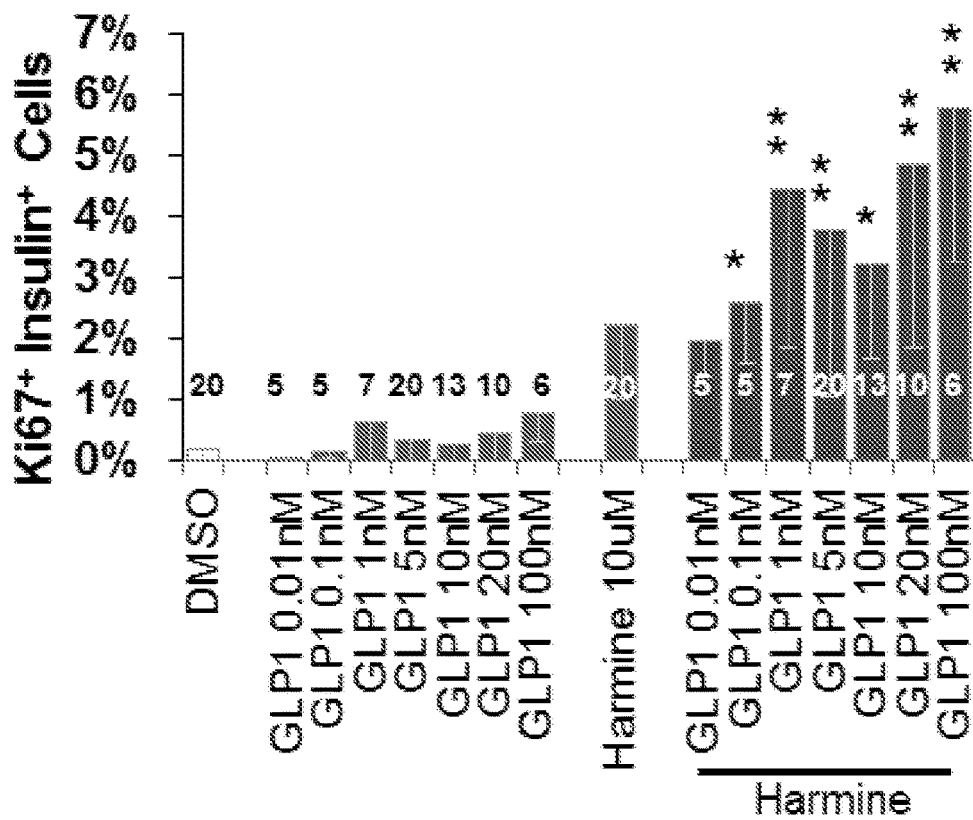
FIGS. 1A-1G demonstrate that the combination of DYRK1A inhibitors with a GLP1R agonist yields synergistic increases in human beta cell proliferation.
Figure 1F:
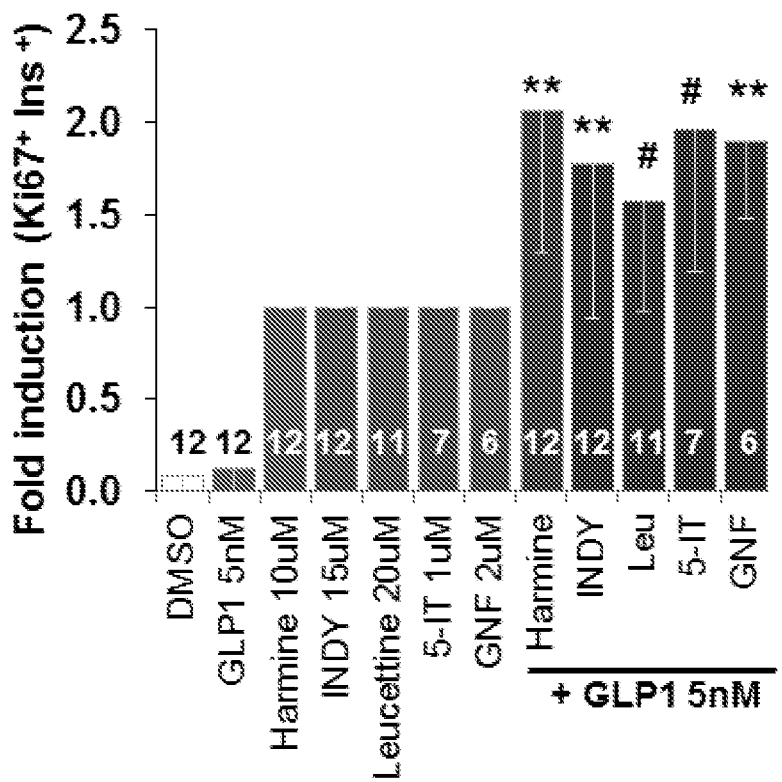
Figure 1G:
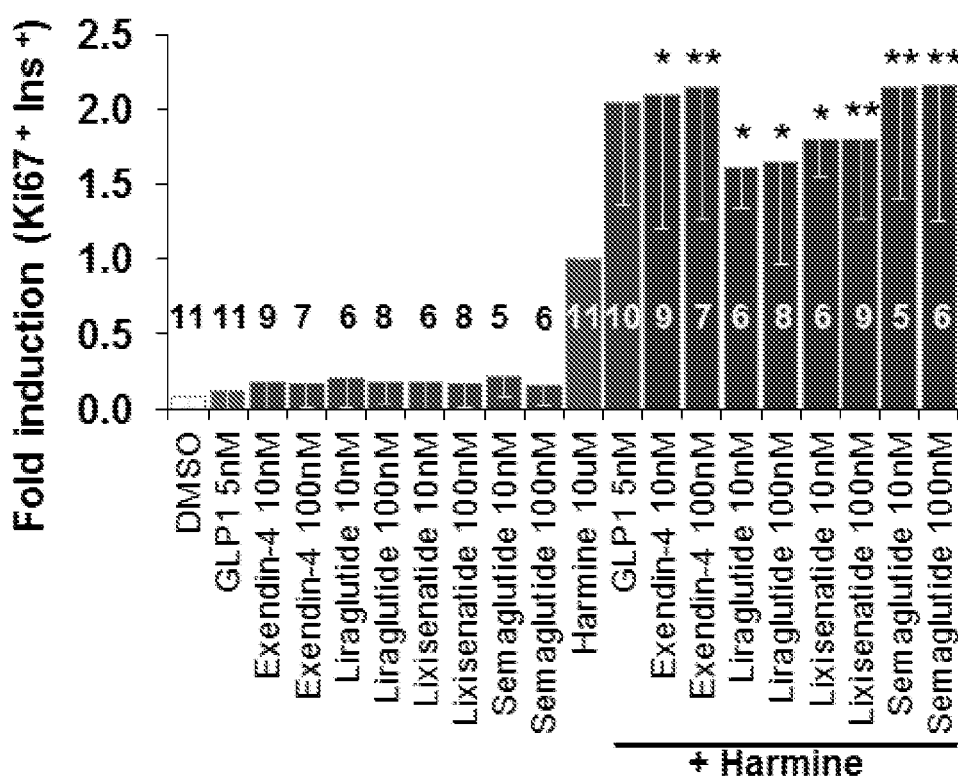
Figure 2:
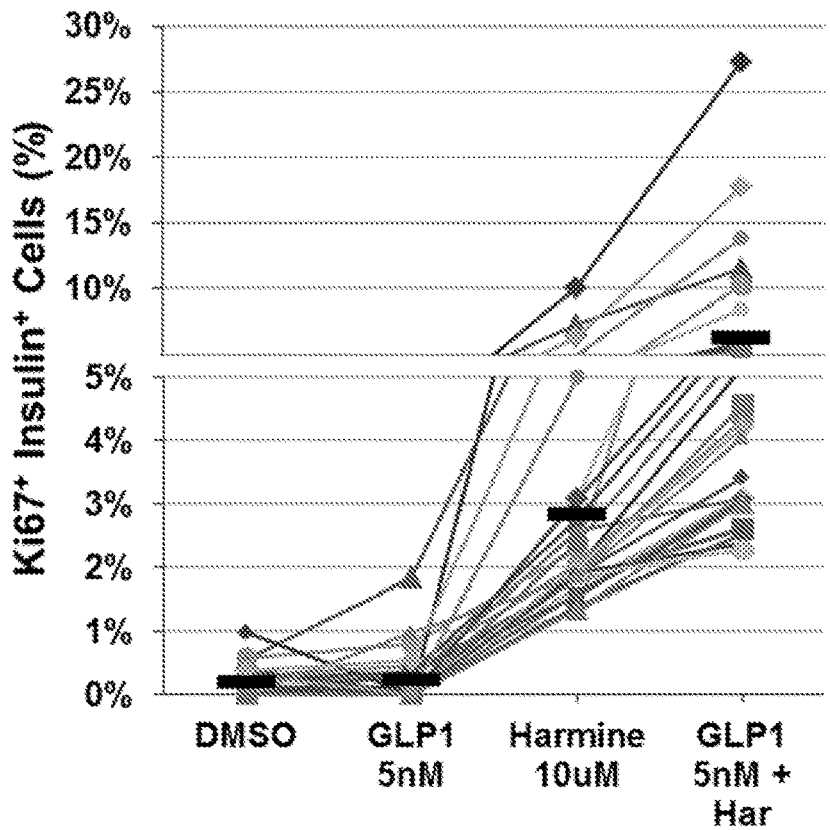
FIG. 2 shows the individual donor Ki67-insulin immunolabeling data for FIGS. 1A and 3A. The presentation format of FIG. 2 displays proliferative responses to DMSO (0.1%), harmine (10 μM), GLP1 (5 nM) or the GLP1-harmine combination in the twenty human islet donors shown in FIGS. 1A and 3A. The dense black bars represent the mean values for each treatment condition. Standard errors and statistical significance are shown in FIG. 1A. This figure highlights the well-recognized variability in responsiveness among different human islet donors. It also demonstrates that every human islet donor displayed enhanced proliferation in response to the harmine-GLP1 combination.

Disclosed are methods of increasing cell proliferation in a population of pancreatic beta cells, methods of treating a subject for a condition associated with insufficient insulin secretion, and compositions comprising a dual-specificity tyrosine phosphorylation-regulated kinase 1A inhibitor and an agent that increases glucagon-like peptide-1 receptor activity.

One aspect relates to a method of increasing cell proliferation in a population of pancreatic beta cells. This method involves contacting a population of pancreatic beta cells with a dual-specificity tyrosine phosphorylation-regulated kinase 1A (DYRK1A) inhibitor and an agent that increases glucagon-like peptide-1 receptor (GLP1R) activity, where said contacting is carried out under conditions effective to cause a synergistic increase in cell proliferation in the population of pancreatic beta cells. Suitable agents that increase GLP1R activity are described infra, and include, without limitation, GLP1R agonists and DPP4 inhibitors.

In carrying out this and other methods described herein, the pancreatic beta cells may be mammalian cells. Mammalian cells include cells from, for example, mice, hamsters, rats, cows, sheep, pigs, goats, horses, monkeys, dogs (e.g., *Canis familiaris*), cats, rabbits, guinea pigs, and primates, including humans. For example, the cells may be human pancreatic beta cells.

According to one embodiment, "pancreatic beta cells" are primary human pancreatic beta cells.

In one embodiment, this and other methods described herein are carried out ex vivo or in vivo. When carried out ex vivo, a population of cells may be provided by obtaining cells from a pancreas and culturing the cells in a liquid medium suitable for the in vitro or ex vivo culture of mammalian cells, in particular human cells. For example, and without limitation, a suitable and non-limiting culture medium may be based on a commercially available medium such as RPMI1640 from Invitrogen.

Methods for determining whether a cell has a pancreatic beta cell phenotype are known in the art and include, without limitation, incubating the cell with glucose and testing whether insulin expression in the cell is increased or induced. Other methods include testing whether beta cell specific transcription factors are expressed, the detection of beta cell specific gene products with the help of RNA quantitative PCR, the transplantation of a candidate cell in diabetic mice, and subsequent testing of the physiologic response following said transplantation as well as analyzing the cells with electron microscopy.

Several DYRK1A inhibitors from natural sources as well as small molecule drug discovery programs have been identified and characterized. Suitable DYRK1A inhibitors include, without limitation, harmine, INDY, leucettine-41, 5-iodotubercidin (5-IT), GNF4877, harmine analogs, CC-401, thiadiazine kinase inhibitors, and others. Additional suitable DYRK1A inhibitors include, but are not limited to, GNF7156 and GNF6324 (Shen et al., "Inhibition of DYRK1A and GSK3B Induces Human Beta Cell Proliferation," *Nat. Commun.* 6:8372 (2015), which is hereby incorporated by reference in its entirety). In carrying out the methods of the present invention or forming the compositions of the present invention, combinations of DYRK1A inhibitors may used. Among all the DYRK1A inhibitors, harmine and its analogues (β-carbolines) are the most commonly studied and remain the most potent and orally bioavailable class of inhibitors covered to date (Becker et al., "Activation, Regulation, and Inhibition of DYRK1A," *FEBS* 278(2):246-256 (2011) and Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012), which are hereby incorporated by reference in their entirety).

Apart from harmine, EGCg and other flavan-3-ols (Guedj et al., "Green Tea Polyphenols Rescue of Brain Defects Induced by Overexpression of DYRK1A," *PLoS One* 4(2): e4606 (2009) and Bain et al., "The Specificities of Protein Kinase Inhibitors: An Update," *Biochem. J.* 371(1):199-204 (2003), which are hereby incorporated by reference in their entirety), leucettines (Tahtouh et al., "Selectivity, Cocrystal Structures, and Neuroprotective Properties of Leucettines, a Family of Protein Kinase Inhibitors Derived from the Marine Sponge Alkaloid Leucettamine B," *J. Med. Chem.* 55(21):9312-9330 (2012) and Naert et al., "Leucettine L41, a DYRK1A-preferential DYRKs/CLKs Inhibitor, Prevents Memory Impairments and Neurotoxicity Induced by Oligomeric Aβ25-35 Peptide Administration in Mice," *Eur. Neuropsychopharmacol.* 25(11):2170-2182 (2015), which are hereby incorporated by reference in their entirety), quinalizarine (Cozza et al., "Quinalizarin as a Potent, Selective and Cell-permeable Inhibitor of Protein Kinase CK2," *Biochem. J.* 421(3):387-395 (2009), which is hereby incorporated by reference in its entirety), peltogynoids Acanilol A and B (Ahmadu et al, "Two New Peltogynoids from Acacia nilotica Delile with Kinase Inhibitory Activity," *Planta Med.* 76(5):458-460 (2010), which is hereby incorporated by reference in its entirety), benzocoumarins (dNBC) (Sarno et al., "Structural Features Underlying the Selectivity of the Kinase Inhibitors NBC and dNBC: Role of a Nitro Group that Discriminates Between CK2 and DYRK1A," *Cell. Mol. Life Sci.* 69(3):449-460 (2012), which is hereby incorporated by reference in its entirety), and indolocarbazoles (Starosporine, rebeccamycin and their analogues) (Sanchez et al., "Generation of Potent and Selective Kinase Inhibitors by Combinatorial Biosynthesis of Glycosylated Indolocarbazoles," *Chem. Commun.* 27:4118-4120 (2009), which is hereby incorporated by reference in its entirety), are other natural products that have been shown to inhibit DYRK1A and other kinases.

Among the other scaffolds identified from small molecule drug discovery attempts, INDY (Ogawa et al., "Development of a Novel Selective Inhibitor of the Down Syndrome-Related Kinase Dyrk1A," *Nat. Commun.* 1: Article Number 86 (2010), which is hereby incorporated by reference in its entirety), DANDY (Gourdain et al., "Development of DANDYs, New 3,5-Diaryl-7-Azaindoles Demonstrating Potent DYRK1A Kinase Inhibitory Activity," *J. Med. Chem.* 56(23):9569-9585 (2013), which is hereby incorporated by reference in its entirety), and FINDY (Kii et al., "Selective Inhibition of the Kinase DYRK1A by Targeting its Folding Process," *Nat. Commun.* 7:11391 (2016), which is hereby incorporated by reference in its entirety), pyrazolidine-diones (Koo et al., "QSAR Analysis of Pyrazolidine-3,5-Diones Derivatives as Dyrk1A Inhibitors," *Bioorg. Med. Chem. Lett.* 19(8):2324-2328 (2009); Kim et al., "Putative Therapeutic Agents for the Learning and Memory Deficits of People with Down Syndrome," *Bioorg. Med. Chem. Lett.* 16(14):3772-3776 (2006), which are hereby incorporated by reference in their entirety), amino-quinazolines (Rosenthal et al., "Potent and Selective Small Molecule Inhibitors of Specific Isoforms of Cdc2-Like Kinases (Clk) and Dual Specificity Tyrosine-Phosphorylation-Regulated Kinases (Dyrk)," *Bioorg. Med. Chem. Lett.* 21(10):3152-3158 (2011), which is hereby incorporated by reference in its entirety), meriolins (Giraud et al., "Synthesis, Protein Kinase Inhibitory Potencies, and In Vitro Antiproliferative Activities of Meridianin Derivatives," *J. Med. Chem.* 54(13):4474-4489 (2011); Echalier et al., "Meriolins (3-(Pyrimidin-4-yl)-7-Azaindoles): Synthesis, Kinase Inhibitory Activity, Cellular Effects, and Structure of a CDK2/Cyclin A/Meriolin Complex," *J. Med. Chem.* 51(4):737-751 (2008); and Akue-Gedu et al., "Synthesis and Biological Activities of Aminopyrimidyl-Indoles Structurally Related to Meridianins," *Bioorg. Med. Chem.* 17(13):4420-4424 (2009), which are hereby incorporated by reference in their entirety), pyridine and pyrazines (Kassis et al., "Synthesis and Biological Evaluation of New 3-(6-hydroxyindol-2-yl)-5-(Phenyl) Pyridine or Pyrazine V-Shaped Molecules as Kinase Inhibitors and Cytotoxic Agents," *Eur. J. Med. Chem.* 46(11):5416-5434 (2011), which is hereby incorporated by reference in its entirety), chromenoidoles (Neagoie et al., "Synthesis of Chromeno[3,4-b]indoles as Lamellarin D Analogues: A Novel DYRK1A Inhibitor Class," *Eur. J. Med. Chem.* 49:379-396 (2012), which is hereby incorporated by reference in its entirety), 11H-indolo[3,2-c]quinoline-6-carboxylic acids, thiazolo[5,4-f]quinazolines (EHT 5372) (Foucourt et al., "Design and Synthesis of Thiazolo [5,4-f]quinazolines as DYRK1A Inhibitors, Part I.," *Molecules* 19(10):15546-15571 (2014) and Coutadeur et al., "A Novel DYRK1A (Dual Specificity Tyrosine Phosphorylation-Regulated Kinase 1A) Inhibitor for the Treatment of Alzheimer's Disease: Effect on Tau and Amyloid Pathologies In Vitro," *J. Neurochem.* 133(3):440-451 (2015), which are hereby incorporated by reference in their entirety), and 5-iodotubercidin (Dirice et al., "Inhibition of DYRK1A Stimulates Human Beta Cell Proliferation," *Diabetes* 65(6): 1660-1671 (2016) and Annes et al., "Adenosine Kinase Inhibition Selectively Promotes Rodent and Porcine Islet β-cell Replication," *Proc. Natl. Acad. Sci.* 109(10):3915-3920 (2012), which are hereby incorporated by reference in their entirety) show potent DYRK1A activity with varying degrees of kinase selectivity.

Suitable thiadiazine kinase inhibitors include, for example and without limitation, those described in PCT Application No. PCT/US2018/062023, filed Nov. 20, 2018, which is hereby incorporated by reference in its entirety. Specific examples include those shown in Tables 1 and 2.

TABLE 1

Thiadiazine Kinase Inhibitors

| Chemical Name | Structure |
| --- | --- |
| N-benzyl-5-(benzo[d]imidazol-2(3H)-one)-6H-1,3,4-thiadiazin-2-amine | 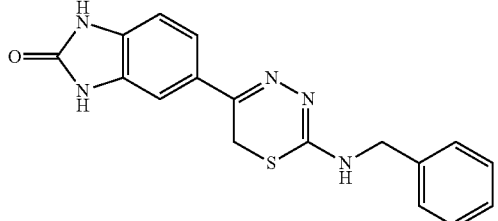 |
| N-(4-chlorobenzyl)-5-(benzo[d]imidazol-2(3H)-one)-6H-1,3,4-thiadiazin-2-amine | 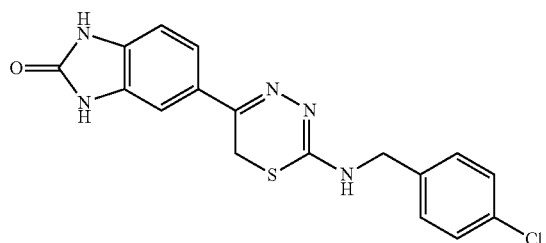 |
| N-(3-chlorobenzyl)-5-(benzo[d]imidazol-2(3H)-one)-6H-1,3,4-thiadiazin-2-amine | 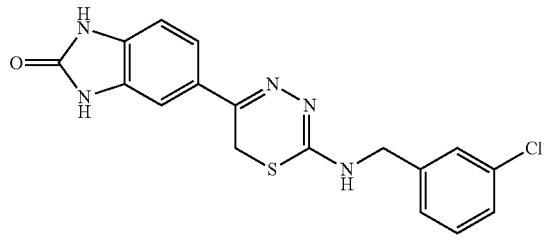 [SMILES: O=c1[nH]c2ccc(C3=NN=C(NCc4cccc(Cl)c4)SC3)cc2[nH]1] |
| N-(2-chlorobenzyl)-5-(benzo[d]imidazol-2(3H)-one)-6H-1,3,4-thiadiazin-2-amine | 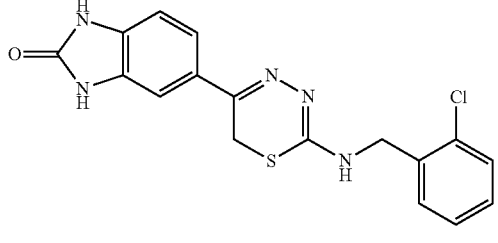 |
| N-(4-fluorobenzyl)-5-(benzo[d]imidazol-2(3H)-one)-6H-1,3,4-thiadiazin-2-amine | 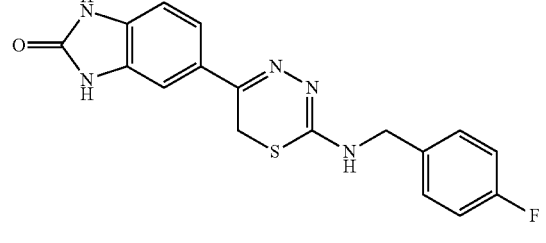 |
| N-(3-fluorobenzyl)-5-(benzo[d]imidazol-2(3H)-one)-6H-1,3,4-thiadiazin-2-amine | 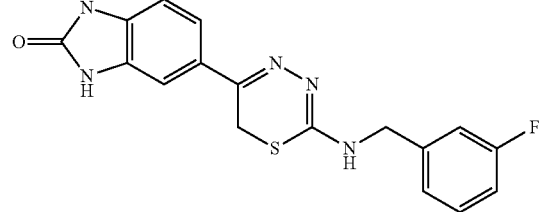 |

TABLE 1-continued

Thiadiazine Kinase Inhibitors

| Chemical Name | Structure |
| --- | --- |
| N-(2-fluorobenzyl)-5-(benzo[d]imidazol-2(3H)-one)-6H-1,3,4-thiadiazin-2-amine | 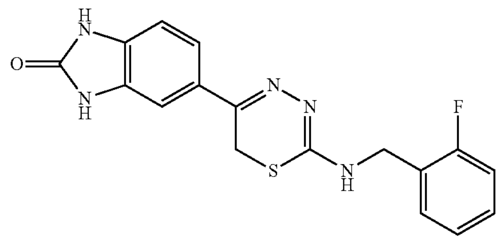 [SMILES: O=c1[nH]c2ccc(C3=NN=C(NCc4ccccc4Cl)SC3)cc2[nH]1] |
| N-(4-trifluoromethylbenzyl)-5-(benzo[d]imidazol-2(3H)-one)-6H-1,3,4-thiadiazin-2-amine | 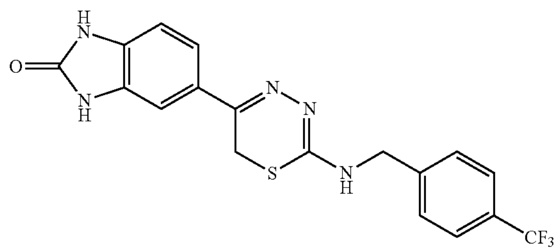 [SMILES: O=c1[nH]c2ccc(C3=NN=C(NCc4ccc(C(F)(F)F)cc4)SC3)cc2[nH]1] |
| N-(3-trifluoromethylbenzyl)-5-(benzo[d]imidazol-2(3H)-one)-6H-1,3,4-thiadiazin-2-amine | 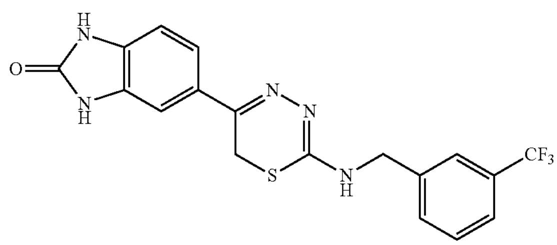 [SMILES: O=c1[nH]c2ccc(C3=NN=C(NCc4cccc(C(F)(F)F)c4)SC3)cc2[nH]1] |
| N-(2-trifluoromethylbenzyl)-5-(benzo[d]imidazol-2(3H)-one)-6H-1,3,4-thiadiazin-2-amine | 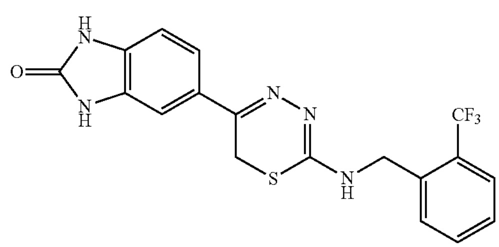 |
| N-(4-cyanobenzyl)-5-(benzo[d]imidazol-2(3H)-one)-6H-1,3,4-thiadiazin-2-amine | 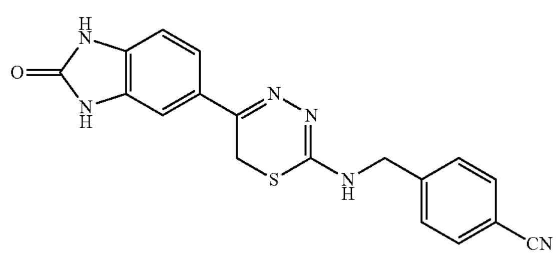 [SMILES: N#Cc1ccc(CNC2=NN=C(c3ccc4[nH]c(=O)[nH]c4c3)CS2)cc1] |
| N-(3-cyanobenzyl)-5-(benzo[d]imidazol-2(3H)-one)-6H-1,3,4-thiadiazin-2-amine | 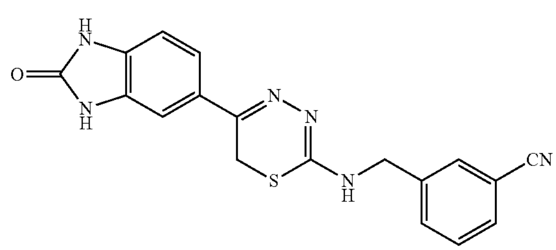 [SMILES: N#Cc1cccc(CNC2=NN=C(c3ccc4[nH]c(=O)[nH]c4c3)CS2)c1] |

TABLE 1-continued

Thiadiazine Kinase Inhibitors

| Chemical Name | Structure |
| --- | --- |
| N-(pyridine-3yl)methyl-5-(benzo[d]imidazol-2(3H)-one)-6H-1,3,4-thiadiazin-2-amine | 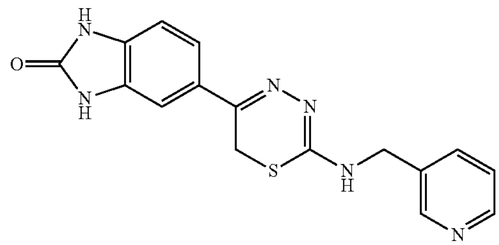 [SMILES: O=c1[nH]c2ccc(C3=NN=C(NCc4cccnc4)SC3)cc2[nH]1] |
| N-(pyridine-4yl)methyl-5-(benzo[d]imidazol-2(3H)-one)-6H-1,3,4-thiadiazin-2-amine | 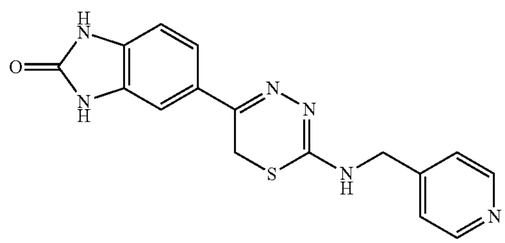 [SMILES: O=c1[nH]c2ccc(C3=NN=C(NCc4ccncc4)SC3)cc2[nH]1] |
| N-(3-carboxyaminobenzyl)-5-(benzo[d]imidazol-2(3H)-one)-6H-1,3,4-thiadiazin-2-amine | 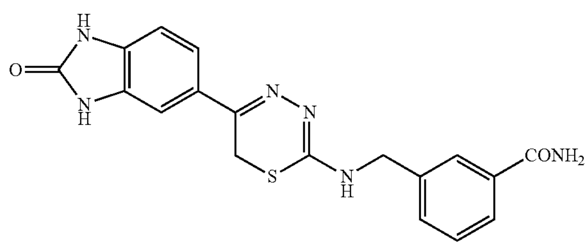 [SMILES: NC(=O)c1cccc(CNC2=NN=C(c3ccc4[nH]c(=O)[nH]c4c3)CS2)c1] |
| N-(1-phenylethyl)-5-(benzo[d]imidazol-2(3H)-one)-6H-1,3,4-thiadiazin-2-amine | 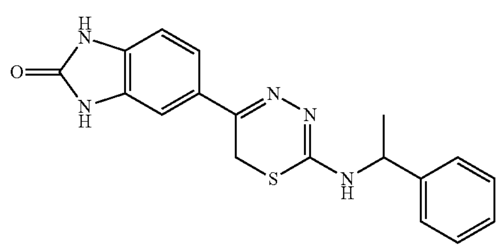 [SMILES: CC(NC1=NN=C(c2ccc3[nH]c(=O)[nH]c3c2)CS1)c1ccccc1] |
| N-(1-(4-fluorophenyl)ethyl)-5-(benzo[d]imidazol-2(3H)-one)-6H-1,3,4-thiadiazin-2-amine | 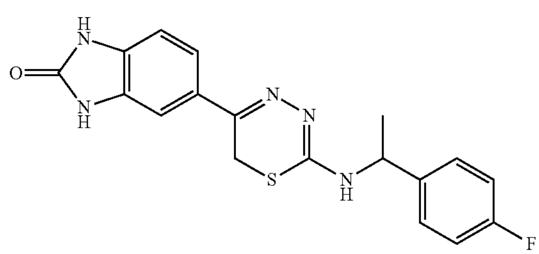 [SMILES: CC(NC1=NN=C(c2ccc3[nH]c(=O)[nH]c3c2)CS1)c1ccc(F)cc1] |
| N-phenyl-5-(benzo[d]imidazol-2(3H)-one)-6H-1,3,4-thiadiazin-2-amine | 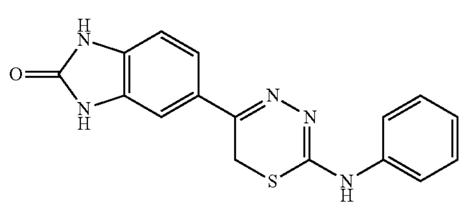 [SMILES: O=c1[nH]c2ccc(C3=NN=C(Nc4ccccc4)SC3)cc2[nH]1] |

TABLE 1-continued

Thiadiazine Kinase Inhibitors

| Chemical Name | Structure |
| --- | --- |
| N-(3-fluorophenyl)-5-(benzo[d]imidazol-2(3H)-one)-6H-1,3,4-thiadiazin-2-amine | 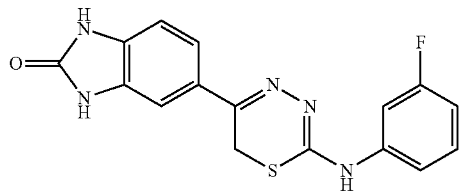 [SMILES: O=c1[nH]c2ccc(C3=NN=C(Nc4cccc(F)c4)SC3)cc2[nH]1] |
| N-(3-trifluoromethylphenyl)-5-(benzo[d]imidazol-2(3H)-one)-6H-1,3,4-thiadiazin-2-amine | 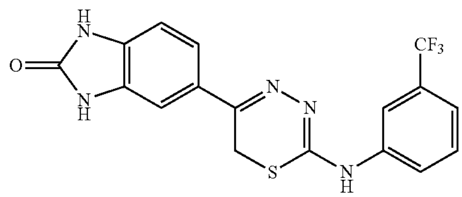 |
| N-(3-cyanophenyl)-5-(benzo[d]imidazol-2(3H)-one)-6H-1,3,4-thiadiazin-2-amine | 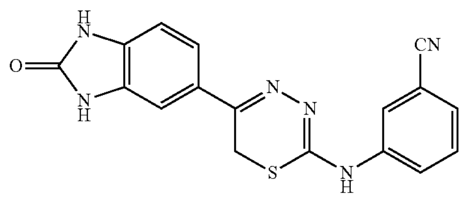 [SMILES: N#Cc1cccc(NC2=NN=C(c3ccc4[nH]c(=O)[nH]c4c3)CS2)c1] |
| N-(2-phenylethyl)-5-(benzo[d]imidazol-2(3H)-one)-6H-1,3,4-thiadiazin-2-amine | 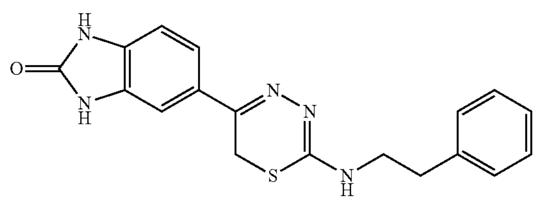 [SMILES: O=c1[nH]c2ccc(C3=NN=C(NCCc4ccccc4)SC3)cc2[nH]1] |
| N-(3-phenylpropyl)-5-(benzo[d]imidazol-2(3H)-one)-6H-1,3,4-thiadiazin-2-amine | 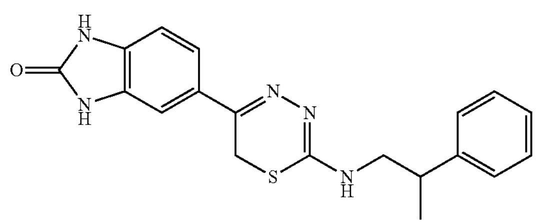 [SMILES: CC(CNC1=NN=C(c2ccc3[nH]c(=O)[nH]c3c2)CS1)c1ccccc1] |
| N-(2-(pyridine-3-yl)ethyl)-5-(benzo[d]imidazol-2(3H)-one)-6H-1,3,4-thiadiazin-2-amine | 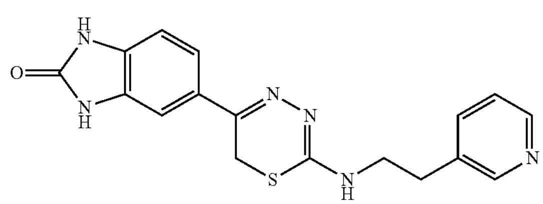 [SMILES: O=c1[nH]c2ccc(C3=NN=C(NCCc4cccnc4)SC3)cc2[nH]1] |
| N-(2-naphthylmethy)-5-(benzo[d]imidazol-2(3H)-one)-6H-1,3,4-thiadiazin-2-amine | 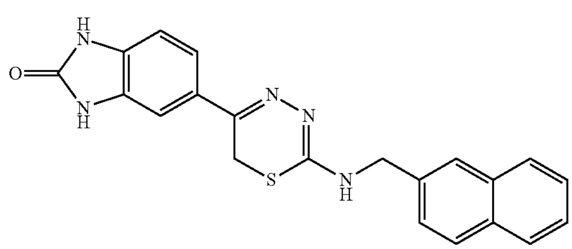 [SMILES: O=c1[nH]c2ccc(C3=NN=C(NCc4ccc5ccccc5c4)SC3)cc2[nH]1] |

TABLE 1-continued

Thiadiazine Kinase Inhibitors

| Chemical Name | Structure |
|---|---|
| N-(1-naphthylmethy)-5-(benzo[d]imidazol-2(3H)-one)-6H-1,3,4-thiadiazin-2-amine | 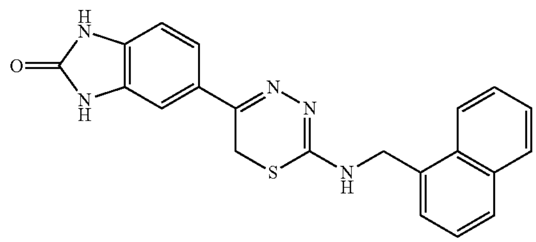 [SMILES: O=c1[nH]c2ccc(C3=NN=C(NCc4cccc5ccccc45)SC3)cc2[nH]1] |
| N-(1-naphthyl)-5-(benzo[d]imidazol-2(3H)-one)-6H-1,3,4-thiadiazin-2-amine | 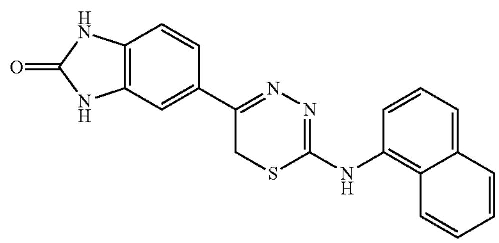 [SMILES: O=c1[nH]c2ccc(C3=NN=C(Nc4cccc5ccccc45)SC3)cc2[nH]1] |
| 5-(2-((2-(pyridin-2-yl)ethyl)amino)-6H-1,3,4-thiadiazin-5-yl)-1,3-dihydro-2H-benzo[d]imidazol-2-one | 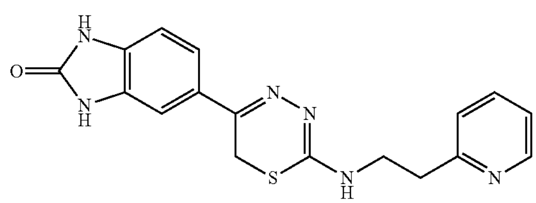 |

TABLE 2

Additional Thiadiazine Kinase Inhibitors

| Chemical Name | Structure |
|---|---|
| N-methyl-5-(benzo[d]imidazol-2(3H)-one)-6H-1,3,4-thiadiazin-2-amine | 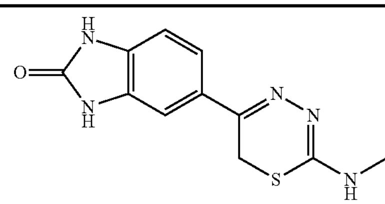 |
| N-ethyl-5-(benzo[d]imidazol-2(3H)-one)-6H-1,3,4-thiadiazin-2-amine | 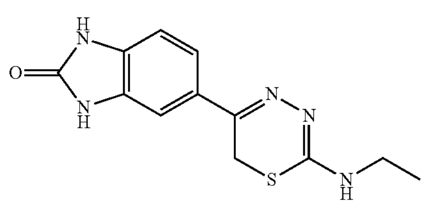 [SMILES: CCNC1=NN=C(c2ccc3[nH]c(=O)[nH]c3c2)CS1] |
| N-propyl-5-(benzo[d]imidazol-2(3H)-one)-6H-1,3,4-thiadiazin-2-amine | 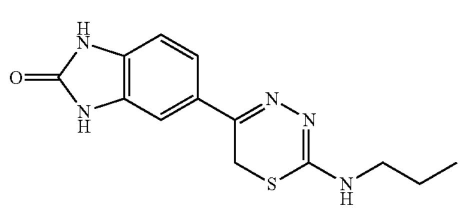 [SMILES: CCCNC1=NN=C(c2ccc3[nH]c(=O)[nH]c3c2)CS1] |

TABLE 2-continued

Additional Thiadiazine Kinase Inhibitors

| Chemical Name | Structure |
|---|---|
| N-butyl-5-(benzo[d]imidazol-2(3H)-one)-6H-1,3,4-thiadiazin-2-amine | 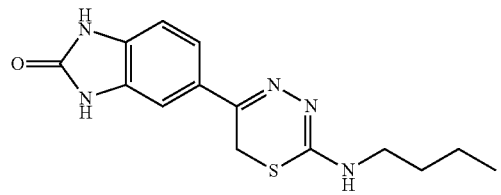 [SMILES: CCCCNC1=NN=C(c2ccc3[nH]c(=O)[nH]c3c2)CS1] |
| N-isopropyl-5-(benzo[d]imidazol-2(3H)-one)-6H-1,3,4-thiadiazin-2-amine | 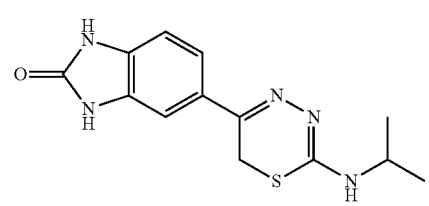 [SMILES: CC(C)NC1=NN=C(c2ccc3[nH]c(=O)[nH]c3c2)CS1] |
| N-t-butyl-5-(benzo[d]imidazol-2(3H)-one)-6H-1,3,4-thiadiazin-2-amine | 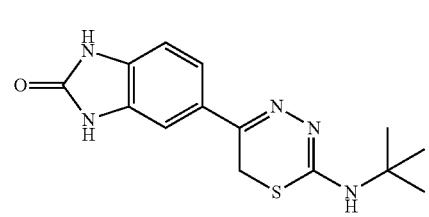 [SMILES: CC(C)(C)NC1=NN=C(c2ccc3[nH]c(=O)[nH]c3c2)CS1] |
| N-(3-methylbutyl)-5-(benzo[d]imidazol-2(3H)-one)-6H-1,3,4-thiadiazin-2-amine | 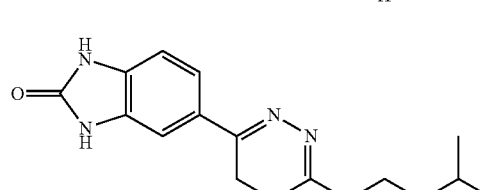 |
| N-cyclohexyl-5-(benzo[d]imidazol-2(3H)-one)-6H-1,3,4-thiadiazin-2-amine | 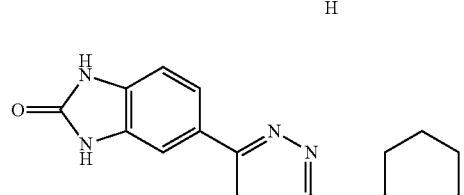 |
| N-(2-cyclohexylmethyl)-5-(benzo[d]imidazol-2(3H)-one)-6H-1,3,4-thiadiazin-2-amine | 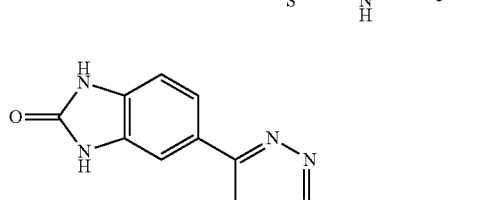 |
| N-(2-(morpholino)ethyl)-5-(benzo[d]imidazol-2(3H)-one)-6H-1,3,4-thiadiazin-2-amine | 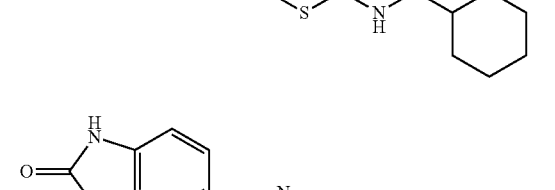 |

TABLE 2-continued

Additional Thiadiazine Kinase Inhibitors

| Chemical Name | Structure |
| --- | --- |
| N-(4-chlorobenzyl)-5-(benzo[d]imidazol-2(3H)-one)-6H-1,3,4-thiadiazin-2-amine | 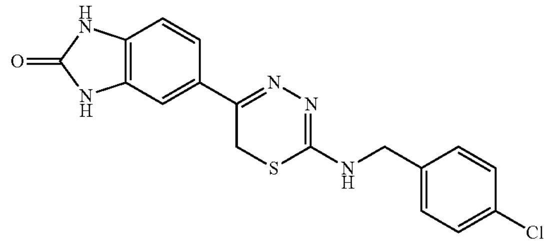 [SMILES: O=c1[nH]c2ccc(C3=NN=C(NCc4ccc(Cl)cc4)SC3)cc2[nH]1] |
| N-(3-cyanobenzyl)-5-(benzo[d]imidazol-2(3H)-one)-6H-1,3,4-thiadiazin-2-amine | 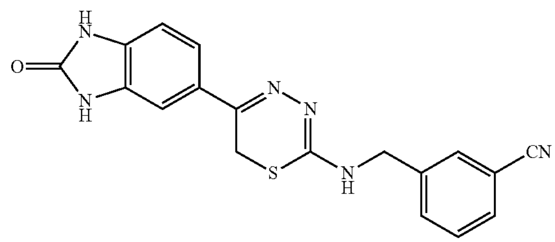 [SMILES: N#Cc1cccc(CNC2=NN=C(c3ccc4[nH]c(=O)[nH]c4c3)CS2)c1] |
| N-(4-carboxyaminobenzyl)-5-(benzo[d]imidazol-2(3H)-one)-6H-1,3,4-thiadiazin-2-amine | 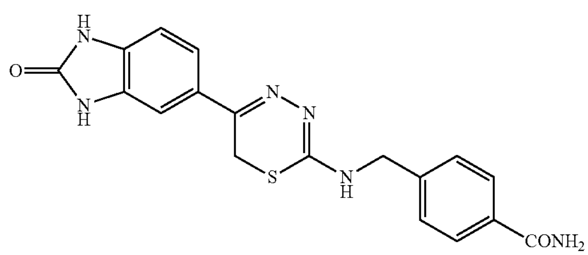 [SMILES: NC(=O)c1ccc(CNC2=NN=C(c3ccc4[nH]c(=O)[nH]c4c3)CS2)cc1] |
| N-(3-cyano-4-fluoro-benzyl)-5-(benzo[d]imidazol-2(3H)-one)-6H-1,3,4-thiadiazin-2-amine | 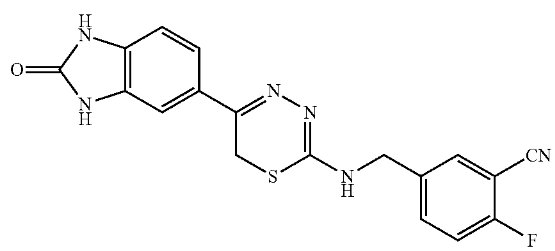 [SMILES: N#Cc1cc(CNC2=NN=C(c3ccc4[nH]c(=O)[nH]c4c3)CS2)ccc1F] |
| N-phenyl-5-(benzo[d]imidazol-2(3H)-one)-6H-1,3,4-thiadiazin-2-amine | 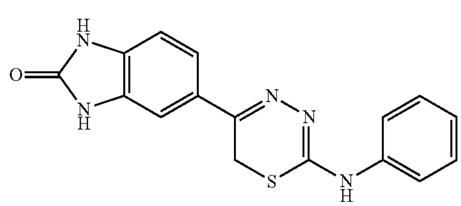 [SMILES: O=c1[nH]c2ccc(C3=NN=C(Nc4ccccc4)SC3)cc2[nH]1] |
| N-(3-cyanophenyl)-5-(benzo[d]imidazol-2(3H)-one)-6H-1,3,4-thiadiazin-2-amine | 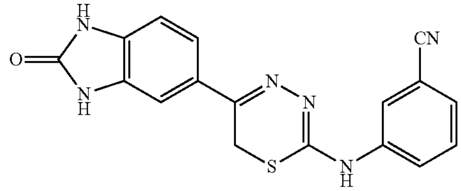 [SMILES: N#Cc1cccc(NC2=NN=C(c3ccc4[nH]c(=O)[nH]c4c3)CS2)c1] |

TABLE 2-continued

Additional Thiadiazine Kinase Inhibitors

| Chemical Name | Structure |
|---|---|
| N-(4-fluorophenyl)-5-(benzo[d]imidazol-2(3H)-one)-6H-1,3,4-thiadiazin-2-amine | |
| N-(4-fluorophenyl)-5-(benzo[d]imidazol-2(3H)-one)-6H-1,3,4-thiadiazin-2-amine | |
| N-(2-phenylethyl)-5-(benzo[d]imidazol-2(3H)-one)-6H-1,3,4-thiadiazin-2-amine | 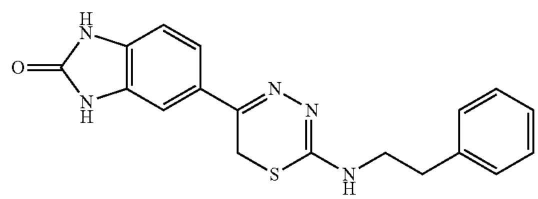 [SMILES: O=c1[nH]c2ccc(C3=NN=C(NCCc4ccccc4)SC3)cc2[nH]1] |
| N-(2-(4-fluorophenyl)ethyl)-5-(benzo[d]imidazol-2(3H)-one)-6H-1,3,4-thiadiazin-2-amine | 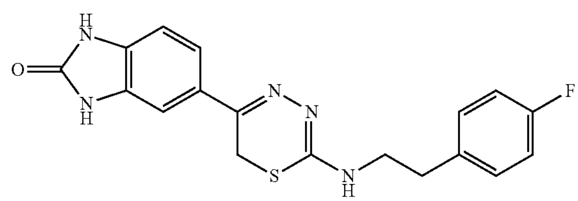 [SMILES: O=c1[nH]c2ccc(C3=NN=C(NCCc4ccc(F)cc4)SC3)cc2[nH]1] |
| N-(2-(4-chlorophenyl)ethyl)-5-(benzo[d]imidazol-2(3H)-one)-6H-1,3,4-thiadiazin-2-amine | 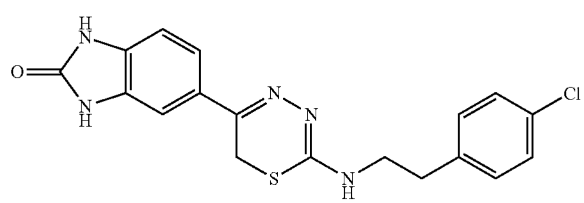 [SMILES: O=c1[nH]c2ccc(C3=NN=C(NCCc4ccc(Cl)cc4)SC3)cc2[nH]1] |
| N-(3-phenylpropyl)-5-(benzo[d]imidazol-2(3H)-one)-6H-1,3,4-thiadiazin-2-amine | 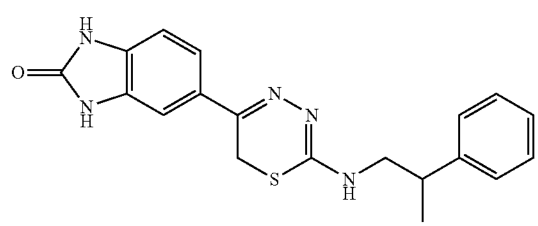 [SMILES: CC(CNC1=NN=C(c2ccc3[nH]c(=O)[nH]c3c2)CS1)c1ccccc1] |
| N-(2-(pyridine-1-yl)ethyl)-5-(benzo[d]imidazol-2(3H)-one)-6H-1,3,4-thiadiazin-2-amine | 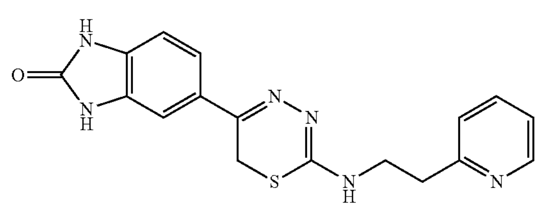 [SMILES: O=c1[nH]c2ccc(C3=NN=C(NCCc4ccccn4)SC3)cc2[nH]1] |

TABLE 2-continued

Additional Thiadiazine Kinase Inhibitors

| Chemical Name | Structure |
| --- | --- |
| N-(1-naphthyl)-5-(benzo[d]imidazol-2(3H)-one)-6H-1,3,4-thiadiazin-2-amine | 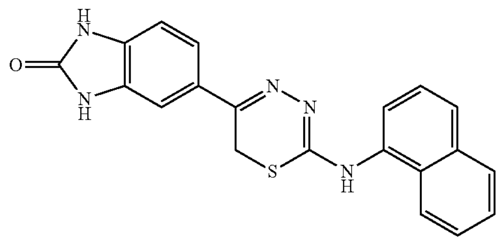 [SMILES: O=c1[nH]c2ccc(C3=NN=C(Nc4cccc5ccccc45)SC3)cc2[nH]1] |
| 5-(2-(cyclopropylamino)-6H-1,3,4-thiadiazin-5-yl)-1H-benzo[d]imidazol-2(3H)-one | 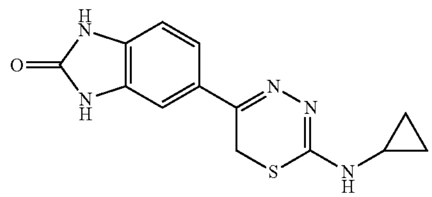 [SMILES: O=c1[nH]c2ccc(C3=NN=C(NC4CC4)SC3)cc2[nH]1] |
| 5-(2-(cyclopentylamino)-6H-1,3,4-thiadiazin-5-yl)-1H-benzo[d]imidazol-2(3H)-one | 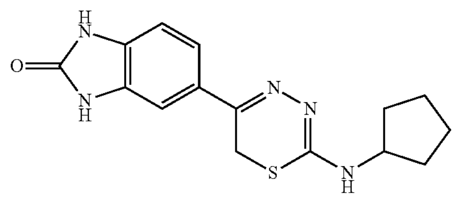 [SMILES: O=c1[nH]c2ccc(C3=NN=C(NC4CCCC4)SC3)cc2[nH]1] |
| 5-(2-(cyclobutylamino)-6H-1,3,4-thiadiazin-5-yl)-1H-benzo[d]imidazol-2(3H)-one | 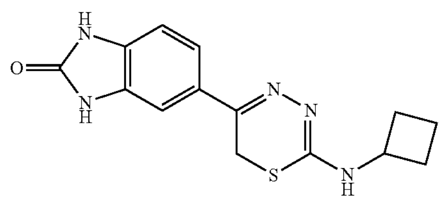 [SMILES: O=c1[nH]c2ccc(C3=NN=C(NC4CCC4)SC3)cc2[nH]1] |
| 5-(2-((cyclobutylmethyl)amino)-6H-1,3,4-thiadiazin-5-yl)-1H-benzo[d]imidazol-2(3H)-one | 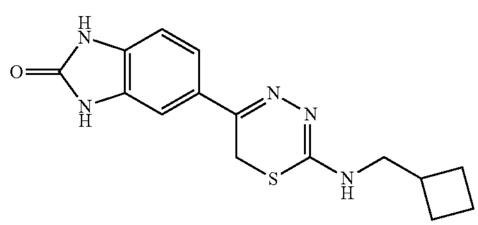 [SMILES: O=c1[nH]c2ccc(C3=NN=C(NCC4CCC4)SC3)cc2[nH]1] |
| 5-(2-((cyclopropylmethyl)amino)-6H-1,3,4-thiadiazin-5-yl)-1H-benzo[d]imidazol-2(3H)-one | 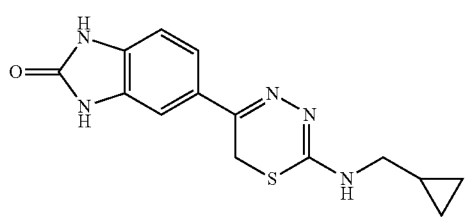 [SMILES: O=c1[nH]c2ccc(C3=NN=C(NCC4CC4)SC3)cc2[nH]1] |
| 5-(2-((cyclopentylmethyl)amino)-6H-1,3,4-thiadiazin-5-yl)-1H-benzo[d]imidazol-2(3H)-one | 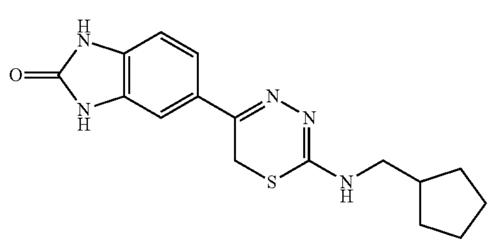 [SMILES: O=c1[nH]c2ccc(C3=NN=C(NCC4CCCC4)SC3)cc2[nH]1] |

TABLE 2-continued

Additional Thiadiazine Kinase Inhibitors

| Chemical Name | Structure |
| --- | --- |
| 5-(2-((2-cyclopentylethyl)amino)-6H-1,3,4-thiadiazin-5-yl)-1H-benzo[d]imidazol-2(3H)-one | 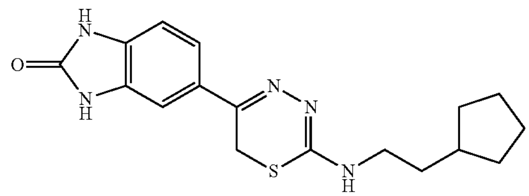 [SMILES: O=c1[nH]c2ccc(C3=NN=C(NCCC4CCCC4)SC3)cc2[nH]1] |
| 5-(2-((3-morpholinopropyl)amino)-6H-1,3,4-thiadiazin-5-yl)-1H-benzo[d]imidazol-2(3H)-one | 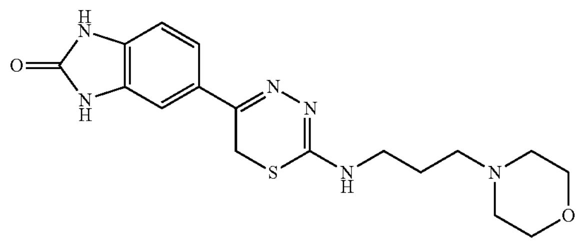 [SMILES: O=c1[nH]c2ccc(C3=NN=C(NCCCN4CCOCC4)SC3)cc2[nH]1] |
| 5-(2-((3-(dimethylamino)propyl)amino)-6H-1,3,4-thiadiazin-5-yl)-1H-benzo[d]imidazol-2(3H)-one | 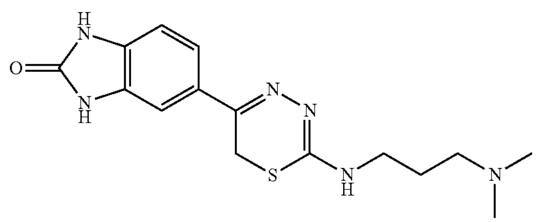 [SMILES: CN(C)CCCNC1=NN=C(c2ccc3[nH]c(=O)[nH]c3c2)CS1] |
| 5-(2-(((tetrahydrofuran-2-yl)methyl)amino)-6H-1,3,4-thiadiazin-5-yl)-1H-benzo[d]imidazol-2(3H)-one | 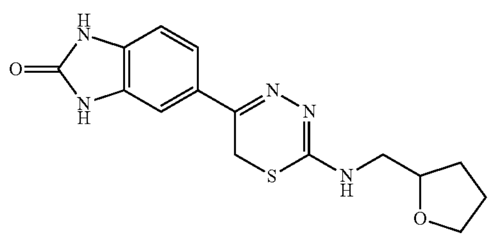 [SMILES: O=c1[nH]c2ccc(C3=NN=C(NCC4CCCO4)SC3)cc2[nH]1] |
| 5-(2-((2-(dimethylamino)ethyl)amino)-6H-1,3,4-thiadiazin-5-yl)-1H-benzo[d]imidazol-2(3H)-one | |
| 5-(2-((2-(dimethylamino)ethyl)amino)-6H-1,3,4-thiadiazin-5-yl)-1H-benzo[d]imidazol-2(3H)-one | |
| 5-(2-((2-(dimethylamino)ethyl)amino)-6H-1,3,4-thiadiazin-5-yl)-1H-benzo[d]imidazol-2(3H)-one | |

TABLE 2-continued

Additional Thiadiazine Kinase Inhibitors

| Chemical Name | Structure |
|---|---|
| 5-(2-((2-(dimethylamino)ethyl)amino)-6H-1,3,4-thiadiazin-5-yl)-1H-benzo[d]imidazol-2(3H)-one | 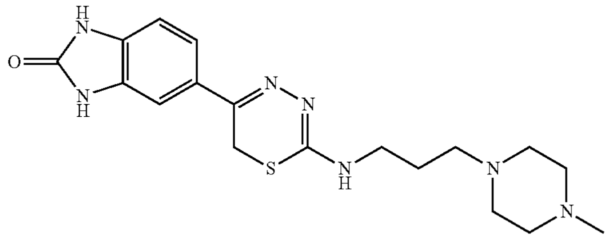 [SMILES: CN1CCN(CCCNC2=NN=C(c3ccc4[nH]c(=O)[nH]c4c3)CS2)CC1] |
| 5-(2-((2-(piperidin-1-yl)ethyl)amino)-6H-1,3,4-thiadiazin-5-yl)-1H-benzo[d]imidazol-2(3H)-one | 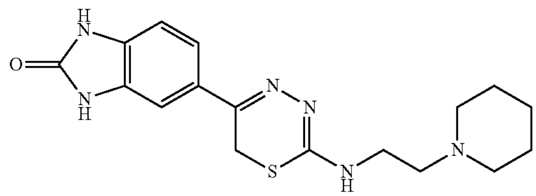 [SMILES: O=c1[nH]c2ccc(C3=NN=C(NCCN4CCCCC4)SC3)cc2[nH]1] |
| 5-(2-((2-methoxyethyl)amino)-6H-1,3,4-thiadiazin-5-yl)-1H-benzo[d]imidazol-2(3H)-one | 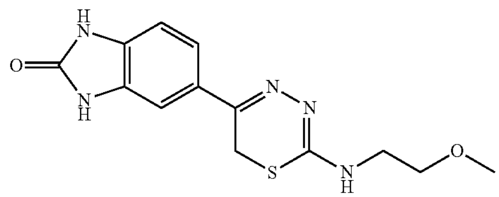 [SMILES: COCCNC1=NN=C(c2ccc3[nH]c(=O)[nH]c3c2)CS1] |
| 5-(2-((3-methoxypropyl)amino)-6H-1,3,4-thiadiazin-5-yl)-1H-benzo[d]imidazol-2(3H)-one | 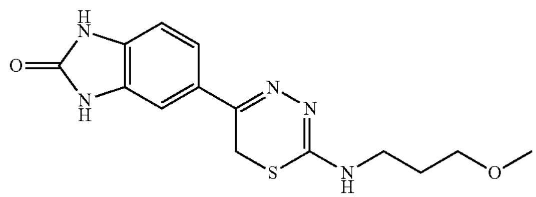 [SMILES: COCCCNC1=NN=C(c2ccc3[nH]c(=O)[nH]c3c2)CS1] |
| Methyl 1-methyl-2-oxo-2,3-dihydro-1H-benzo[d]imidazole-5-carboxylate | 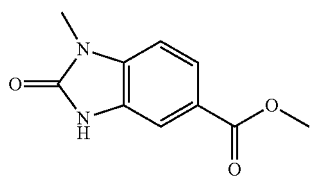 |
| Methyl 3-methyl-2-oxo-2,3-dihydro-1H-benzo[d]imidazole-5-carboxylate | 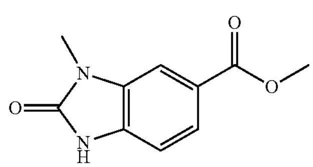 |
| N-methoxy-N,1-dimethyl-2-oxo-2,3-dihydro-1H-benzo[d]imidazole-5-carboxamide | 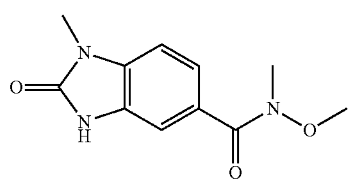 [SMILES: CON(C)C(=O)c1ccc2c(c1)[nH]c(=O)n2C] |
| N-methoxy-N,3-dimethyl-2-oxo-2,3-dihydro-1H-benzo[d]imidazole-5-carboxamide | 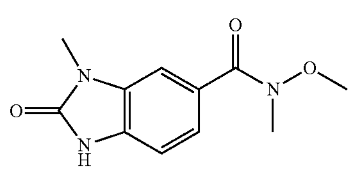 [SMILES: CON(C)C(=O)c1ccc2[nH]c(=O)n(C)c2c1] |

TABLE 2-continued

Additional Thiadiazine Kinase Inhibitors

| Chemical Name | Structure |
|---|---|
| 5-acetyl-1-methyl-1H-benzo[d]imidazol-2(3H)-one | 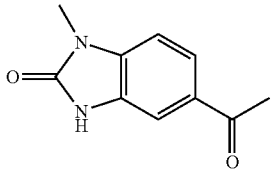 |
| 6-acetyl-1-methyl-1H-benzo[d]imidazol-2(3H)-one | 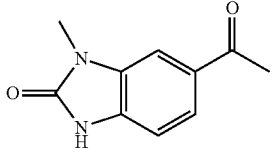 |
| 5-(2-bromoacetyl)-1-methyl-1H-benzo[d]imidazol-2(3H)-one | 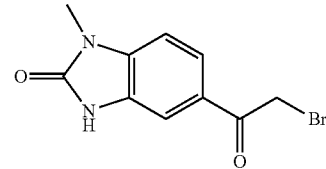 |
| 6-(2-bromoacetyl)-1-methyl-1H-benzo[d]imidazol-2(3H)-one | 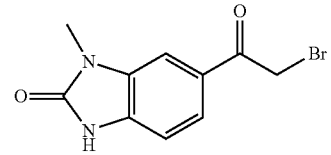 |
| N-methoxy-N,2-dimethyl-1H-benzo[d]imidazole-6-carboxamide | 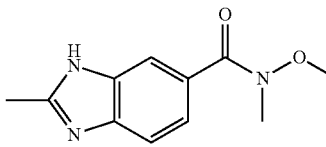 |
| 1-(2-methyl-1H-benzo[d]imidazol-6-yl)ethenone | 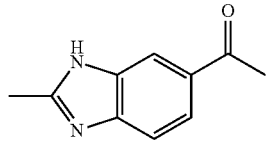 |
| 2-bromo-1-(2-methyl-1H-benzo[d]imidazol-6-yl)ethenone hydrobromide | 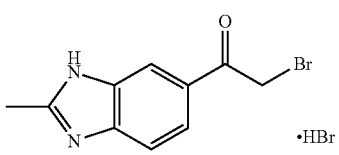 |
| 1-(1H-benzo[d]imidazol-6-yl)-2-bromoethanone hydrobromide | 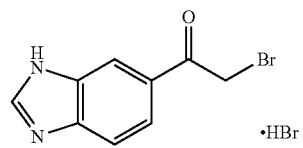 [SMILES: O=C(CBr)c1ccc2nc[nH]c2c1 ; Br] |

TABLE 2-continued

Additional Thiadiazine Kinase Inhibitors

| Chemical Name | Structure |
|---|---|
| 5-(2-((4-fluorobenzyl)amino)-6H-1,3,4-thiadiazin-5-yl)-1-methyl-1H-benzo[d]imidazol-2(3H)-one | 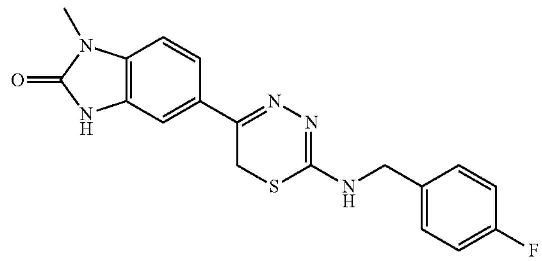 [SMILES: Cn1c(=O)[nH]c2cc(C3=NN=C(NCc4ccc(F)cc4)SC3)ccc21] |
| 5-(2-(benzylamino)-6H-1,3,4-thiadiazin-5-yl)-1-methyl-1H-benzo[d]imidazol-2(3H)-one | 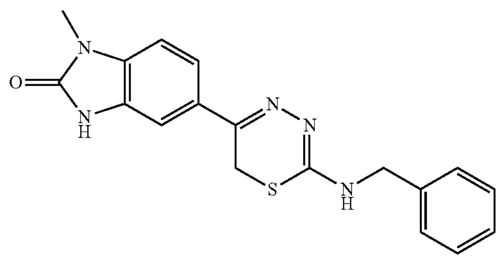 [SMILES: Cn1c(=O)[nH]c2cc(C3=NN=C(NCc4ccccc4)SC3)ccc21] |
| 6-(2-((4-fluorobenzyl)amino)-6H-1,3,4-thiadiazin-5-yl)-1-methyl-1H-benzo[d]imidazol-2(3H)-one | 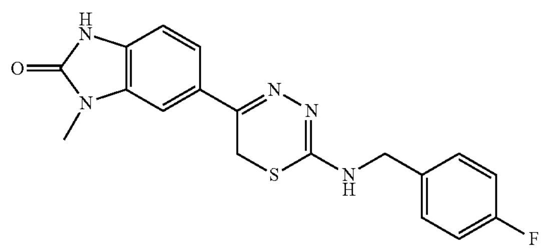 [SMILES: Cn1c(=O)[nH]c2ccc(C3=NN=C(NCc4ccc(F)cc4)SC3)cc21] |
| 6-(2-(benzylamino)-6H-1,3,4-thiadiazin-5-yl)-1-methyl-1H-benzo[d]imidazol-2(3H)-one | 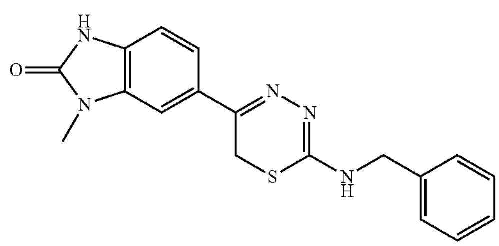 [SMILES: Cn1c(=O)[nH]c2ccc(C3=NN=C(NCc4ccccc4)SC3)cc21] |
| N-(4-fluorobenzyl)-5-(2-methyl-1H-benzo[d]imidazol-6-yl)-6H-1,3,4-thiadiazin-2-amine | 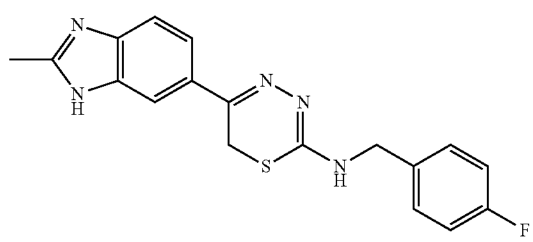 [SMILES: Cc1nc2ccc(C3=NN=C(NCc4ccc(F)cc4)SC3)cc2[nH]1] |
| N-benzyl-5-(2-methyl-1H-benzo[d]imidazol-6-yl)-6H-1,3,4-thiadiazin-2-amine | 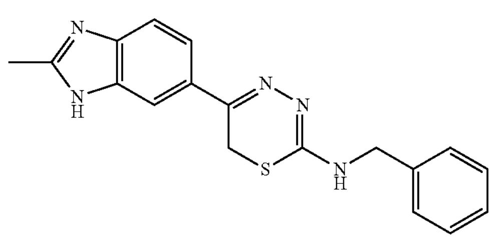 [SMILES: Cc1nc2ccc(C3=NN=C(NCc4ccccc4)SC3)cc2[nH]1] |

TABLE 2-continued

Additional Thiadiazine Kinase Inhibitors

| Chemical Name | Structure |
| --- | --- |
| 5-(1H-benzo[d]imidazol-6-yl)-N-(4-fluorobenzyl)-6H-1,3,4-thiadiazin-2-amine | 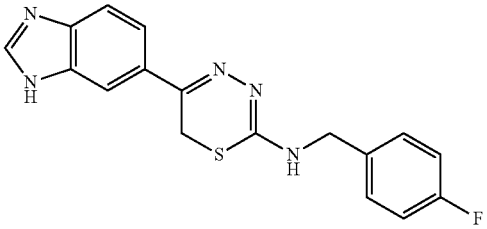 [SMILES: Fc1ccc(CNC2=NN=C(c3ccc4nc[nH]c4c3)CS2)cc1] |
| 5-(1H-benzo[d]imidazol-6-yl)-N-benzyl-6H-1,3,4-thiadiazin-2-amine | 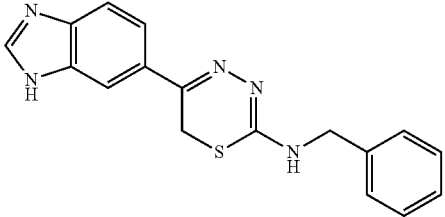 [SMILES: c1ccc(CNC2=NN=C(c3ccc4nc[nH]c4c3)CS2)cc1] |

As described supra, glucagon-like peptide-1 receptor agonists mimic the effects of the incretin hormone GLP-1, which is released from the intestine in response to food intake. Their effects include increasing insulin secretion, decreasing glucagon release, increasing satiety, and slowing gastric emptying.

Suitable GLP1R agonists for carrying out the disclosed methods include, without limitation, exenatide, liraglutide, exenatide LAR, taspoglutide, lixisenatide, albiglutide, dulaglutide, and semaglutide. Exenatide and Exenatide LAR are synthetic exendin-4 analogues obtained from the saliva of the *Heloderma suspectum* (lizard). Liraglutide is an acylated analogue of GLP-1 that self-associates into a heptameric structure that delays absorption from the subcutaneous injection site. Taspoglutide shares 3% homology with the native GLP-1 and is fully resistant to DPP-4 degradation. Lixisenatide is a human GLP1R agonist. Albiglutide is a long-acting GLP-1 mimetic, resistant to DPP-4 degradation. Dulaglutide is a long-acting GLP1 analogue. Semaglutide is a GLP1R agonist approved for the use of T2D. Clinically available GLP1R agonists include, e.g., exenatide, liraglutide, albiglutide, dulaglutide, lixisenatide, semaglutide.

In some embodiments, the GLP1R agonist is selected from the group consisting of GLP1(7-36), extendin-4, liraglutide, lixisenatide, semaglutide, and combinations thereof.

Additional suitable GLP1 agonists include, without limitation, disubstituted-7-aryl-5,5-bis(trifluoromethyl)-5,8-dihydropyrimido[4,5-d]pyrimidine-2,4(1H,3H)-dione compounds and derivatives thereof, e.g., 7-(4-Chlorophenyl)-1,3-dimethyl-5,5-bis(trifluoromethyl)-5,8-dihydropyrimido[4,5-d]pyrimidine-2,4(1H,3H)-dione (see, e.g., Nance et al., "Discovery of a Novel Series of Orally Bioavailable and CNS Penetrant Glucagon-like Peptide-1 Receptor (GLP-1R) Noncompetitive Antagonists Based on a 1,3-Disubstituted-7-aryl-5,5-bis(trifluoromethyl)-5,8-dihydropyrimido[4,5-d]pyrimidine-2,4(1H,3H)-dione Core," *J. Med. Chem.* 60:1611-1616 (2017), which is hereby incorporated by reference in its entirety).

Further suitable GLP1 agonists include positive allosteric modulators ("PAMS") of GLP1R, e.g., (S)-2-cyclopentyl-N-((1-isopropylpyrrolidin-2-yl)methyl)-10-methyl-1-oxo-1,2-dihydropyrazinoe-4-carboxamide; (R)-2-cyclopentyl-N-((1-isopropylpyrrolidin-2-yl)methyl)-10-methyl-1-oxo-1,2-dihydropyrazinoe-4-carboxamide; 2-cyclopentyl-N—(((S)-1-isopropylpyrrolidin-2-yl)methyl)-10-methyl-1-oxo-1,2,3,4-tetrahydropyrazino[1,2-a]indole-4-carboxamide; N—(((S)-1-isopropylpyrrolidin-2-yl)methyl)-10-methyl-1-oxo-2-((S)-tetrahydrofuran-3-yl)-1,2-dihydropyrazinoe-4-carboxamide; N—(((R)-1-isopropylpyrrolidin-2-yl)methyl)-10-methyl-1-oxo-2-((S)-tetrahydrofuran-3-yl)-1,2-dihydropyrazinoe-4-carboxamide; (S)-2-cyclopentyl-8-fluoro-N-((1-isopropylpyrrolidin-2-yl)methyl)-10-methyl-1-oxo-1,2-dihydropyrazino[1,2-a]indole-4-carboxamide; (R)-2-cyclopentyl-8-fluoro-N-((1-isopropylpyrrolidin-2-yl)methyl)-10-methyl-1-oxo-1,2-dihydropyrazino[1,2-a]indole-4-carboxamide; (R)-2-cyclopentyl-N—(((S)-1-isopropylpyrrolidin-2-yl)methyl)-10-methyl-1-oxo-1,2,3,4-tetrahydropyrazino[1,2-a]indole-4-carboxamide; (S)-2-cyclopentyl-N—(((S)-1-isopropylpyrrolidin-2-yl)methyl)-10-methyl-1-oxo-1,2,3,4-tetrahydropyrazinoe-4-carboxamide; (S)-10-chloro-2-cyclopentyl-N-((1-isopropylpyrrolidin-2-yl)methyl)-1-oxo-1,2-dihydropyrazino[1,2-a]indole-4-carboxamide; (R)-10-chloro-2-cyclopentyl-N-(1-isopropylpyrrolidin-2-yl)methyl)-1-oxo-1,2-dihydropyrazino[1,2-a]indole-4-carboxamide; (S)-10-bromo-2-cyclopentyl-N-((1-isopropylpyrrolidin-2-yl)methyl)-1-oxo-1,2-dihydropyrazino[1,2-a]indole-4-carboxamide; (R)-10-bromo-2-cyclopentyl-N-((1-isopropylpyrrolidin-2-yl)methyl)-1-oxo-1,2-dihydropyrazino[1,2-a]indole-4-carboxamide; (S)—N-((1-isopropylpyrrolidin-2-yl)methyl)-10-methyl-1-oxo-2-phenyl-1,2-dihydropyrazino[1,2-a]indole-4-carboxamide; (S)-10-cyano-2-cyclopentyl-N-((1-isopropylpyrrolidin-2-yl)methyl)-1-oxo-1,2-dihydropyrazino[1,2-a]indole-4-carboxamide; (S)-2-cyclopentyl-N-((1-isopropylpyrrolidin-2-yl)methyl)-1-oxo-10-vinyl-1,2-dihydropyrazino[1,2-a]indole-4-carboxamide; (S)—N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide; (R)—N-((1-isopropylpyrrolidin-2-yl)methyl)-10-methyl-2-(1-methyl-1H-pyrazol-4-yl)-1-oxo-1,2-dihydropyrazinoe-4-carboxamide; (S)—N-((1- isopropylpyrrolidin-2-yl)methyl)-10-methyl-1-oxo-2-(pyridin-3-yl)-1,2-dihydropyrazinoe-4-carboxamide; (R)—N-((1-isopropylpyrrolidin-2-yl)methyl)-10-methyl-1-oxo-2-(pyridin-3-yl)-1,2-dihydropyrazino[1,2-a]indole-4-carboxamide; N-(azetidin-2-ylmethyl)-2-cyclopentyl-10-methyl-1-oxo-1,2-dihydropyrazinoe-4-carboxamide; and 2-cyclopentyl-N-((1-isopropylazetidin-2-yl)methyl)-10-methyl-1-oxo-1,2-dihydropyrazino[1,2-a]indole-4-carboxamide; or pharmaceutically acceptable salts thereof (see PCT Publication No. WO 2017/117556, which is hereby incorporated by reference in its entirety).

In carrying out methods described herein, a population of pancreatic beta cells is contacted with a dual-specificity tyrosine phosphorylation-regulated kinase 1A (DYRK1A) inhibitor and a glucagon-like peptide-1 receptor (GLP1R) agonist.

Contacting a population of pancreatic beta cells with a dual-specificity tyrosine phosphorylation-regulated kinase 1A (DYRK1A) inhibitor and a glucagon-like peptide-1 receptor (GLP1R) agonist may be carried out with harmine and GLP1(7-36).

Contacting a population of pancreatic beta cells with a dual-specificity tyrosine phosphorylation-regulated kinase 1A (DYRK1A) inhibitor and a glucagon-like peptide-1 receptor (GLP1R) agonist may be carried out with harmine and N-(4-fluorobenzyl)-5-(benzo[d]imidazol-2(3H)-one)-6H-1,3,4-thiadiazin-2-amine.

Contacting a population of pancreatic beta cells with a dual-specificity tyrosine phosphorylation-regulated kinase 1A (DYRK1A) inhibitor and a glucagon-like peptide-1 receptor (GLP1R) agonist may be carried out with a single composition comprising both the DYRK1A inhibitor and the GLP1R agonist. Alternatively, contacting a population of pancreatic beta cells with a dual-specificity tyrosine phosphorylation-regulated kinase 1A (DYRK1A) inhibitor and a glucagon-like peptide-1 receptor (GLP1R) agonist may be carried out serially. For example, a population of pancreatic beta cells may first be contacted with a dual-specificity tyrosine phosphorylation-regulated kinase 1A (DYRK1A) inhibitor (or a compositions comprising the dual-specificity tyrosine phosphorylation-regulated kinase 1A (DYRK1A) inhibitor) and then a glucagon-like peptide-1 receptor (GLP1R) agonist (or a compositions comprising the glucagon-like peptide-1 receptor (GLP1R) agonist), or first with a glucagon-like peptide-1 receptor (GLP1R) agonist (or composition thereof) and then a dual-specificity tyrosine phosphorylation-regulated kinase 1A (DYRK1A) inhibitor (or composition thereof).

In carrying out methods described herein, contacting a population of pancreatic beta cells with a dual-specificity tyrosine phosphorylation-regulated kinase 1A (DYRK1A) inhibitor and a glucagon-like peptide-1 receptor (GLP1R) agonist may occur multiple times a day, daily, weekly, twice weekly, monthly, bi-monthly, annually, semi-annually, or any amount of time there between. The DYRK1A inhibitor and the glucagon-like peptide-1 receptor (GLP1R) agonist may be administered at different administration frequencies. Contacting a population of pancreatic beta cells with a DYRK1A inhibitor and a GLP1R agonist may occur acutely or chronically. For example, contacting may occur chronically over a period of 1 year, 2 years, 3 years, 4 years, or more. In some embodiments, administering is carried out infrequently.

Contacting a population of pancreatic beta cells with a dual-specificity tyrosine phosphorylation-regulated kinase 1A (DYRK1A) inhibitor and a glucagon-like peptide-1 receptor (GLP1R) agonist may be carried out to increase the number of proliferating pancreatic beta cells in the population by at least about 4%, 5%, 6%, 7%, 8%, 9%, 10%, or more.

Contacting a population of pancreatic beta cells with a dual-specificity tyrosine phosphorylation-regulated kinase 1A (DYRK1A) inhibitor and a glucagon-like peptide-1 receptor (GLP1R) agonist may be carried out to increase the number of proliferating pancreatic beta cells in a population by about 4-10% per day, or about 4-6% per day, 5-7% per day, 6-9% per day, or 7-10% per day.

Contacting a population of pancreatic beta cells with a dual-specificity tyrosine phosphorylation-regulated kinase 1A (DYRK1A) inhibitor and a glucagon-like peptide-1 receptor (GLP1R) agonist may increase the number of proliferating pancreatic beta cells in a population by about 6-10% per day.

Methods of contacting a population of pancreatic beta cells with a dual-specificity tyrosine phosphorylation-regulated kinase 1A (DYRK1A) inhibitor and a glucagon-like peptide-1 receptor (GLP1R) agonist may be carried out under conditions effective to cause a synergistic increase in cell proliferation in a population of pancreatic beta cells, which means, inter alia, an increase in the number of proliferating pancreatic beta cells in the population as compared to when the cells are contacted with a DYRK1A inhibitor or a GLP1R agonist alone, or when the cells are not contacted by either a DYRK1A inhibitor or a GLP1R agonist.

In carrying out this and other methods, contacting a population of pancreatic beta cells with a dual-specificity tyrosine phosphorylation-regulated kinase 1A (DYRK1A) inhibitor and a glucagon-like peptide-1 receptor (GLP1R) agonist may not induce beta cell death or DNA damage in the population of cells. Moreover, contacting may induce beta cell differentiation and increase glucose-stimulated insulin secretion.

The method may be carried out to enhance cell survival. For example, the method may be carried out to enhance cell survival of a treated population of pancreatic beta cells relative to an untreated population of pancreatic beta cells. Alternatively, the method may be carried out to decrease cell death or apoptosis of a contacted population of pancreatic beta cells relative to an uncontacted population of pancreatic beta cells.

Another aspect relates to a method of treating a subject for a condition associated with insufficient insulin secretion. This method involves administering to a subject in need of treatment for a condition associated with an insufficient level of insulin secretion a dual-specificity tyrosine phosphorylation-regulated kinase 1A (DYRK1A) inhibitor and a glucagon-like peptide-1 receptor (GLP1R) agonist, where the administering is carried out under conditions effective to cause a synergistic increase in pancreatic beta cell mass in the subject to treat the subject for an insufficient level of insulin secretion.

Another aspect of the disclosure relates to a method of treating a subject for a condition associated with insufficient insulin secretion. This method involves administering to a subject in need of treatment for a condition associated with an insufficient level of insulin secretion a dual-specificity tyrosine phosphorylation-regulated kinase 1A (DYRK1A) inhibitor and a dipeptidylpeptidase IV (DPP4) inhibitor, where the administering is carried out under conditions effective to cause a synergistic increase in pancreatic beta cell mass in the subject to treat the subject for an insufficient level of insulin secretion.

As used herein, a condition associated with an insufficient level of insulin secretion means a condition where a subject produces a lower plasma level of insulin than is required to maintain normal glucose levels in the blood such that the subject with the condition associated with insufficient insulin secretion becomes hyperglycemic. In such a condition, the pancreatic beta cells of the afflicted subject secrete an insufficient level of insulin to maintain the presence of a normal concentration of glucose in the blood (i.e., normoglycemica).

One of the conditions associated with an insufficient level of insulin secretion is insulin resistance. Insulin resistance is a condition in which a subject's cells become less sensitive to the glucose-lowering effects of insulin. Insulin resistance in muscle and fat cells reduces glucose uptake (and, therefore, local storage of glucose as glycogen and triglycerides), whereas insulin resistance in liver cells results in reduced glycogen synthesis and storage and a failure to suppress glucose production and release into the blood. Insulin resistance normally refers to reduced glucose-lowering effects of insulin. However, other functions of insulin can also be affected. For example, insulin resistance in fat cells reduces the normal effects of insulin on lipids and results in reduced uptake of circulating lipids and increased hydrolysis of stored triglycerides. Increased mobilization of stored lipids in these cells elevates free fatty acids in the blood plasma. Elevated blood fatty-acid concentrations, reduced muscle glucose uptake, and increased liver glucose production all contribute to elevated blood glucose levels. If insulin resistance exists, more insulin needs to be secreted by the pancreas. If this compensatory increase does not occur, blood glucose concentrations increase and type II diabetes occurs.

One of the conditions associated with an insufficient level of insulin secretion is diabetes. Diabetes can be divided into two broad types of diseases: Type I ("T1D") and Type II ("T2D"). The term "diabetes" also refers herein to a group of metabolic diseases in which patients have high blood glucose levels, including Type I diabetes, Type II diabetes, gestational diabetes, congenital diabetes, maturity onset diabetes ("MODY"), cystic fibrosis-related diabetes, hemochromatosis-related diabetes, drug-induced diabetes (e.g., steroid diabetes), and several forms of monogenic diabetes.

In certain embodiments, the subject has or is being treated for one or more of Type I diabetes (T1D), Type II diabetes (T2D), gestational diabetes, congenital diabetes, maturity onset diabetes (MODY), cystic fibrosis-related diabetes, hemochromatosis-related diabetes, drug-induced diabetes, or monogenic diabetes. For example, the subject has or is being treated for Type I diabetes. Or, the subject has or is being treated for Type II diabetes.

The condition associated with an insufficient level of insulin secretion is metabolic syndrome. Metabolic syndrome is generally used to define a constellation of abnormalities that is associated with increased risk for the development of type II diabetes and atherosclerotic vascular disease. Related conditions and symptoms include, but are not limited to, fasting hyperglycemia (diabetes mellitus type II or impaired fasting glucose, impaired glucose tolerance, or insulin resistance); high blood pressure; central obesity (also known as visceral, male-pattern or apple-shaped adiposity), meaning overweight with fat deposits mainly around the waist; decreased HDL cholesterol; and elevated triglycerides.

The condition associated with an insufficient level of insulin secretion may be metabolic syndrome or insulin resistance. Thus, the method may be carried out to treat a subject having or being treated for metabolic syndrome or insulin resistance.

Other conditions that may be associated with an insufficient level of insulin secretion include, without limitation, hyperuricemia, fatty liver (especially in concurrent obesity) progressing to non-alcoholic fatty liver disease, polycystic ovarian syndrome (in women), and acanthosis nigricans.

Related disorders may also be treated pursuant to the treatment methods disclosed herein including, without limitation, any disease associated with a blood or plasma glucose level outside the normal range, such as hyperglycemia. Consequently, the term "related disorders" includes impaired glucose tolerance ("IGT"), impaired fasting glucose ("IFG"), insulin resistance, metabolic syndrome, postprandial hyperglycemia, and overweight/obesity. Such related disorders can also be characterized by an abnormal blood and/or plasma insulin level.

The methods may be carried out to treat a subject with conditions associated with beta cell failure or deficiency. Such conditions include, without limitation, Type I diabetes (T1D), Type II diabetes (T2D), gestational diabetes, congenital diabetes, maturity onset diabetes (MODY), cystic fibrosis-related diabetes, hemochromatosis-related diabetes, drug-induced diabetes, or monogenic diabetes. Drug induced diabetes relates to a condition that is caused through the use of drugs that are toxic to beta cells (e.g., steroids, antidepressants, second generation antipsychotics, and immunosuppressives). Exemplary immunosuppressive drugs include, but are not limited to, members of the cortisone family (e.g., prednisone and dexamethasome), rapamycin/sirolimus, everolimus, and calciuneurin inhibitors (e.g., FK-506/tacrolimus).

Additional conditions associated with beta cell deficiency include, without limitation, hypoglycemia unawareness, labile insulin dependent diabetes, pancreatectomy, partial pancreatectomy, pancreas transplantation, pancreatic islet allotransplantation, pancreatic islet autotransplantation, and pancreatic islet xenotransplantation.

As used herein, hypoglycemia unawareness is a complication of diabetes in which the patient is unaware of a deep drop in blood sugar because it fails to trigger the secretion of epinephrine which generates the characteristic symptoms of hyperglycemia (e.g., palpitations, sweating, anxiety) that serve to warn the patient of the dropping blood glucose.

Pancrease transplantation may occur alone, after, or in combination with kidney transplantation. For example, pancreas transplantation alone may be considered medically necessary in patients with severely disabling and potentially life-threatening complications due to hypoglycemia unawareness and labile insulin dependent diabetes that persists in spite of optimal medical management. Pancreas transplantation following prior kidney transplantation may occur in a patient with insulin dependent diabetes. Pancreas transplantation may occur in combination with kidney transplantation in an insulin dependent diabetic patient with uremia. Pancreas retransplantation may be considered after a failed primary pancreas transplant.

As used herein, pancreatic islet transplantation is a procedure in which only the islets of Langerhans, which contain the endocrine cells of the pancreas, including the insulin producing beta cells and glucagon producing alpha cells, are isolated and transplanted into a patient. Pancreatic islet allotransplantation occurs when islets of Langerhans are isolated from one or more human donor pancreas. Pancreatic islet cells may also be derived from human embryonic stem cells or induced pluripotent stem cells. Pancreatic islet xenotransplantation occurs when islets of Langerhans are isolated from one or more non-human pancreas (e.g., a porcine pancreas or primate pancreas). Pancreatic islet autotransplantation occurs when islets of Langerhans are isolated from the pancreas of a patient undergoing pancreatectomy (e.g., for chronic pancreatitis from gall stone, drugs, and/or familial genetic causes) and returned to the same patient via infusion into the portal vein, via laparoscopy to the omentum, via endoscopy to the gastric wall, or subcutaneously via minor incision. As with pancreas transplantation, pancreatic islet transplantation can be performed alone, after, or in combination with kidney transplantation. For example, pancreatic islet transplantation may occur alone to restore hypoglycemia awareness, provide glycemic control, and/or protect a patient from severe hypoglycemic events (Hering et al., "Phase 3 Trial of Transplantation of Human Islets in Type 1 Diabetes Complicated by Severe Hypoglycemia," *Diabetes Care* 39(7):1230-1240 (2016), which is hereby incorporated by reference in its entirety).

Pancreatic islet transplantation may occur in combination with total pancreatectomy. For example, pancreatic islet transplantation may be performed after total pancreatectomy to prevent or ameliorate surgically induced diabetes by preserving β cell function (Johnston et al., "Factors Associated With Islet Yield and Insulin Independence After Total Pancreatectomy and Islet Cell Autotransplantation in Patients With Chronic Pancreatitis Utilizing Off-site Islet Isolation: Cleveland Clinic Experience," *J. Chem. Endocrinol. Metab.* 100(5):1765-1770 (2015), which is hereby incorporated by reference in its entirety). Thus, pancreatic islet transplantation may provide sustained long-term insulin-independence.

In some embodiments, pancreatic islet transplantation may occur in combination with the administration of immunosuppressive agents. Suitable immunosuppressive agents include, but are not limited to, daclizumab (Zenapax; Roche), low-dose rapamycin (sirolimus), and FK506 (tacrolimus) (Van Belle et al., "Immunosuppression in Islet Transplantation," *J. Clin. Invest.* 118(5):1625-1628 (2008), which is hereby incorporated by reference in its entirety).

In some embodiments, pancreatic islet transplantation occurs in the context of an encapsulation device to protect the transplanted pancreatic islet cells from the host autoimmune response, while allowing glucose and nutrients to reach the transplanted pancreatic islet cells.

The methods described herein may be carried out to enhance pancreas, pancreatic islet allotransplantation, pancreatic islet autotransplantation, pancreatic islet xenotransplantation by regenerating pancreatic β cells in a patient. For example, the methods of the present application may be used to prevent or ameliorate surgically induced diabetes by preserving β cell function, restore hypoglycemia awareness, provide glycemic control, and/or protect a patient from severe hypoglycemic events. Thus, another aspect of the disclosure relates to a method of regenerating pancreatic beta cells in a transplant patient. This method involves administering to a transplant patient a dual-specificity tyrosine phosphorylation-regulated kinase 1A (DYRK1A) inhibitor and a glucagon-like peptide-1 receptor (GLP1R) agonist, wherein said administering is carried out under conditions effective to cause a synergistic increase in pancreatic beta cell mass in the transplant patient to regenerate pancreatic beta cells in the patient.

The methods may be carried out to treat a subject at risk of developing Type II Diabetes. A patient at risk of developing Type II Diabetes may have pre-diabetes/metabolic syndrome.

A patient at risk of developing Type II Diabetes may have been treated with a psychoactive drug including, but not limited to, a selective serotonin reuptake inhibitor ("SSRI") for depression, obsessive compulsive disorder ("OCD"), etc.

The subject may be a mammalian subject, for example, a human subject. Suitable human subjects include, without limitation, children, adults, and elderly subjects having a beta-cell and/or insulin deficiency.

The subject may also be non-human, such as bovine, ovine, porcine, feline, equine, murine, canine, lapine, etc.

Administering to a subject a dual-specificity tyrosine phosphorylation-regulated kinase 1A (DYRK1A) inhibitor and a glucagon-like peptide-1 receptor (GLP1R) agonist may increase the number of proliferating pancreatic beta cells in the subject by at least about 4%, 5%, 6%, 7%, 8%, 9%, 10%, or more.

Administering to a subject a dual-specificity tyrosine phosphorylation-regulated kinase 1A (DYRK1A) inhibitor and a glucagon-like peptide-1 receptor (GLP1R) agonist may increase the number of proliferating pancreatic beta cells in a subject by about 4-10% per day, or about 4-6% per day, 5-7% per day, 6-9% per day, or 7-10% per day.

Administering to a subject a dual-specificity tyrosine phosphorylation-regulated kinase 1A (DYRK1A) inhibitor and a glucagon-like peptide-1 receptor (GLP1R) agonist may increase the number of proliferating pancreatic beta cells in the subject by about 6-10% per day.

Administering to a subject a dual-specificity tyrosine phosphorylation-regulated kinase 1A (DYRK1A) inhibitor and a glucagon-like peptide-1 receptor (GLP1R) agonist may increase glucose-stimulated insulin secretion in pancreatic beta cells of the subject (e.g., compared to a subject not administered a dual-specificity tyrosine phosphorylation-regulated kinase 1A (DYRK1A) inhibitor and a glucagon-like peptide-1 receptor (GLP1R) agonist).

The DYRK1A inhibitor may be selected from the group consisting of harmine, INDY, leucettine-41, 5-iodotubercidin (5-IT), GNF4877, CC-401, thiadiazine kinase inhibitors, and combinations thereof. Exemplary DYRK1A inhibitors are described in detail supra.

The GLP1R agonist may be selected from the group consisting of GLP1 analogs, extendin-4, liraglutide, lixisenatide, semaglutide, and combinations thereof, which are described supra.

Administering to a subject a dual-specificity tyrosine phosphorylation-regulated kinase 1A (DYRK1A) inhibitor and a glucagon-like peptide-1 receptor (GLP1R) agonist may be carried out with harmine and GLP1(7-36).

Administering to a subject a dual-specificity tyrosine phosphorylation-regulated kinase 1A (DYRK1A) inhibitor and a glucagon-like peptide-1 receptor (GLP1R) agonist may be carried out with harmine and N-(4-fluorobenzyl)-5-(benzo[d]imidazol-2(3H)-one)-6H-1,3,4-thiadiazin-2-amine.

Administering to a subject a dual-specificity tyrosine phosphorylation-regulated kinase 1A (DYRK1A) inhibitor and a glucagon-like peptide-1 receptor (GLP1R) agonist may be carried out by administering a single composition comprising both the DYRK1A inhibitor and the GLP1R agonist. Alternatively, administering to a subject a dual-specificity tyrosine phosphorylation-regulated kinase 1A (DYRK1A) inhibitor and a glucagon-like peptide-1 receptor (GLP1R) agonist may be carried out serially. For example, a subject may first be administered a dual-specificity tyrosine phosphorylation-regulated kinase 1A (DYRK1A) inhibitor (or a compositions comprising the dual-specificity tyrosine phosphorylation-regulated kinase 1A (DYRK1A)

inhibitor) and then a glucagon-like peptide-1 receptor (GLP1R) agonist (or a compositions comprising the glucagon-like peptide-1 receptor (GLP1R) agonist), or first with a glucagon-like peptide-1 receptor (GLP1R) agonist (or composition thereof) and then a dual-specificity tyrosine phosphorylation-regulated kinase 1A (DYRK1A) inhibitor (or composition thereof).

Administering may occur multiple times each day, daily, weekly, twice weekly, monthly, bi-monthly, annually, semi-annually, or any amount of time there between. The DYRK1A inhibitor and the glucagon-like peptide-1 receptor (GLP1R) agonist may be administered at different administration frequencies. In some embodiments, administering is carried out acutely or chronically. For example, administering may be carried out chronically over a period of 1 year, 2 years, 3, years, 4 years, or more. In some embodiments, administering is carried out infrequently. As used herein, the term "treating" is meant preventive, or improved or curative treatment. In other words, treatment methods may be carried out to prevent a subject from getting a condition associated with insufficient insulin secretion or from a subject's condition associated with insufficient insulin secretion getting worse. Alternatively, the treatment method is carried out to improve a subject's condition associated with insufficient insulin secretion, or to fully cure the condition (i.e., such that the subject no longer has a condition associated with an insufficient level of insulin secretion as judged by a competent health care professional).

The term "treating" means the correction, decrease in the rate of change, or reduction of an impaired glucose homeostasis in a subject. The level of glucose in blood fluctuates throughout the day. Glucose levels are usually lower in the morning, before the first meal of the day and rise after meals for some hours. Consequently, the term "treating" includes controlling blood glucose level in a subject by increasing or decreasing the subject's blood glucose level. This may depend on many factors, including the condition of the subject and/or the particular time of day, as blood glucose levels fluctuate throughout the day.

"Treating" means regulating a temporary or persistent reduction of blood glucose level in a subject having diabetes or a related disorder. The term "treating" may also mean improving insulin release (e.g., by pancreatic beta cells) in a subject.

It may be desirable to modulate blood glucose levels in a subject to normalize or regulate the blood or plasma glucose level in a subject having abnormal levels (i.e., levels that are below or above a known reference, median, or average value for a corresponding subject with a normal glucose homeostasis). The treatment method of the present invention may be carried out to achieve such effects.

In carrying out treatment methods, administering of a dual-specificity tyrosine phosphorylation-regulated kinase 1A (DYRK1A) inhibitor and a glucagon-like peptide-1 receptor (GLP1R) agonist to a subject may involve administering a pharmaceutical composition comprising the dual-specificity tyrosine phosphorylation-regulated kinase 1A (DYRK1A) inhibitor or the glucagon-like peptide-1 receptor (GLP1R) agonist, or both, in therapeutically effective amounts, which means an amount of the DYRK1A inhibitor and the GLP1R agonist effective to treat the stated conditions and/or disorders in the subject. Such amounts generally vary according to a number of factors well within the purview of a person of ordinary skill in the art. These include, without limitation, the particular subject's general health, age, weight, height, general physical condition, medical history, the particular compound used, as well as the carrier in which it is formulated, and the route of administration selected for it, the length or duration of treatment, and the nature and severity of the condition being treated.

Administering typically involves administering pharmaceutically acceptable dosage forms, which means dosage forms of compounds described herein and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in *Remington's Pharmaceutical Sciences*, Mack Publishing Co., Easton, Pa., latest edition, which is hereby incorporated by reference in its entirety.

In carrying out treatment methods, the DYRK1A inhibitor and the GLP1R agonist may be contained, in any appropriate amount, in any suitable carrier substance. DYRK1A inhibitors and the GLP1R agonists may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

Pharmaceutical compositions may be formulated to release the active DYRK1A inhibitor and the GLP1R agonist substantially immediately upon administration or at any predetermined time or time period after administration.

Controlled release formulations include (i) formulations that create a substantially constant concentration of the drug(s) within the body over an extended period of time; (ii) formulations that after a predetermined lag time create a substantially constant concentration of the drug(s) within the body over an extended period of time; (iii) formulations that sustain drug(s) action during a predetermined time period by maintaining a relatively, constant, effective drug level in the body with concomitant minimization of undesirable side effects associated with fluctuations in the plasma level of the active drug substance; (iv) formulations that localize drug(s) action by, e.g., spatial placement of a controlled release composition adjacent to or in the diseased tissue or organ; and (v) formulations that target drug(s) action by using carriers or chemical derivatives to deliver the drug to a particular target cell type.

Administration of DYRK1A inhibitor(s) and GLP1R agonist(s) in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index ("TI") is defined as the ratio of median lethal dose ($LD_{50}$) to median effective dose ($ED_{50}$)); (ii) a narrow absorption window in the gastro-intestinal tract; or (iii) a very short biological half-life so that frequent dosing during a day is required in order to sustain the plasma level at a therapeutic level.

Any of a number of strategies can be pursued to obtain controlled release in which the rate of release outweighs the rate of metabolism of the DYRK1A inhibitor and/or the GLP1R agonist in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes). Thus, administering may be carried out nasally, orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Compounds may be administered alone or with suitable pharmaceutical carriers, and can be in solid or liquid form, such as tablets, capsules, powders, solutions, suspensions, or emulsions. In certain embodiments, administering is carried out nasally, orally, transdermally, parenterally, subcutaneously, intravenously, intramuscularly, or intraperitoneally.

In certain embodiments, the administering is carried out using an infusion pump to provide, e.g., rate controlled infusion, periodic infusion, and/or bolus dosage infusion. The infusion pump may be a stationary or ambulatory infusion pump. Stationary infusion pumps are used primarily at a patient's bedside. Ambulatory infusion pumps are relatively small, at least substantially self-contained devices that are used to introduce drugs and other infusible substances (e.g., insulin) to a selected subject. Some ambulatory infusion pumps are configured to be worn on a belt, carried in a clothing pocket, or otherwise supported within a holder of some kind (collectively referred to as "pocket pumps"). Other infusion pumps are configured to adhere to the skin in a patch-like fashion (referred to as "patch pumps"). Infusion pumps may be used, for example, to intravenously or subcutaneously introduce (or "infuse") medicament on an ongoing or even continuous basis outside of a clinical environment. Infusion pumps greatly reduce the frequency of subcutaneous access events such as needle-based shots. In certain embodiments, the infusion pump is a subcutaneous or intravenous infusion pump. For example, the infusion pump may be an ambulatory subcutaneous insulin infusion pump.

A further aspect relates to a composition comprising a dual-specificity tyrosine phosphorylation-regulated kinase 1A (DYRK1A) inhibitor and a glucagon-like peptide-1 receptor (GLP1R) agonist.

Suitable DYRK1A inhibitors are described supra and include, e.g., harmine, INDY, leucettine-41, 5-iodotubercidin (5-IT), GNF4877, CC-401, kinase inhibitors, and derivatives thereof.

Suitable GLP1R agonists are described supra and include, e.g., extendin-4, liraglutide, lixisenatide, semaglutide, and derivatives thereof.

The composition may further comprise a carrier. Suitable carriers are described supra. The carrier may be a pharmaceutically-acceptable carrier. Suitable pharmaceutically-acceptable carriers are described supra.

Another aspect relates to a method of increasing cell proliferation in a population of pancreatic beta cells. This method involves contacting a population of pancreatic beta cells with a dual-specificity tyrosine phosphorylation-regulated kinase 1A (DYRK1A) inhibitor and a compound that increases cAMP, where said contacting is carried out under conditions effective to cause a synergistic increase in cell proliferation in the population of pancreatic beta cells.

Another aspect of the disclosure relates to a method of treating a subject for a condition associated with insufficient insulin secretion. This method involves administering to a subject in need of treatment for a condition associated with an insufficient level of insulin secretion a dual-specificity tyrosine phosphorylation-regulated kinase 1A (DYRK1A) inhibitor and a compound that increases cAMP, where the administering is carried out under conditions effective to cause a synergistic increase in pancreatic beta cell mass in the subject to treat the subject for an insufficient level of insulin secretion.

A further aspect of the disclosure relates to a composition comprising a dual-specificity tyrosine phosphorylation-regulated kinase 1A (DYRK1A) inhibitor and a compound that increases cAMP.

Cyclic adenosine monophosphate (cAMP) is an intracellular second messenger that regulates β-cell replication. In some embodiments, the compounds that increase cAMP for carrying out the disclosed methods include cAMP analogues, including dibutyrl-cAMP and/or 8-chloro-cAMP. Increasing cAMP has been shown to increase beta cell replication in juvenile rodents (Zhao et al., "Repurposing cAMP-Modulating Medications to Promote β-Cell Replication," *Mol. Endocrinol.* 28(10):1682-1697 (2014), which is hereby incorporated by reference in its entirety). However, as shown in FIGS. 5A-5H, the administration of agents that increase cAMP has no effect on human beta cell proliferation unless the administration occurs in combination with a DYRK1 inhibitor (e.g., harmine). Thus, the present disclosure is the first to demonstrate that increasing cAMP in combination with a DYRK1A inhibitor synergistically increases human beta cell proliferation.

The intracellular levels of cAMP are regulated by the balance between the activities of two enzymes: adenylyl cyclase ("AC") and cyclic nucleoside phosphodiesterase (PDE). Most ACs are activated downstream from G-protein coupled receptors (GPCRs) such as the β adrenoreceptor by interactions with the a subunit of $G_s$ protein ($\alpha_s$), which is released from heterotrimeric αβγ G-protein complexes following binding of agonist ligands to GPCRs (e.g., epinephrine in the case of β adrenoceptors) and binds to and activates AC (Sassone-Corsi, "The Cyclic AMP Pathway," *Cold Spring Harb. Perspect. Biol.* 4(12) (2012), which is hereby incorporated by reference in its entirety).

β adrenoreceptors are divided into $β_1$, $β_2$, and $β_3$ subtypes, each of which are coupled to $G_s$ proteins. Activation of $β_2$ adrenoreceptors on β-cells increases intracellular cAMP. Thus, in certain embodiments, compounds that increase cAMP for carrying out the disclosed methods include $β_2$ adrenoreceptor agonists. Suitable $β_2$ adrenoreceptor agonists include, but are not limited to, epinephrine, albuterol (salbutamol), bitolterol mesylate, formoterol, isoprenaline, levalbuterol, metaproterenol, salmeterol, terbutaline, and/or ritodrine.

A variety of GPCRs promote β-cell replication by activating cAMP-dependent signalling pathways and intracellular levels of cAMP. In certain embodiments, compounds that increase intracellular cAMP levels are ligands for GPCRs. Suitable (and non-limiting) agonists for increasing cAMP levels are listed in Table 3 below.

TABLE 3

Exemplary GPCRs, Ligands, and Agonists

| GPCR | Full Name | Ligand | Agonist | Alpha Subunit |
|---|---|---|---|---|
| GLP1R | Glucagon-like Peptide 1 | glucagon-like peptide 1 | GLP1 analogs, extendin-4, liraglutide lixisenatide, semaglutide, SAR425899, MED10382 | $G_s$ |
| GPR119 | G-protein receptor119 | free fatty acids | DS-8500a, MK-8282 | $G_s$ |
| PTH1 | Parathyroid hormone receptor 1 | PTH, PTHrP | AH-3960 | $G_s$ |
| $A_{2A}$ AR | A2A Adenosine Receptor | Adenosine | Regedenoson, NECA, CGS-21680, CV-3146, binodenoson, zeatin riboside, limonene, ATL-146e, YT-146, DPMA, UK-432,097 | $G_s$ |
| $A_{2B}$ AR | A2B Adenosine Receptor | Adenosine | BAY 60-6583, NECA, (S)-PHPNECA, LUF-5835, LUF-5845 | $G_s$ |

Additional GPCRs are described in Amisten et al., "An Atlas and Functional Analysis of G-Protein Coupled Receptors in Human Islets of Langerhans," *Pharmacol. Ther.* 139(3):359-391 (2013), which is hereby incorporated by reference in its entirety, and which identifies 293 GPCRs present in the Human islet.

Norepinephrine functions as a physiologic suppressor of cAMP synthesis in β-cells and impairs β-cell activation via activation of $\alpha_2$ adrenergic receptors (Zhao et al., "Repurposing cAMP-Modulating Medications to Promote β-Cell Replication," *Mol. Endocrinol.* 28(10):1682-1697 (2014), which is hereby incorporated by reference in its entirety). Thus, inhibition of $\alpha_2$ adrenergic receptors increases intracellular cAMP levels. In certain embodiments, compounds that increase cAMP for carrying out the disclosed methods include $\alpha_z$ adrenergic receptor antagonists including, but not limited to, mirtazapine.

PDEs catalyze the hydrolysis of cAMP. In humans, there are 21 PDE genes that comprise 11 structurally related families (PDE1-11). B-cells express several PDE family members including PDE1, PDE3, PDE4, PDE7, PDE8, PDE10, and PDE11.

PDE inhibitors increase intracellular cAMP levels by preventing the degradation of intracellular second messengers (e.g., cAMP) by PDE. Thus, suitable compounds that increase cAMP for carrying out the disclosed methods include, but are not limited to, phosphodiesterase (PDE) inhibitors. In certain embodiments, the PDE inhibitors are non-selective inhibitors. For example, the PDE inhibitor may be 3-Isobutyl-1-methylxanthine, zardaverine, and/or trequinsin. In certain embodiments, the PDE inhibitors are PDE1 inhibitors, PDE3 inhibitors, PDE 4 inhibitors, PDE7 inhibitors, PDE8 inhibitors, PDE10 inhibitors, and/or PDE11 inhibitors. Suitable PDE3 inhibitors include, without limitation, cilostamide and/or milrinone. Suitable PDE4 inhibitors include, without limitation, irsogladine, glaucine, etazolate, CGH2466, rolipram, and/or bay 19-8004. Suitable PDE5 inhibitors include, without limitation, dipyridamole, vardenafil, and/or tadalafil. Suitable PDE10 inhibitors include, without limitation, papaverine. In certain embodiments, the PDE inhibitors are selected from the group consisting of trequinsin, zardaverine, cilostamide. In certain embodiments, the PDE inhibitor increasing β-cell replication by acting as a PDE4/PDE10 inhibitor. Accordingly, the PDE inhibitor is dipyridamole.

In some embodiments, the PDE inhibitor is specific for β-cells and not α-cells (Zhao et al., "Repurposing cAMP-Modulating Medications to Promote β-Cell Replication," *Mol. Endocrinol.* 28(10): 1682-1697 (2014), which is hereby incorporated by reference in its entirety). Thus, in an embodiment, the PDE inhibitor is dipyridamole.

As described above, GLP1R agonists, and additional agents that prevent degradation of endogenous GLP1 by the enzyme dipeptidylpeptidase IV (DPP4) have been shown to induce proliferation in rodent beta cells, but have failed to show activation of beta cell replication in adult human islets (Drucker D J, "Mechanisms of Action and Therapeutic Application of Glucagon-Like Peptide-1," *Cell Metab.* 27(4):740-756 (2018) and Deacon et al., "Dipeptidyl Peptidase-4 Inhibitors for the Treatment of Type 2 Diabetes: Comparison, Efficacy and Safety," *Expert Opin. Pharmacother.* 14(15):2047-2058 (2013), which are hereby incorporated by reference in their entirety). The present disclosure demonstrates that inhibiting DYRK1A in combination with an agent that increases GLP1 activity synergistically increases human beta cell proliferation.

Thus, another aspect of the disclosure relates to a method of treating a subject for a condition associated with insufficient insulin secretion. This method involves administering to a subject in need of treatment for a condition associated with an insufficient level of insulin secretion a dual-specificity tyrosine phosphorylation-regulated kinase 1A (DYRK1A) inhibitor and a dipeptidylpeptidase IV (DPP4) inhibitor, where the administering is carried out under conditions effective to cause a synergistic increase in pancreatic beta cell mass in the subject to treat the subject for an insufficient level of insulin secretion.

As described herein above, the methods described herein may be carried out in vivo. In some embodiments, administering a dual-specificity tyrosine phosphorylation-regulated kinase 1A (DYRK1A) inhibitor and a dipeptidylpeptidase IV (DPP4) inhibitor is carried out with a composition comprising both the DYRK1A inhibitor and the DPP4 inhibitor.

As described herein above, the subject may be treated for one or more of Type I diabetes ("T1D"), Type II diabetes ("T2D"), gestational diabetes, congenital diabetes, maturity onset diabetes ("MODY"), cystic fibrosis-related diabetes, hemochromatosis-related diabetes, drug-induced diabetes, or monogenic diabetes. In some embodiments, the subject is a mammalian subject. The subject may be a human subject.

As described herein above, administering a dual-specificity tyrosine phosphorylation-regulated kinase 1A (DYRK1A) inhibitor and a dipeptidylpeptidase IV (DPP4) inhibitor may increase glucose-stimulated insulin secretion in pancreatic beta cells of the subject.

Suitable DYRK1 inhibitors are described in detail above. In some embodiments, the DYRK1A inhibitor is selected from the group consisting of harmine, INDY, leucettine-41, 5-iodotubercidin (5-IT), GNF4877, CC-401, thiadiazine kinase inhibitors, and combinations thereof.

Suitable DPPR inhibitors include, but are not limited to, sitagliptin, vildagliptin, saxagliptin, linagliptin, alogliptin, and combinations thereof (Drucker D J, "Mechanisms of Action and Therapeutic Application of Glucagon-Like Peptide-1," *Cell Metab.* 27(4):740-756 (2018) and Deacon et al., "Dipeptidyl Peptidase-4 Inhibitors for the Treatment of Type 2 Diabetes: Comparison, Efficacy and Safety," *Expert*

Opin. Pharmacother. 14(15):2047-2058 (2013), which are hereby incorporated by reference in their entirety).

EXAMPLES

Material and Methods for Examples 1-6

Human Islets: Human islets from 81 normal donors were obtained through the NIH-supported Integrated Islet Distribution Program (IIDP), the Alberta Diabetes Institute Islet Core at the University of Alberta, and the Clinical Islet Laboratory, University of Alberta Hospital. Islets were harvested from pancreata from deceased organ donors without any identifying information with informed consent and IRB approval at the islet-isolating centers. Donors ranged in age from 15 to 76 years (mean±SEM, 45.3±12.9); 26 were female, 53 were male. Mean BMI was 30.3±5.6 (range 17.3-44.4), and cold ischemia time was 604 min (range 270-969 min). Purity ranged from 55 to 98% (mean 84.9±8.5). In addition, islets were obtained from 11 donors with Type 2 diabetes. The ages ranged from 26 to 71 years (mean 48.2±13.6); 3 were female, 8 were male. Mean BMI was 31.7±4.4 (range 27.3-38.1), and cold ischemia time was 582 min (range 155-1200 min). Purity ranged from 55% to 85%. The HbA1C ranged from 6.6 to 14.1 (mean 7.9). Three were known to be on diabetes medications (metformin n=3, DPP4 inhibitor n=1). Upon arrival, islets were cultured in islet culture medium (RPMI 1640 medium containing 10% fetal bovine serum (FBS), 5.5 mM glucose, and 1% penicillin-streptomycin at 37° C. and 5% $CO_2$ overnight. Islet Dispersion: Islets were dispersed into single cells with Accutase as previously described (Wang et al., "A High-Throughput Chemical Screen Reveals that Harmine-Mediated Inhibition of DYRK1A Increases Human Pancreatic Beta Cell Replication," *Nature Medicine* 21:383-388 (2015); Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," *Diabetes* 53:149-59 (2004); and Fiaschi-Taesch et al., "Induction of Human Beta Cell Proliferation and Engraftment Using a Single G1/S Regulatory Molecule, cdk6," *Diabetes* 59:1926-36 (2010), which are hereby incorporated by reference in their entirety). Whole islets were pelleted by centrifugation at 200×G and washed twice in PBS. Islets were then incubated in Accutase for 15-17 minutes at 37° C., and completely dispersed to single cells by pipette trituration. Single islet cells were pelleted by centrifugation at 700×G and re-suspended in islet culture medium.

Chemicals and Compounds: Reagents were purchased as follows: Accutase (Mediatech: 25-058-CL), harmine (286044, Sigma), leucettine-41 (MR-00023, Adipogen), INDY (4997, Tocris Biosciences), GLP-1(7-36) amide (H-6795, Bachem), Exendin-4 (acetate) (11940, Cayman), Liraglutide acetate salt (H-8148, Bachem), Lixisenatide acetate salt (H-7426, Bachem), Semaglutide acetate (H-7894, Bachem), forskolin (11018, Cayman), ducladesine (dibutyryl cAMP) (14408, Cayman), IBMX (13347, Cayman), dipyridamole (18189, Cayman), H-89 (10010556, Cayman), N6-benzoyl-Cyclic AMP (5255, Tocris), 8-pCPT-2'-O-Me-Cyclic AMP (17143, Cayman), ESI-05 (SML1907, Sigma), recombinant human IL-10 (201-lb-005, R&D Systems), recombinant human TNF-α (210-TA-010, R&D Systems), Amersham Cell Proliferation Labelling Reagent (RPN201, GE).

Compound Treatments: Dispersed islets were plated on poly-D-lysine-laminin-coated glass chamber slides or coverslips. Cells derived from 20-30 IEQ dispersed cells were seeded per well, and allowed to recover for 24 hr prior to compound treatment. Cells were treated for 96 hours prior to Ki67 staining, BrdU staining or TUNEL labeling. For TUNEL labeling, a cytokine cocktail containing TNFα and IL-1β, 1000 Units/ml and 500 Units/ml respectively, was used.

Immunocytochemistry: Following treatment, cells were fixed with 4% paraformaldehyde and immunostained with antibodies against a proliferation marker (Ki67, or BrdU) and insulin (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015); Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," *Diabetes* 53(1):149-59 (2004); and Fiaschi-Taesch et al., "Induction of Human Beta Cell Proliferation and Engraftment Using a Single G1/S Regulatory Molecule, cdk6," *Diabetes* 59(8):1926-1936 (2010), each of which is hereby incorporated by reference in its entirety). Antibodies were diluted in blocking buffer (5% normal goat serum (NGS), 1% bovine serum albumin (BSA), 0.5% Triton, in PBS). Primary and secondary antisera used are listed below. BrdU (Cell Proliferation Labelling Reagent, Amersham GE Healthcare, GE: RPN201) was added to each treatment at a 1:100 dilution, 18 hours prior to fixation. Antigen retrieval for BrdU immunostaining was performed following fixation using 1N HCl at 37° C. for 30 minutes before primary antibody incubation. Cells were incubated with primary and secondary antibodies according to Table 4 below before counterstained with DAPI. TUNEL labeling was performed using the DeadEnd Fluorometric System (Cat #G3250, Promega).

TABLE 4

Cell Labeling Reagents

| Target | Host | Manufacturer | Cat # | Dilution | Incubation Time |
|---|---|---|---|---|---|
| Ki67 | Rabbit | Thermo Scientific | Sp6, RM-9106 | 1:300 | 2 hr, RT |
| Insulin | GP | Dako | A0564 | 1:500 | 2 hr, RT |
| BrdU | Rat | Abcam | ab6326 | 1:300 | 2 hr, RT |
| Glucagon | Rabbit | Abcam | ab108426 | 1:200 | 2 hr, RT |
| Somatostatin | Rabbit | Santa Cruz | Sc-20999 | 1:200 | 2 hr, RT |
| Cytokeratin 19 | Rabbit | Abcam | ab52625 | 1:200 | 2 hr, RT |
| DYRK1A | Rabbit | SIGMA | D1694 | 1:200 | 2 hr, RT |
| Rat | Goat | Life Technologies | A11007 | 1:500 | 1 hr, RT |
| Rabbit | Goat | Life Technologies | A11037 | 1:500 | 1 hr, RT |
| Guinea Pig | Goat | Life Technologies | A11073 | 1:500 | 1 hr, RT |

Adenovirus Generation and Use: Adenoviruses, under the control of the CMV promoter, were prepared using cDNAs encoding Cre or human DYRK1A or shRNAs, under the control of the U6 promoter, directed against LacZ or human DYRK1A as described previously (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015), which is hereby incorporated by reference in its entirety). Dispersed human islets were transduced on coverslips with experimental or control adenoviruses at 100-150 multiplicity of infection in serum free medium for 2 hours. Complete medium containing 10% FCS was added to stop transduction and cells were cultured for 96 hours as described in the Figures.

Glucose-Stimulated Insulin Secretion: Insulin release was measured in duplicate from intact human islets treated with either vehicle, harmine, GLP1, or the combination (20 islet equivalents per condition) for 72 hours (Wang et al., "A High-Throughput Chemical Screen Reveals that Harmine-Mediated Inhibition of DYRK1A Increases Human Pancreatic Beta Cell Replication," Nat. Med. 21(4):383-388 (2015); Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," Diabetes 53(1):149-59 (2004); and Fiaschi-Taesch et al., "Induction of Human Beta Cell Proliferation and Engraftment Using a Single G1/S Regulatory Molecule, cdk6," Diabetes 59(8):1926-1936 (2010), each of which is hereby incorporated by reference in its entirety). Islets were incubated in 1 ml Krebs-Ringer bicarbonate buffer supplemented with 10 mM HEPES, 1% BSA, and 2.8 mM glucose for 1 hour at 37° C. in a 5% $CO_2$ incubator, then incubated in 1 ml fresh Krebs-Ringer bicarbonate buffer supplemented with 0.1% BSA, and either 2.8 or 16.8 mM glucose for 30 minutes at 37° C. Buffer was removed, collected, and frozen at −20° C. for insulin measurement by insulin ELISA (10-1113-01, Mercodia). Islets were digested overnight in 0.1N NaOH at 37° C. and protein was measured by Bradford assay after neutralization with HCl. Insulin values are normalized to protein content.

RNA Extraction and q-PCR: Total RNA was purified from dispersed islets using the Qiagen RNeasy Mini System (74104, Qiagen) according to the manufacturer's instructions (Wang et al., "A High-Throughput Chemical Screen Reveals that Harmine-Mediated Inhibition of DYRK1A Increases Human Pancreatic Beta Cell Replication," Nat. Med. 21(4):383-388 (2015), which is hereby incorporated by reference in its entirety). cDNA was then prepared using the SuperScript IV VILO (Ser. No. 11/756,050, Life Technologies). Gene expression in dispersed islets was analyzed using the Bio Rad SYBRGreen system (1725271, BioRad) on an ABI 7500 Real Time PCR machine (Life Technologies, Grand Island, N.Y.). Relative quantification of gene expression was analyzed by the comparative cycle threshold method with Cyclophilln A (CYPA) as the reference. Primers are shown below in Tables 5 and 6.

TABLE 5

Forward Primer Sequences

| | Forward Primer Sequence | SEQ ID NO. |
|---|---|---|
| CCNA1 (Cyclin A1) | GAGGTCCCGATGCTTGTCAG | SEQ ID NO: 1 |
| CCNA2 (Cyclin A2) | GGATGGTAGTTTTGAGTCACCAC | SEQ ID NO: 2 |
| CCNB1 (Cyclin B1) | AATAAGGCGAAGATCAACATGGC | SEQ ID NO: 3 |
| CCNB2 (Cyclin B2) | TTGGCTGGTACAAGTCCACTC | SEQ ID NO: 4 |
| CCNB3 (Cyclin B3) | ATGAAGGCAGTATGCAAGAAGG | SEQ ID NO: 5 |
| CCND1 (Cyclin D1) | CAATGACCCCGCACGATTTC | SEQ ID NO: 6 |

TABLE 5-continued

Forward Primer Sequences

| | Forward Primer Sequence | SEQ ID NO. |
|---|---|---|
| CCND2 (Cyclin D2) | TTTGCCATGTACCCACCGTC | SEQ ID NO: 7 |
| CCND3 (Cyclin D3) | TACCCGCCATCCATGATCG | SEQ ID NO: 8 |
| CCNE1 (Cyclin E1) | ACTCAACGTGCAAGCCTCG | SEQ ID NO: 9 |
| CCNE2 (Cyclin E2) | TCAAGACGAAGTAGCCGTTTAC | SEQ ID NO: 10 |
| CDC2 (CDK1) | GGATGTGCTTATGCAGGATTCC | SEQ ID NO: 11 |
| CDK2 | GTACCTCCCCTGGATGAAGAT | SEQ ID NO: 12 |
| CDK4 | TCAGCACAGTTCGTGAGGTG | SEQ ID NO: 13 |
| CDK6 | CCAGATGGCTCTAACCTCAGT | SEQ ID NO: 14 |
| CDC25A | GTGAAGGCGCTATTTGGCG | SEQ ID NO: 15 |
| CDKN1A (p21) | CGATGGAACTTCGACTTTGTCA | SEQ ID NO: 16 |
| CDKN1B (p27) | TAATTGGGGCTCCGGCTAACT | SEQ ID NO: 17 |
| CDKN1C (p57) | GCGGCGATCAAGAAGCTGT | SEQ ID NO: 18 |
| CDKN2A (p16) | ATGGAGCCTTCGGCTGACT | SEQ ID NO: 19 |
| CDKN2B (p15) | CGTTAAGTTTACGGCCAACG | SEQ ID NO: 20 |
| CDKN2C (p18) | AAACTTGGAAATCCCGAGATTGC | SEQ ID NO: 21 |
| CDKN2D (p19) | AGTCCAGTCCATGACGCAG | SEQ ID NO: 22 |
| c-MYC | CCACACATCAGCACAACTACG | SEQ ID NO: 23 |
| Cyclophilin A | CACCGTGTTCTTCGACATTG | SEQ ID NO: 24 |
| FOXM1 | ATACGTGGATTGAGGACCACT | SEQ ID NO: 25 |
| DYRK1A | GCCAGGGAGACGATTCTAGTC | SEQ ID NO: 26 |
| GLP1R | GGTGCAGAAATGGCGAGAATA | SEQ ID NO: 27 |
| INS | TCACACCTGGTGGAAGCTCTCTA | SEQ ID NO: 28 |
| ISL1 | AGGAGCAACTGGTAGAGATGAC | SEQ ID NO: 29 |
| MAFA | GAGCGGCTACCAGCATCAC | SEQ ID NO: 30 |
| MAFB | TCAAGTTCGACGTGAAGAAGG | SEQ ID NO: 31 |
| NeuroD1 | GTCTCCTTCGTTCAGACGCTT | SEQ ID NO: 32 |
| NGN3 | CTAAGAGCGAGTTGGCACTGA | SEQ ID NO: 33 |
| NKX6.1 | ACACGAGACCCACTTTTTCCG | SEQ ID NO: 34 |
| PAX4 | AGTCCTGCGGGCATTACAG | SEQ ID NO: 35 |
| PCSK1 | GGACCTCTGAGTATGACCCG | SEQ ID NO: 36 |
| PCSK2 | GGGAAAGGTGTTACCATTGGAA | SEQ ID NO: 37 |
| PDX1 | TGATGTGTCTCTCGGTCAAGTT | SEQ ID NO: 38 |
| ARX | CTGCTGAAACGCAAACAGAG | SEQ ID NO: 39 |
| SLC2A1 (GLUT1) | GGCCAAGAGTGTGCTAAAGAA | SEQ ID NO: 40 |
| SLC2A2 (GLUT2) | GCTGCTCAACTAATCACCATGC | SEQ ID NO: 41 |

TABLE 6

Reverse Primer Sequences

| | Reverse Primer Sequence | SEQ ID NO. |
|---|---|---|
| CCNA1 (Cyclin A1) | GTTAGCAGCCCTAGCACTGTC | SEQ ID NO: 42 |
| CCNA2 (Cyclin A2) | CACGAGGATAGCTCTCATACTGT | SEQ ID NO: 43 |
| CCNB1 (Cyclin B1) | TTTGTTACCAATGTCCCCAAGAG | SEQ ID NO: 44 |
| CCNB2 (Cyclin B2) | TGGGAACTGGTATAAGCATTGTC | SEQ ID NO: 45 |
| CCNB3 (Cyclin B3) | CATCCACACGAGGTGAGTTGT | SEQ ID NO: 46 |
| CCND1 (Cyclin D1) | CATGGAGGGCGGATTGGAA | SEQ ID NO: 47 |
| CCND2 (Cyclin D2) | AGGGCATCACAAGTGAGCG | SEQ ID NO: 48 |
| CCND3 (Cyclin D3) | AGGCAGTCCACTTCAGTGC | SEQ ID NO: 49 |
| CCNE1 (Cyclin E1) | GCTCAAGAAAGTGCTGATCCC | SEQ ID NO: 50 |
| CCNE2 (Cyclin E2) | TGACATCCTGGGTAGTTTTCCTC | SEQ ID NO: 51 |
| CDC2 (CDK1) | CATGTACTGACCAGGAGGGATAG | SEQ ID NO: 52 |
| CDK2 | CGAAATCCGCTTGTTAGGGTC | SEQ ID NO: 53 |
| CDK4 | GTCCATCAGCCGGACAACAT | SEQ ID NO: 54 |
| CDK6 | AACTTCCACGAAAAAGAGGCTT | SEQ ID NO: 55 |
| CDC25A | TGGTTGCTCATAATCACTGCC | SEQ ID NO: 56 |
| CDKN1A (p21) | GCACAAGGGTACAAGACAGTG | SEQ ID NO: 57 |
| CDKN1B (p27) | TGCAGGTCGCTTCCTTATTCC | SEQ ID NO: 58 |
| CDKN1C (p57) | GCTTGGCGAAGAAATCGGAGA | SEQ ID NO: 59 |
| CDKN2A (p16) | GTAACTATTCGGTGCGTTGGG | SEQ ID NO: 60 |
| CDKN2B (p15) | GGTGAGAGTGGCAGGGTCT | SEQ ID NO: 61 |
| CDKN2C (p18) | CGAAACCAGTTCGGTCTTTCAA | SEQ ID NO: 62 |
| CDKN2D (p19) | ATCAGGCACGTTGACATCAGC | SEQ ID NO: 63 |
| c-MYC | CAGCAGGATAGTCCTTCCGAG | SEQ ID NO: 64 |
| Cyclophilin A | TGAAGTCACCACCCTGACAC | SEQ ID NO: 65 |
| FOXM1 | TCCAATGTCAAGTAGCGGTTG | SEQ ID NO: 66 |
| DYRK1A | AACCCATTCTTGCTCCACAC | SEQ ID NO: 67 |
| GLP1R | CCGGTTGCAGAACAAGTCTGT | SEQ ID NO: 68 |
| INS | ACAATGCCACGCTTCTGCAGGGAC | SEQ ID NO: 69 |
| ISL1 | GTCCTTGCACCGCTTGTTTTG | SEQ ID NO: 70 |
| MAFA | CTCTGGAGTTGGCACTTCTCG | SEQ ID NO: 71 |

TABLE 6-continued

Reverse Primer Sequences

| | Reverse Primer Sequence | SEQ ID NO. |
|---|---|---|
| MAFB | GTTCATCTGCTGGTAGTTGCT | SEQ ID NO: 72 |
| NeuroD1 | AAAGTCCGAGGATTGAGTTGC | SEQ ID NO: 73 |
| NGN3 | GAGGTTGTGCATTCGATTGCG | SEQ ID NO: 74 |
| NKX6.1 | TGCTGGACTTGTGCTTCTTCAAC | SEQ ID NO: 75 |
| PAX4 | GGGAGAAGATAGTCCGATTCCG | SEQ ID NO: 76 |
| PCSK1 | AGCTTTGGCATTTAGCAAGCC | SEQ ID NO: 77 |
| PCSK2 | CCAGTCATCTGTGTACCGAGG | SEQ ID NO: 78 |
| PDX1 | ACCAAAGCTCACGCGTGGAAA | SEQ ID NO: 79 |
| ARX | CGACGGTTCTGGAACCAGACC | SEQ ID NO: 80 |
| SLC2A1 (GLUT1) | ACAGCGTTGATGCCAGACAG | SEQ ID NO: 81 |
| SLC2A2 (GLUT2) | TGGTCCCAATTTTGAAAACCCC | SEQ ID NO: 82 |

Quantitative Human Beta Cell Flow Cytometry: Human islets (250-300 IEQ) or stem cell-derived beta cells (300-500,000) were dispersed using Accutase (MT25058CI, Fisher Scientific) (for human islets) or trypsin (for hESC-derived beta cells) and plated on laminin/poly-D-lysine coated chamber slides (BD354688, VWR Scientific). For human islets, beta cells were labeled with an adenovirus as described previously (Wang et al., "A High-Throughput Chemical Screen Reveals that Harmine-Mediated Inhibition of DYRK1A Increases Human Pancreatic Beta Cell Replication," Nat. Med. 21(4):383-388 (2015); Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," Diabetes 53(1):149-59 (2004); and Fiaschi-Taesch et al., "Induction of Human Beta Cell Proliferation and Engraftment Using a Single G1/S Regulatory Molecule, cdk6," Diabetes 59(8):1926-1936 (2010), each of which is hereby incorporated by reference in its entirety). Briefly, human islet cells were dispersed to single cells in eight-well chambers and transduced for two hours in RPMI1640 medium without fetal bovine serum (FBS) with 150 moi of an adenovirus expressing the bright green fluorescent protein, ZsGreen (Clontech, Mountain View Calif.), under control of the rat insulin-1 promoter (RIP1) and a mini-CMV enhancer (Wang et al., "Insights into Human Beta Cell Regeneration for Diabetes via Integration of Molecular Landscapes in Human Insulinomas. Nat. Comm. 8(1):767 (2017), which is hereby incorporated by reference in its entirety). The RIP1-miniCMV promoter included 177 bases of the hCMV IE-1 promoter ClaI-SpeI fragment ligated to 438 bases of the RIP1 promoter. The beta cell fraction has been confirmed to be >92% pure by immunolabeling of sorted cells with insulin, by qRT-PCR and by RNAseq (Wang et al., "Insights into Human Beta Cell Regeneration for Diabetes via Integration of Molecular Landscapes in Human Insulinomas," Nat. Comm. 8(1):767 (2017), which is hereby incorporated by reference in its entirety). Following transduction with the Ad.RIP-ZsGreen adenovirus for two hours, 300 μl of RPMI1640 medium containing 10% FBS was added to terminate adenovirus infection, and cells were allowed to express ZsGreen for 24 hours. At this point, fresh medium containing DMSO or harmine 10 Ly364947 3 µM or the harmine-LY combination was added for another four days.

For flow cytometric human beta cell quantification, following four days (for human islet cells) or seven days (for hESC-derived beta cells) of drug treatment (DMSO or harmine+LY364947), cells were harvested by gentle Accutase (for human beta cells) or trypsin (for hESC-derived beta cells) dissociation and 50,000 fluorescent beads (ACURFP-50-10, Spherotech, Inc.) were added, serving as an internal recovery standard and FACS counting reference. DAPI (D3571, Life Technologies) was used as a dead/live cell marker. Dispersed cells were loaded onto an Aria II cell sorter, and live ZsGreen$^+$ (from human islets) or GFP$^+$ (from hESC) cells were counted until 10,000 beads had been counted from each the vehicle- and the harmine-LY364947-treated wells. Results are expressed as absolute numbers of ZsGreen$^+$ or GFP$^+$ beta cells, corrected to the 50,000 original internal bead standard. The beta cell fraction was confirmed to be >92% pure by immunolabeling of sorted cells with insulin, by qRT-PCR and by RNAseq (Wang et al., "Insights into Human Beta Cell Regeneration for Diabetes via Integration of Molecular Landscapes in Human Insulinomas," *Nat. Comm.* 8(1):767 (2017), which is hereby incorporated by reference in its entirety).

Statistics: All experiments were repeated multiple times in multiple of human islet preparations as indicated in the Figures. Results were accepted as significant at $p<0.05$ as determined using two-tailed Student's t-test or one-way ANOVA. A minimum of 1,000 beta cells from a minimum of different five donors was counted for each graph shown.

Figure 3A:
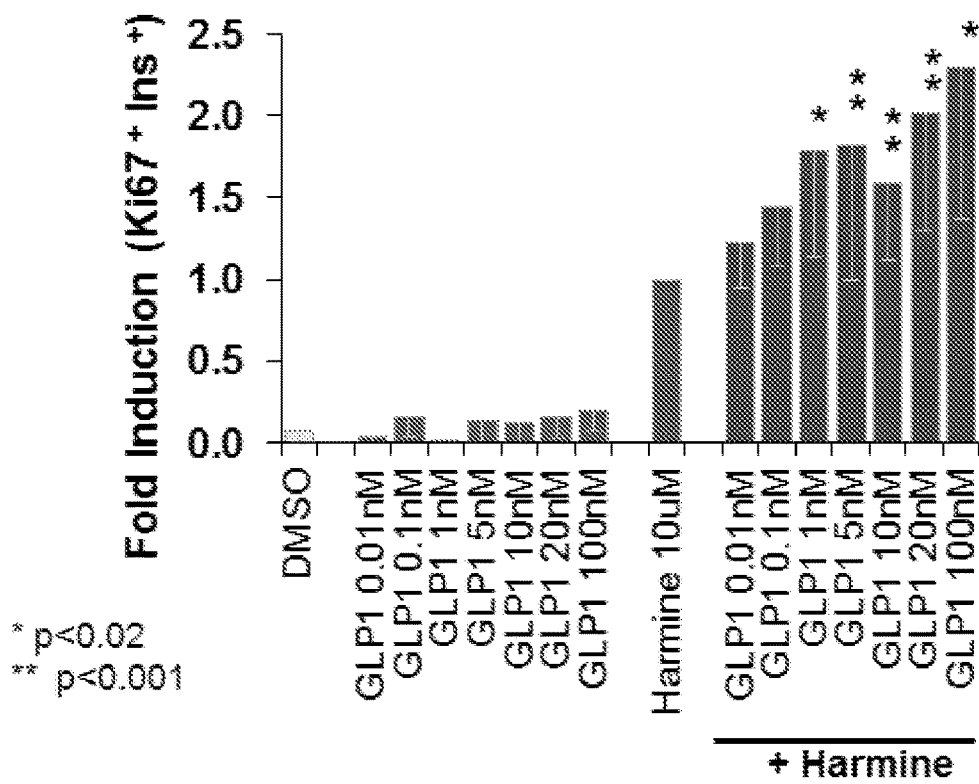
FIGS. 3A-3E provide additional evidence for synergistic activation of proliferation by the harmine-GLP1 combination.
Figures 3B, 3C:
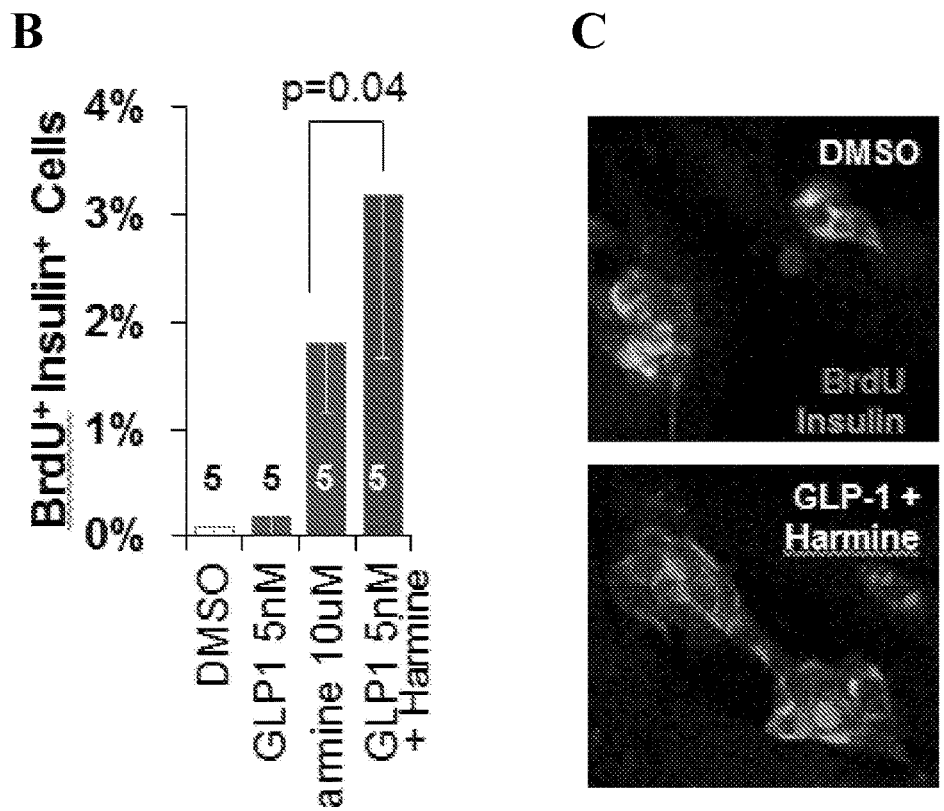
Figure 3D:
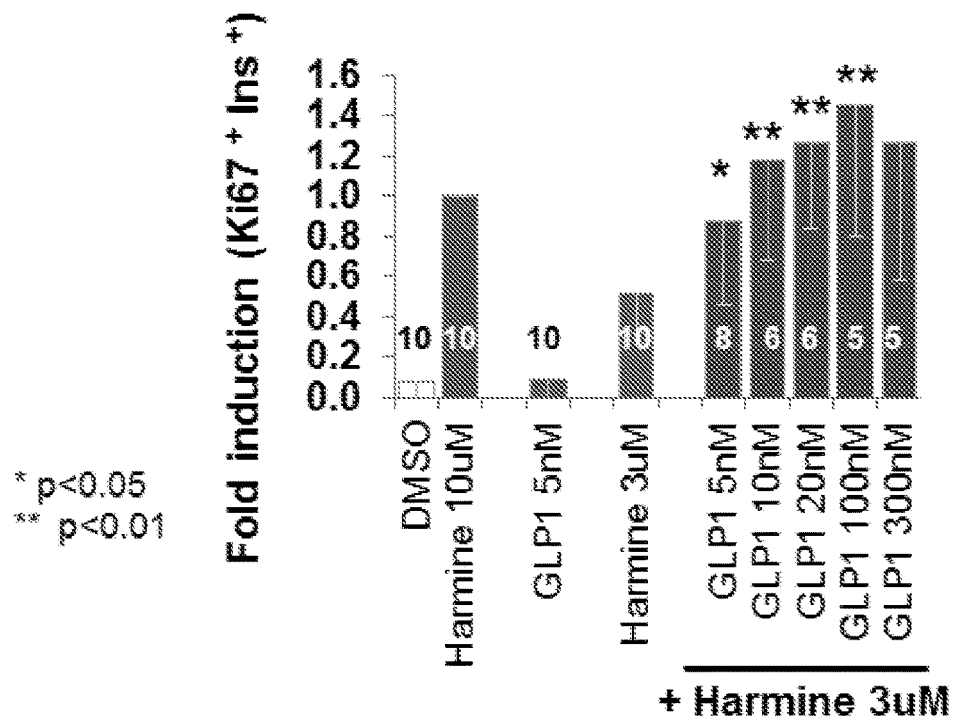
Figure 3E:
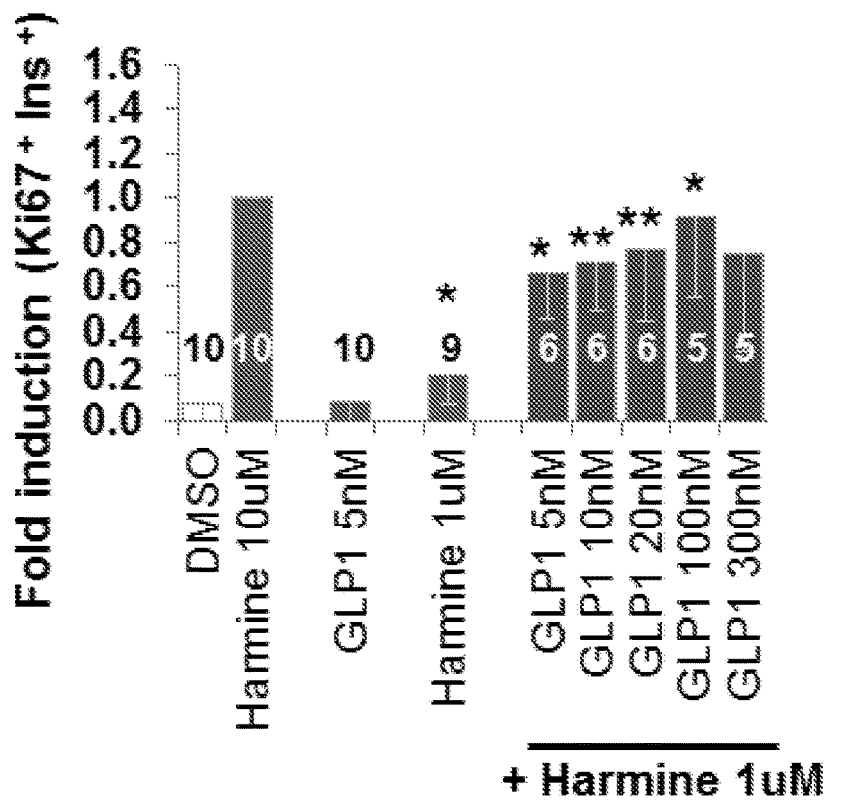

Example 1—The Harmine-GLP1 Combination Yields Synergistic Increases in Human Beta Cell Proliferation To explore whether the combination of DYRK1A inhibitors with GLP1R agonists might synergistically induce human beta cells to replicate, and provide the human beta cell targeting specificity of GLP1R agonists, adult human cadaveric islets were treated with vehicle, harmine, GLP1 (7-36)amide (referred to herein as "GLP1"), or the combination, and Ki67 immunolabeling was assessed in insulin-positive cells dispersed from human islets (FIGS. 1A-1B, 2, 3A). As previously reported (Drucker D J, "Mechanisms of Action and Therapeutic Application of Glucagon-Like Peptide-1," *Cell Metab.* 27(4):740-756 (2018); Parnaud et al., "Proliferation of Sorted Human and Rat Beta Cells," *Diabetologia* 51(1):91-100 (2008); and Dai et al., "Age-Dependent Human Beta Cell Proliferation Induced by Glucagon-Like Peptide-1 and Calcineurin Signaling," *J. Clin. Invest.* 127(10):3835-3844 (2017), which are hereby incorporated by reference in their entirety), GLP1 had negligible effects on human beta cell proliferation over a broad range of doses. As expected, harmine induced proliferation in ~2% of human beta cells (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015), which is hereby incorporated by reference in its entirety). Strikingly, however, the combination of harmine plus GLP1 resulted in an unanticipated and marked increase in human beta cell proliferation, achieving 5-6% at higher GLP1 doses, substantially higher than observed with harmine alone. Authentic human beta cell proliferation was documented through a rapid and unequivocal increase in human beta cell numbers. This contrasted to two negative controls. First, a clear dose-related decline in beta cell numbers observed with lower numbers of human islets and, second, with cytokine treatment (FIGS. 1C-1E). Notably, the synergistic effects could be observed not only at higher doses of harmine, e.g., 10 µM (FIGS. 1A-1G, 2, 3A-3C), but even at doses of harmine and GLP1 that had lesser or no effect individually (FIGS. 3D-3E). The combination of an ineffective dose of harmine (1 µM) with any dose of GLP1 produced clear synergy, generating increases in human beta cell proliferation (2.7%), comparable to the maximally efficacious dose (10 µM) of harmine alone (FIG. 3E).

Figure 4:
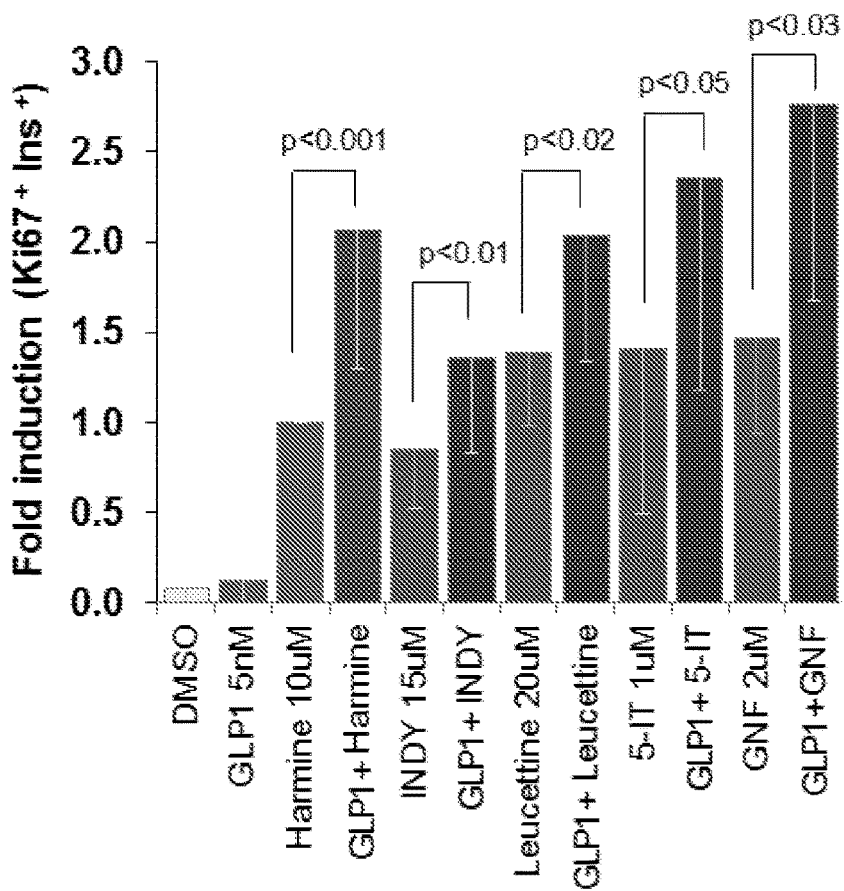
FIG. 4 is a graph showing unadjusted data for the DYRK1A inhibitor family of small molecules used alone or in conjunction with GLP1. These are the same data as shown in FIG. 1C, displayed so that the effects of each DYRK1A inhibitor alone or in combination with 5 nM GLP1 can be visualized.

Example 2—The DYRK1A-GLP1R Agonist Combination Yields Synergistic Increases in Human Beta Cell Proliferation The synergistic ability of harmine to drive proliferation in combination with GLP1 extended to every DYRK1A inhibitor tested: INDY, leucettine, 5-IT and GNF4877 (FIGS. 1F, 4), indicating that synergy with GLP1 is a "class effect" for DYRK1A inhibitors in general. Conversely, the synergy was also apparent for harmine in combination with every GLP1R agonist tested: GLP1, exendin-4, liraglutide, lixisenatide, semaglutide (FIG. 1G), indicating that mitogenic synergy with DYRK1A inhibitors is also a "class effect" for GLP1 receptor agonists in general. Collectively, the findings suggest that any DYRK1A inhibitor administered with any GLP1R agonist—and, by extension, with any DPP4 inhibitor drug that augments circulating GLP1 levels—is able to generate rates of human beta cell proliferation not previously observed with any class of drug.

Figure 5A:
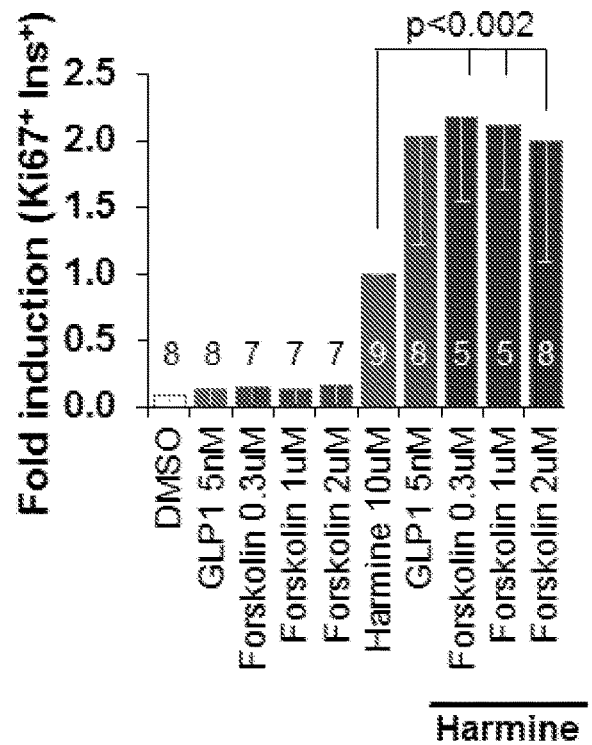
FIGS. 5A-5H demonstrate that harmine-GLP1 synergy requires inhibition of DYRK1A and increases in beta cell cAMP.
Figure 5B:
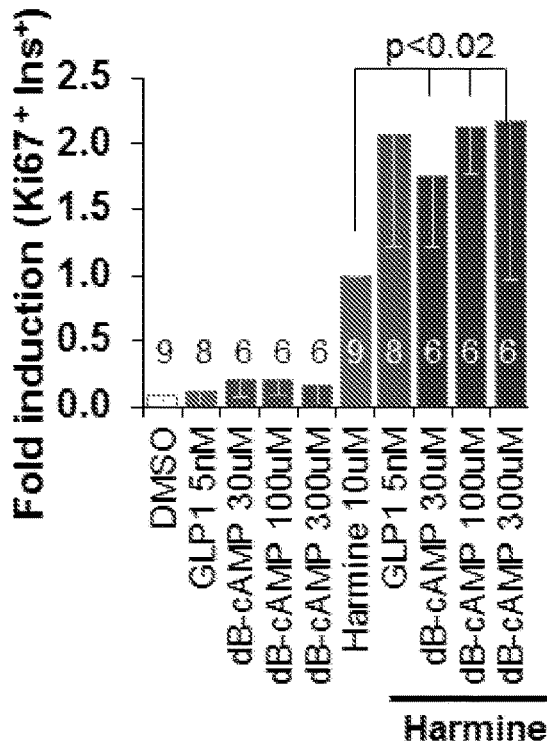
Figure 5C:
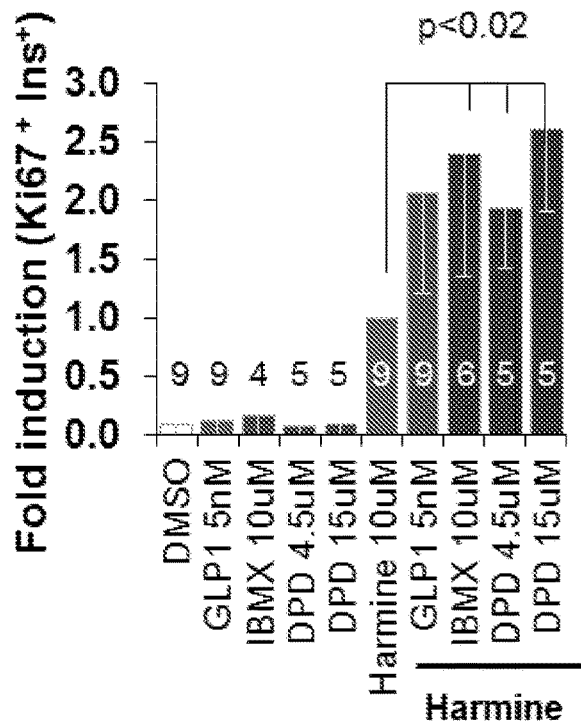
Figure 5D:
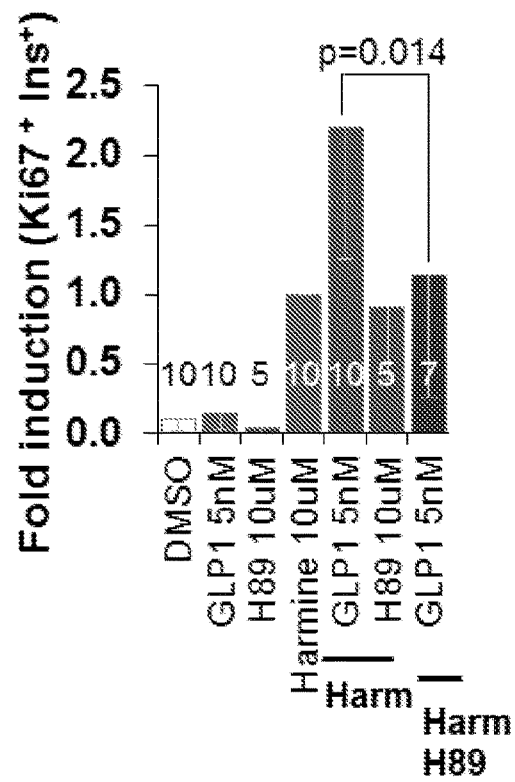
Figure 5E:
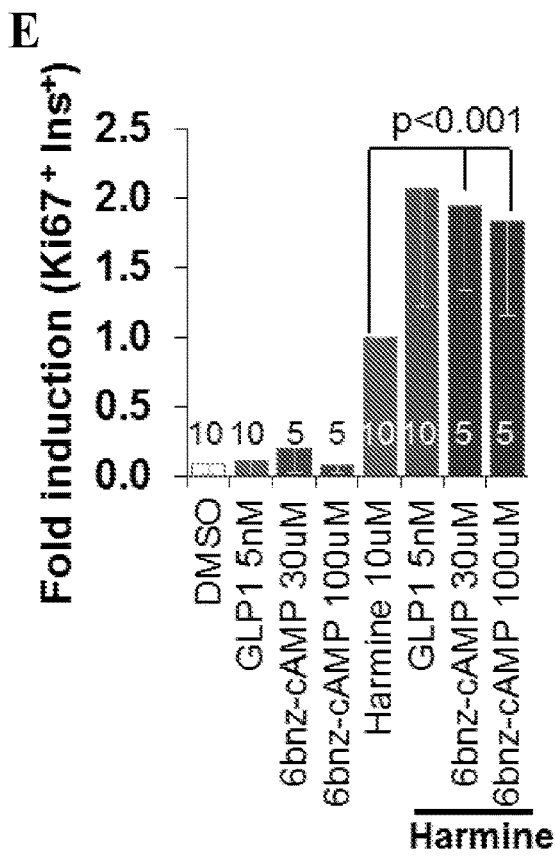
Figure 5F:
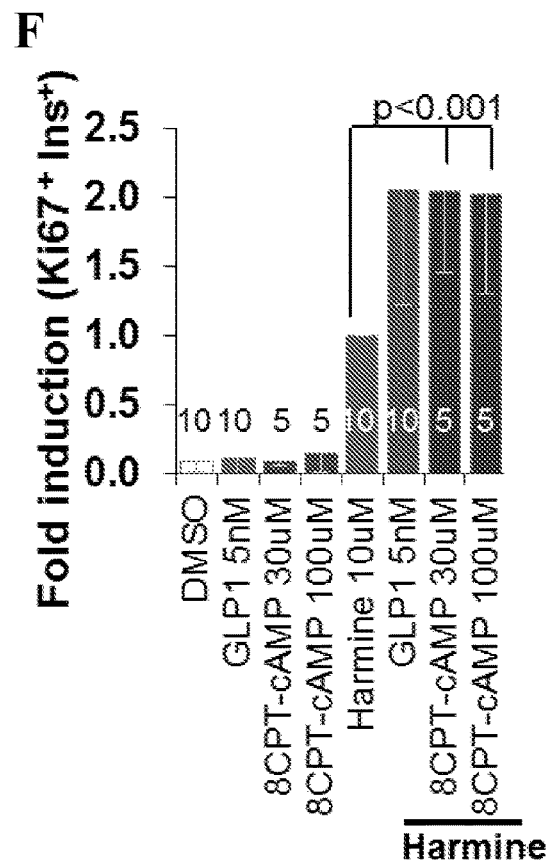
Figure 5G:
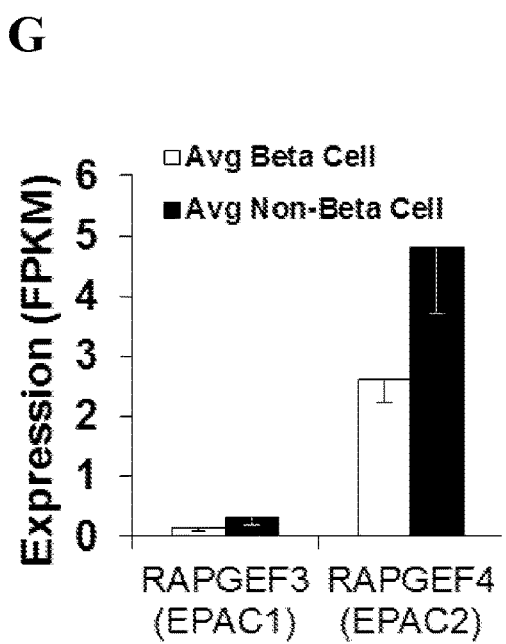
Figure 5H:
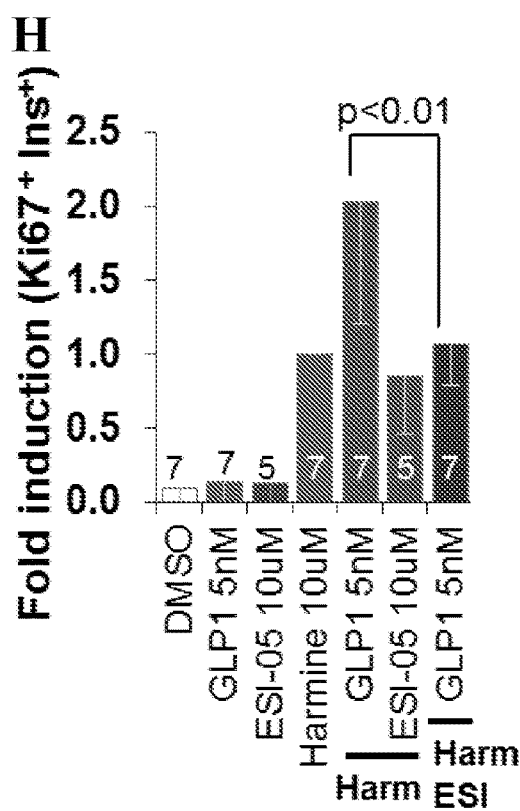
Figures 6A, 6B, 6C:
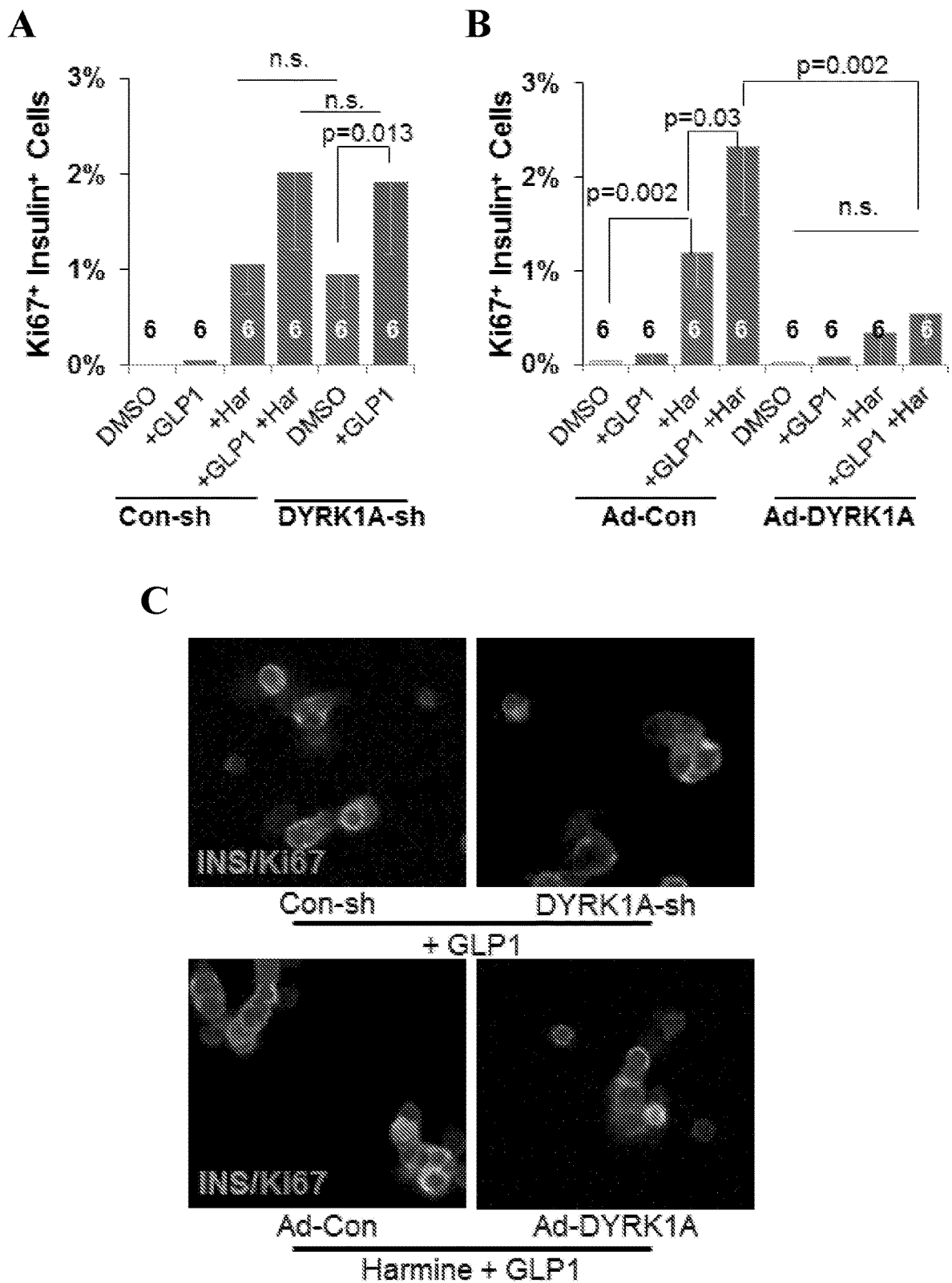
FIGS. 6A-6F show additional information on the DYRK1A-GLP1 synergy mechanism.
Figure 6D:
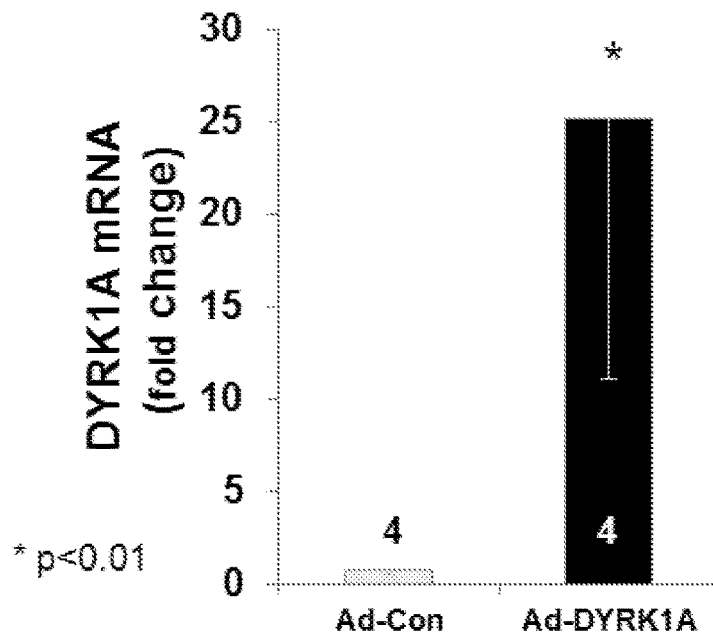
Figure 6E:
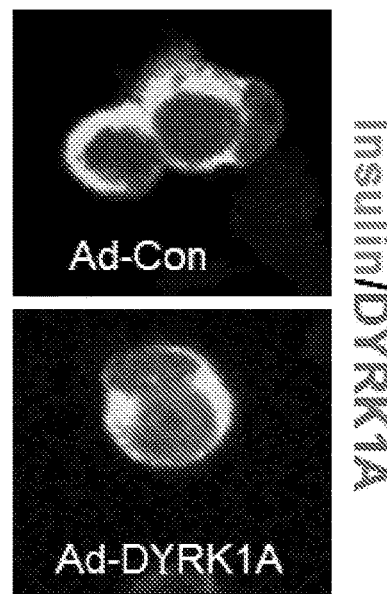
Figure 6F:
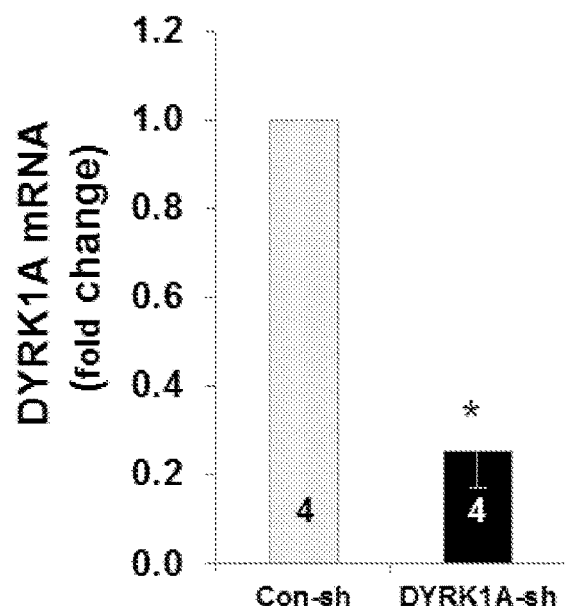

Example 3—Harmine-GLP1 Synergy Requires DYRK1A Inhibition and cAMP-PKA-EPAC Signaling The synergy requires inhibition of the DYRK1A kinase. The synergistic proliferation induced by harmine can be mimicked by adenoviral silencing of DYRK1A in human islets. Conversely, overexpressing DYRK1A can overcome the mitogenic effects of the harmine-GLP1 combination (FIGS. 6A-6F). The GLP1 synergy also requires increases in intracellular cAMP, as evidenced by the observations that harmine-GLP1 human beta cell proliferation is mimicked by harmine in combination with agents that increase cAMP, such as forskolin, dibutyryl-cyclicAMP, and the phosphodiesterase inhibitors, IBMX and dipyridamole (FIGS. 5A-5C). Moreover, the synergy can be mimicked by both the PKA and EPAC2 activators, 6-BNZ-cAMP and 8CPT-cAMP, respectively, and can be inhibited by H89 and ESI-05, pharmacologic inhibitors of PKA and EPAC2, respectively (FIGS. 5D-5H, 6F). Collectively, these findings indicate that the synergistic efficacy of harmine and GLP1 to drive human beta cell replication can be mimicked by, and requires, both inhibition of DYRK1A and activation of cAMP-PKA-EPAC2 signaling.

Figure 7A:
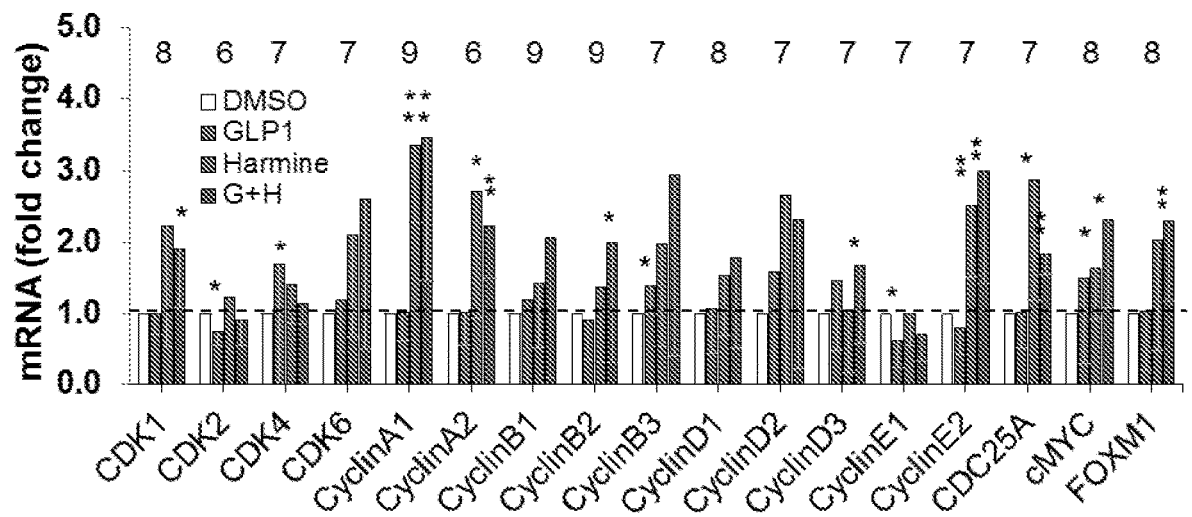
FIGS. 7A-7B show the effects of vehicle, 5 nM GLP1, 10 µM harmine, and the harmine-GLP1 combination on cell cycle molecules, assessed by qPCR.
Figure 7B:
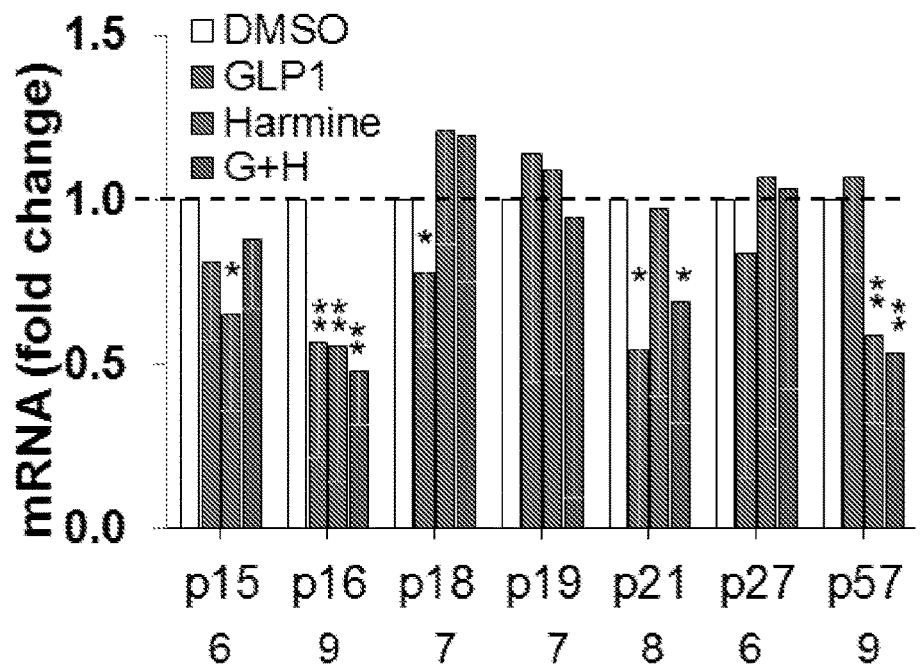

Example 4—Harmine Activates Cell Cycle-Activating Molecules and Inhibits Cell Cycle Inhibitors Harmine has been shown to activate both cell cycle-activating molecules such as cyclins, and cyclin-dependent kinases, and to inhibit cell cycle inhibitors, such as the INK4/CIP-KIP families (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015), which is hereby incorporated by reference in its entirety). This observation is confirmed, but no incremental change to cell cycle activators or inhibitors when GLP1 is added to harmine (FIGS. 7A-7B). Additional changes at the protein level may underlie the synergistic activation of proliferation.

Figure 8A:
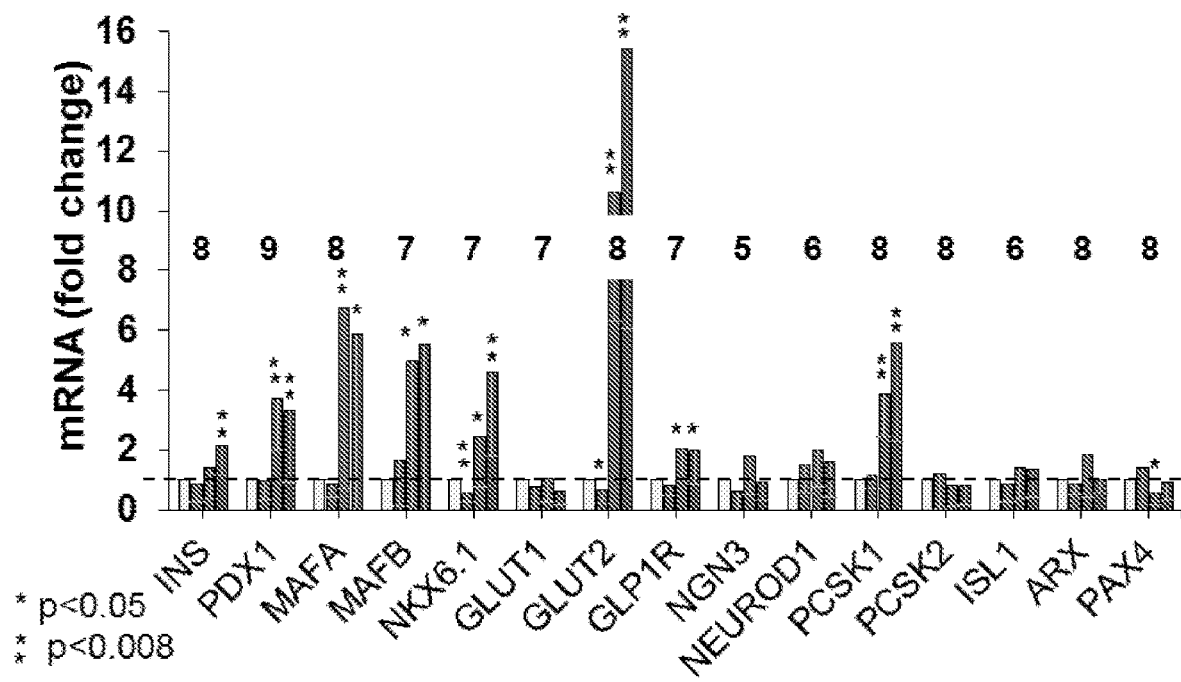
FIGS. 8A-8C show that harmine-GLP1 treatment maintains or enhances human beta cell differentiation.
Figure 8B:
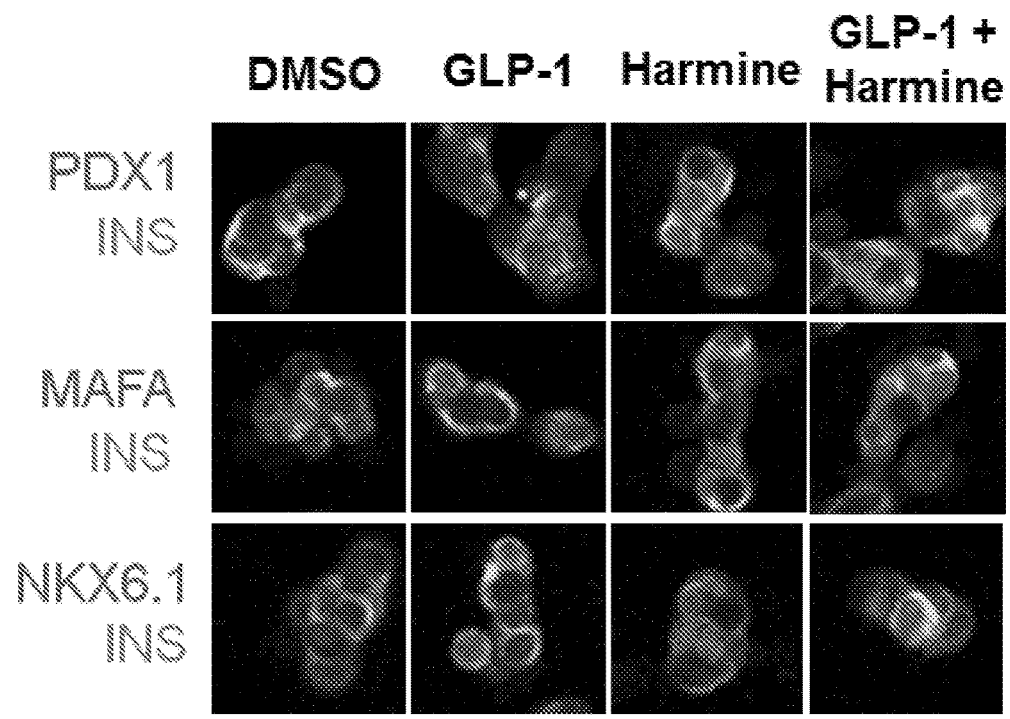
Figure 8C:
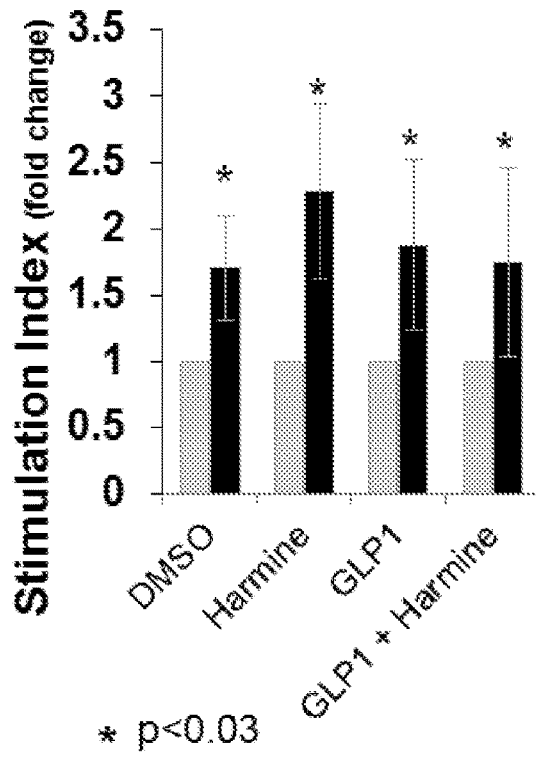

Example 5—The Harmine-GLP1 Combination Does Not Induce Beta Cell De-Differentiation Pharmacologic induction of human beta cell proliferation may lead to de-differentiation. Unexpectedly, the harmine-GLP1 combination did not lead to reduced expression of beta cell differentiation markers. Instead, it increased expression of PDX1, NKX6.1, MAFA, MAFB, GLUT2, GLP1R and PCSK1, as assessed by qPCR of whole human islets, compatible with an increase in beta cell differentiation (FIG. 8A). This was accompanied by an increase in PDX1, MAFA, and NKX6.1 proteins in individual beta cells and maintenance of normal glucose-stimulated insulin secretion (FIGS. 8B-8C). These observations indicate that the harmine-GLP1 combination does not induce beta cell de-differentiation and may even maintain or enhance differentiation.

Figure 9A:
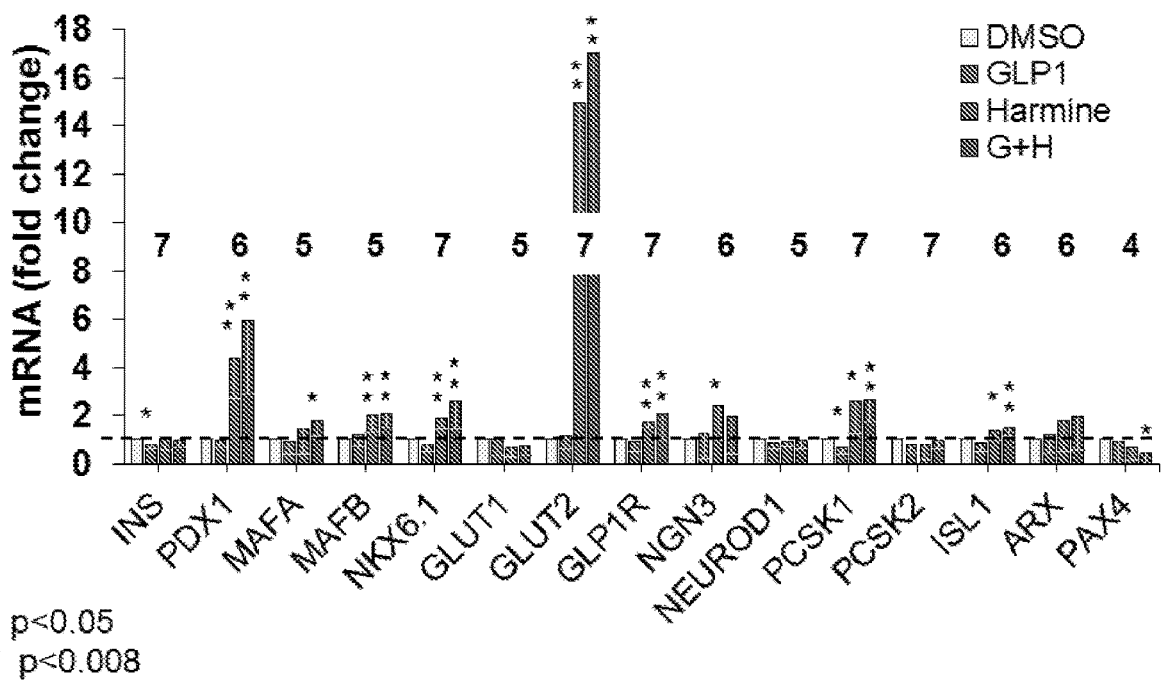
FIGS. 9A-9E show the effects of the harmine-GLP1 combination on beta cells from people with Type 2 diabetes ("T2D").
Figure 9B:
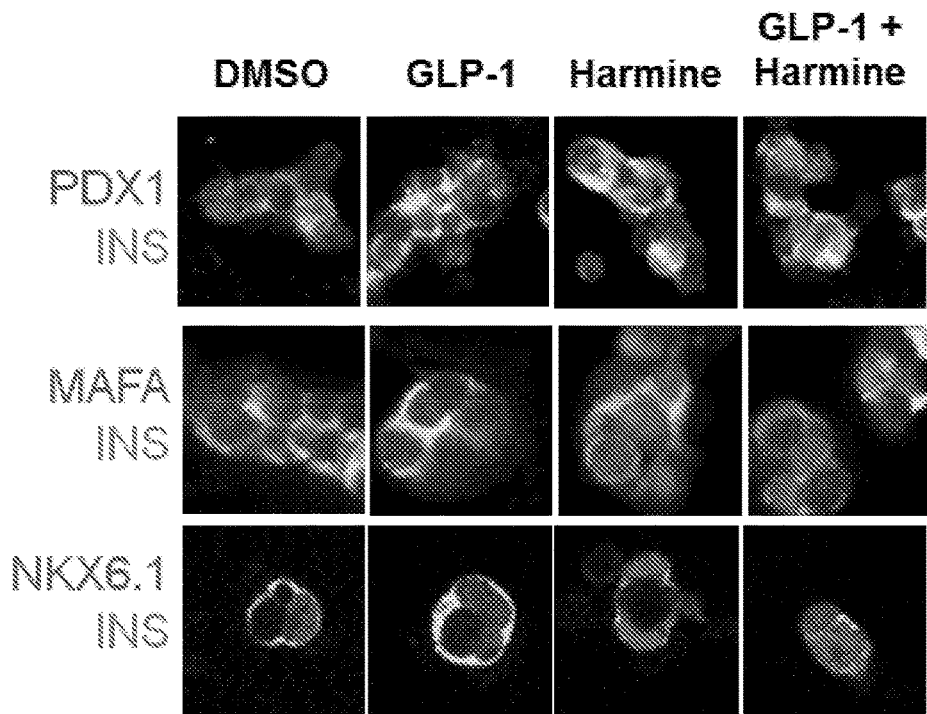
Figure 9C:
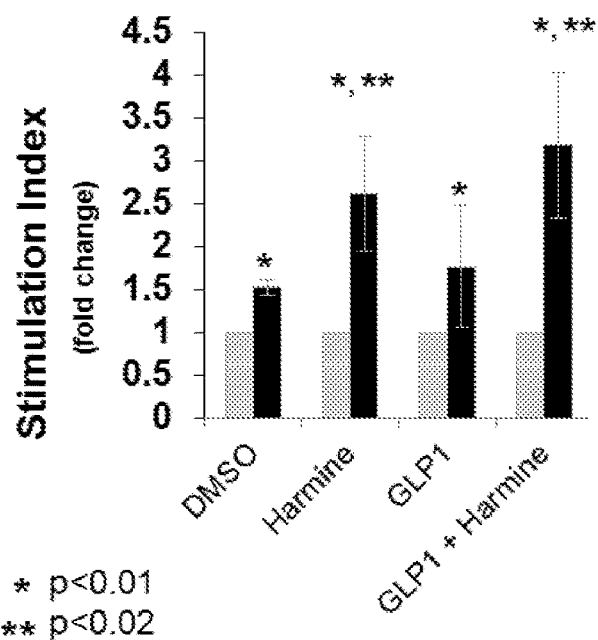
Figure 9D:
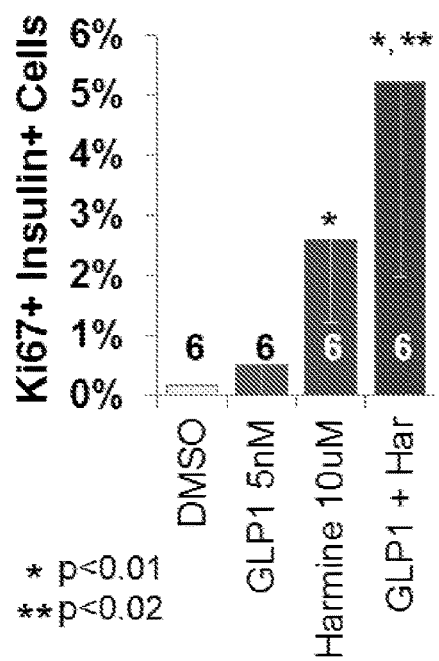
Figure 9E:
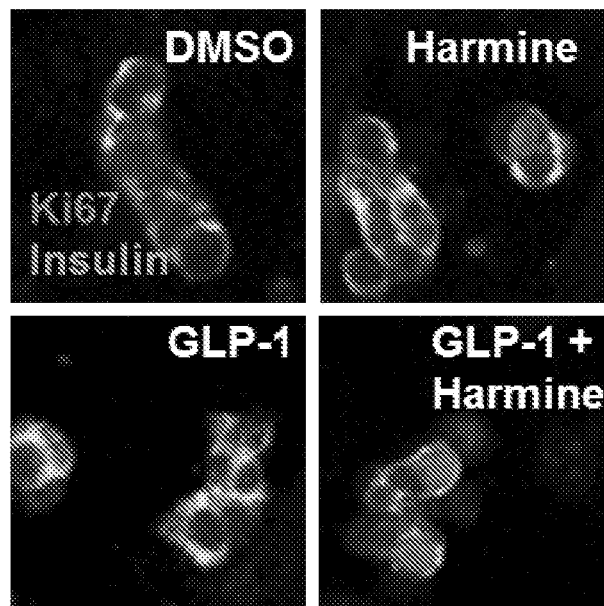

Because beta cell de-differentiation has been observed in Type 2 diabetes (T2D) (Talchai et al., "Pancreatic Beta Cell Dedifferentiation as a Mechanism of Diabetic Beta Cell Failure," *Cell* 150(6):1223-1234 (2012) and Cinti et al., "Evidence of Beta Cell De-Differentiation in Human Type 2 Diabetes," *J. Clin. Endocrinol. Metab.* 101(3):1044-54 (2016), which are hereby incorporated by reference in their entirety), the effects of the harmine-GLP1 combination on differentiation and proliferation was explored in beta cells in islets from human donors with T2D. Harmine alone, and also in combination with GLP1, increased the expression of PDX1, MAFB, NKX6.1, GLUT2, GLP1R, and PCSK1 (FIG. 9A). Interestingly, MAFA did not increase dramatically at the mRNA level, as had occurred in normal islets (FIG. 8A), but MAFA, NKX6.1, and PDX1 were all observed to increase in T2D beta cells at the protein level by immunohistochemistry, and the insulin secretory response to glucose was also normal, and perhaps augmented (FIGS. 9A-9C). Further, harmine alone activated beta cell proliferation in T2D beta cells (FIGS. 9D-9E), an observation not previously reported. Finally, the harmine-GLP1 combination provided the same synergistic increase in Ki67 immunolabeling in T2D beta cells as observed in normal beta cells.

Figure 10A:
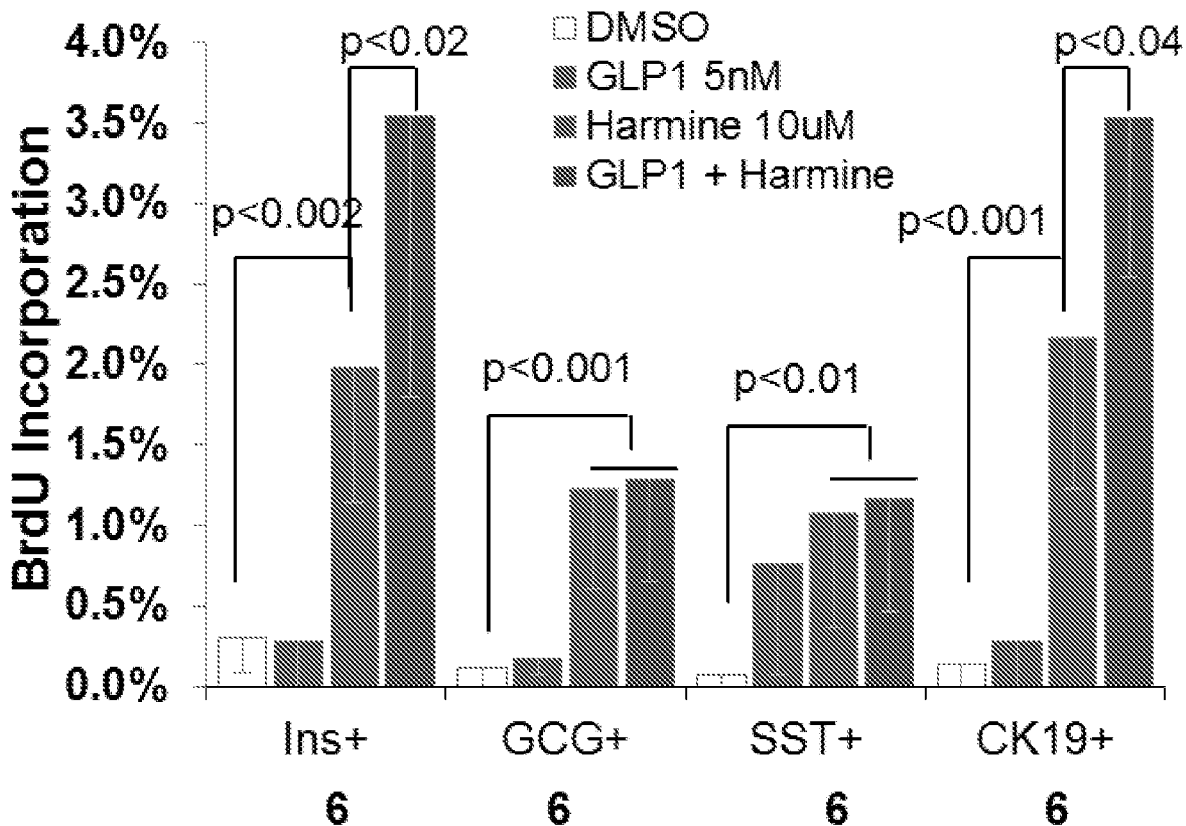
FIGS. 10A-10D show the effects of the harmine-GLP1 combination on proliferation in non-beta cells, and on beta cell death and DNA damage.
Figure 10B:
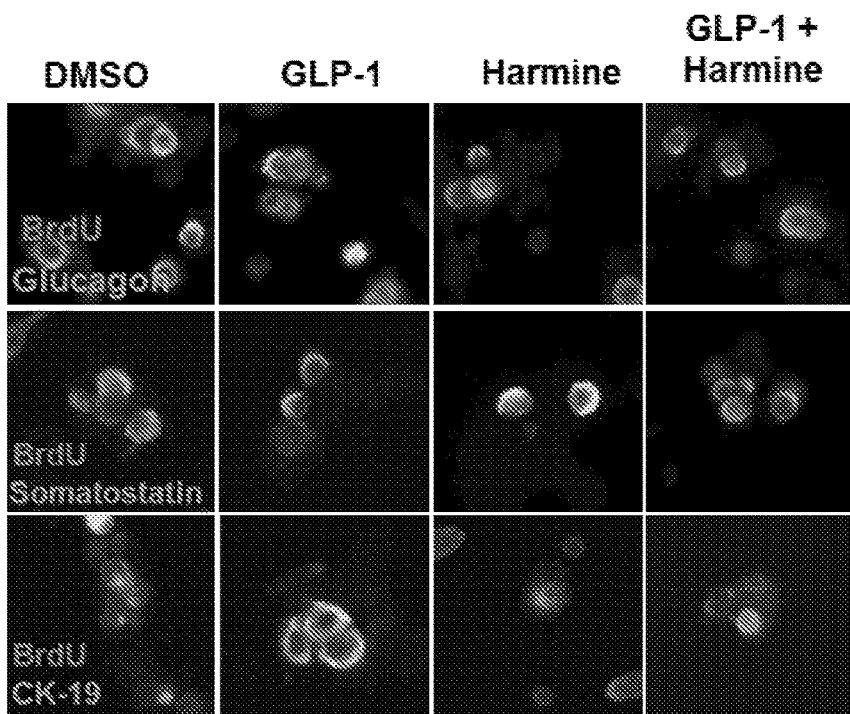
Figure 10C:
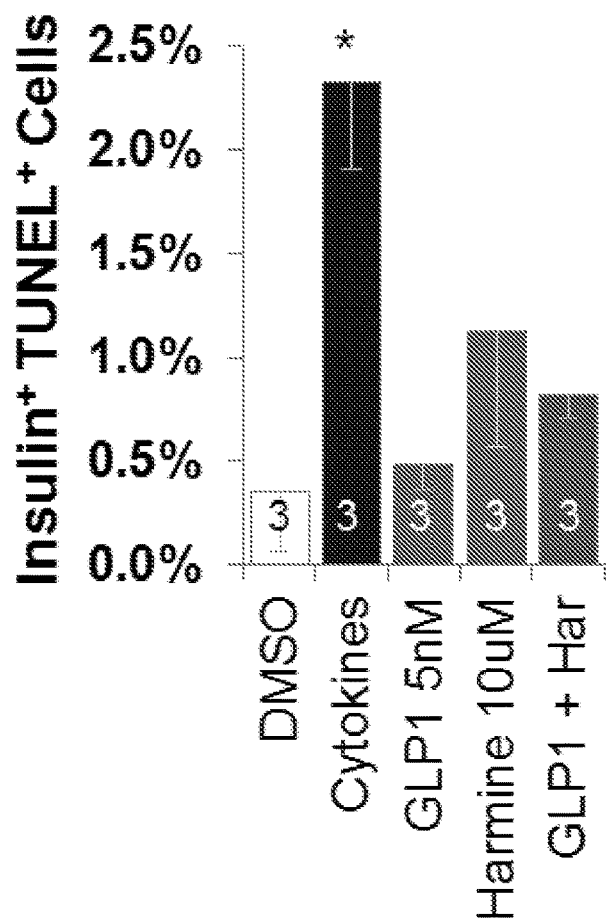
Figure 10D:
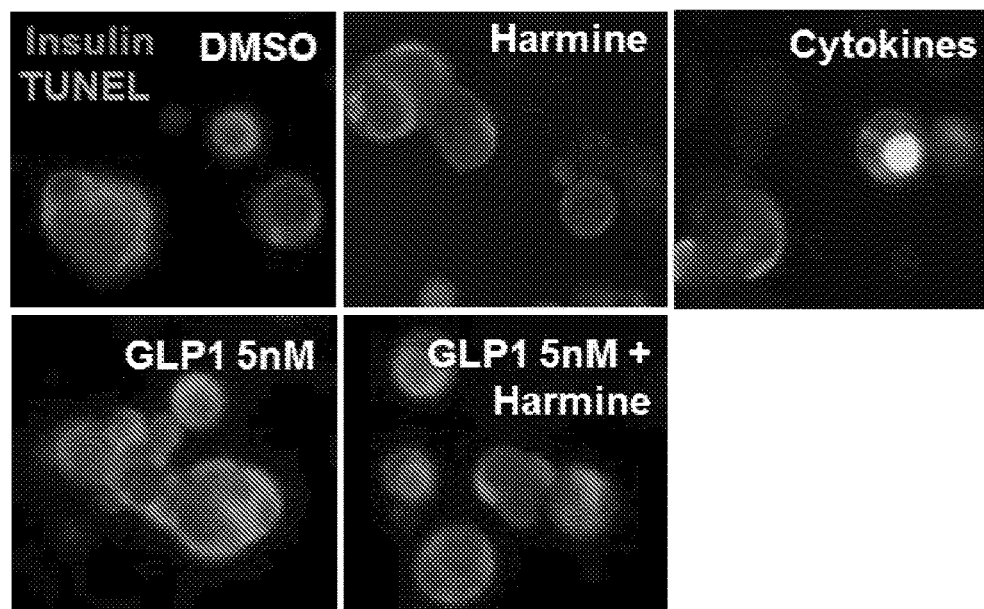

Example 6—Effects of the Harmine-GLP1 Combination on Human Islet Cells Other than Beta Cells Harmine has been reported to induce proliferation in islet cells other than the beta cells (Wang et al., "A High-Throughput Chemical Screen Reveals that Harmine-Mediated Inhibition of DYRK1A Increases Human Pancreatic Beta Cell Replication," *Nat. Med.* 21(4):383-388 (2015); Dirice et al., "Inhibition of DYRK1A Stimulates Human Beta Cell Proliferation," *Diabetes* 65(6):1660-1671 (2016); and Wang et al., "Singe Cell Mass Cytometry Analysis of Human Endocrine Pancreas," *Cell Metab.* 24(4):616-626 (2016), which are hereby incorporated by reference in their entirety), as shown in FIGS. 10A-10B. The addition of GLP1 to harmine further increased proliferation in ductal cells and as in beta cells, but had no additional effect on alpha or delta cells that produce glucagon and somatostatin, respectively, likely reflecting the absence of GLP1R on alpha and delta cells (Pyke et al., "GLP1 Receptor Localization in Monkey and Human Tissue: Novel Distribution Revealed With Extensively Validated Monoclonal Antibody," *Endocrinology* 155(4):1280-90 (2014) and Amisten et al., "An Atlas and Functional Analysis of G-Protein Coupled Receptors in Human Islets of Langerhans," *Pharmacol. Ther.* 139(3):359-391 (2013), which are hereby incorporated by reference in their entirety). Neither harmine nor the harmine-GLP1 combination treatment induced markers of beta cell death (TUNEL) (FIGS. 10C-10D).

Discussion of Examples 1-6

The Examples describe several notable observations. First, by combining any one of a large group of currently widely used diabetes drugs that directly (the GLP1 analogues) or indirectly (the DPP4 inhibitors) activate the GLP1R to an orally active, small molecule DYRK1A inhibitor (such as harmine, INDY, leucettine, 5-IT, GNF4877, or others), one is able to induce previously unattainable "rates," or more accurately, "labeling indices," of human beta cell replication. These rates exceed those of DYRK1A inhibitors alone, and are in the range one might envision as being necessary for restoration of normal beta cell mass in people with Type 2 diabetes and perhaps Type 1 diabetes. Second, the increase in human beta cell proliferation markers is accompanied by actual increases in numbers of adult human beta cells. Third, the increase in proliferation is synergistic in a rigorous pharmacological sense, and even extends to doses of harmine and GLP1 that have no proliferative effect on their own. Importantly, this may allow the addition of a low dose of a harmine analogue, which has no systemic effects on its own, to a standard long term drug regimen currently in widespread use in people with T2D, generating mitogenic effects specific to the beta cell. Fourth, harmine alone and in combination with a GLP1R agonist is able to induce both proliferation as well as differentiation in beta cells derived from people with T2D, a disease associated with both inadequate numbers as well as de-differentiation of beta cells. Finally, the Examples provided herein extend and validate a rapid, simple, and reliable FACS-based assay for counting human beta cell numbers.

The Examples also underscore remaining hurdles to therapeutic human beta cell regeneration. One is the need to protect newly generated beta cells in people with Type 1 diabetes from ongoing immune attack. This challenge remains unmet at present, but is not a barrier for the large group of people with Type 2 diabetes who also need beta cell expansion. A second is the need to develop tools to direct regenerative drugs and imaging agents specifically and exclusively to the human beta cell. The synergistic efficacy of a low dose of harmine (that has no effects on its own) with any dose of a GLP1R agonist raises the interesting possibility that the beta cell specificity of the GLP1 receptor may be leveraged for human beta cell proliferation by using low dose harmine in subjects already using GLP1 receptor agonists.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of increasing cell proliferation in a population of human pancreatic beta cells, said method comprising:

contacting a population of human pancreatic beta cells with a dual-specificity tyrosine phosphorylation-regulated kinase 1A (DYRK1A) inhibitor and a glucagon-like peptide-1 receptor (GLP1R) agonist, wherein said contacting is carried out under conditions effective to cause a synergistic increase in cell proliferation in the population of human pancreatic beta cells.

2. The method according to claim 1, wherein said method is carried out ex vivo.

3. The method according to claim 1, wherein said method is carried out in vivo.

4. The method according to claim 1, wherein said contacting is carried out with a composition comprising both the DYRK1A inhibitor and the GLP1R agonist.

5. The method according to claim 1, wherein said contacting increases the number of proliferating pancreatic beta cells in the population by about 4-6% per day.

6. The method according to claim 1, wherein said contacting increases the number of proliferating pancreatic beta cells in the population by about 6-10% per day.

7. The method according to claim 1, wherein the DYRK1A inhibitor is selected from the group consisting of harmine; INDY, having the chemical structure

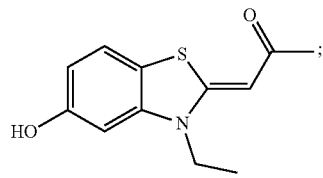 [SMILES: CCN1/C(=C/C(C)=O)Sc2ccc(O)cc21]

leucettine-41, having the chemical structure

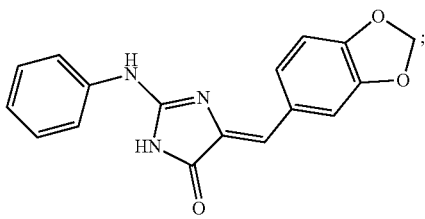 [SMILES: O=C1NC(Nc2ccccc2)=N/C1=C\c1ccc2c(c1)OCO2]

5-iodotubercidin (5-IT), having the chemical structure

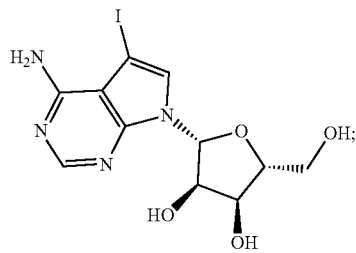 [SMILES: Nc1ncnc2c1c(I)cn2[C@@H]1O[C@H](CO)[C@@H](O)[C@H]1O]

GNF4877, having the chemical structure

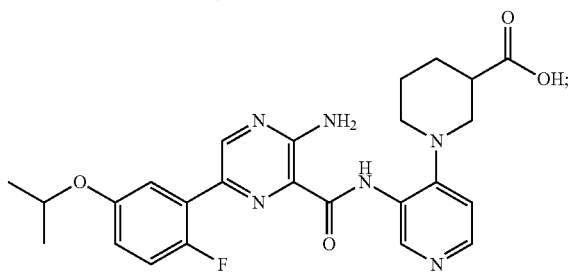 [SMILES: CC(C)Oc1ccc(F)c(-c2cnc(N)c(C(=O)Nc3cnccc3N3CCCC(C(=O)O)C3)n2)c1]

CC-401, having the chemical structure

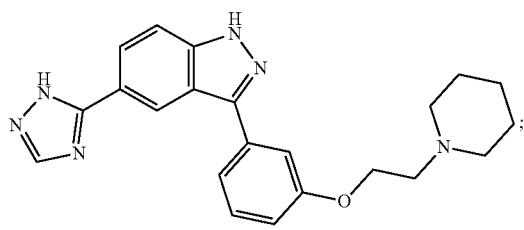 [SMILES: c1cc(OCCN2CCCCC2)cc(-c2n[nH]c3ccc(-c4ncn[nH]4)cc23)c1]

thiadiazine kinase inhibitors; and combinations thereof.

8. The method according to claim 1, wherein the GLP1R agonist is selected from the group consisting of GLP1 analogs, extendin-4, liraglutide, lixisenatide, semaglutide, and combinations thereof.

9. The method according to claim 1, wherein said contacting is carried out with harmine and GLP1(7-36).

10. The method according to claim 1, wherein said pancreatic beta cells are primary human pancreatic beta cells.

11. The method according to claim 1, wherein said contacting does not induce beta cell death or DNA damage.

12. The method according to claim 1, wherein said contacting induces beta cell differentiation.

13. The method according to claim 1, wherein said contacting increases glucose-stimulated insulin secretion.

* * * * *

SEQUENCE LISTING

<160> NUMBER OF SEQ ID NOS: 82

<210> SEQ ID NO 1
<211> LENGTH: 20
<212> TYPE: DNA
<213> ORGANISM: Artificial Sequence
<220> FEATURE:
<223> OTHER INFORMATION: CCNA1 (Cyclin A1) Primer

<400> SEQUENCE: 1
gaggtcccga tgcttgtcag                                               20

<210> SEQ ID NO 2
<211> LENGTH: 23
<212> TYPE: DNA
<213> ORGANISM: Artificial Sequence
<220> FEATURE:
<223> OTHER INFORMATION: CCNA2 (Cyclin A2) Primer

<400> SEQUENCE: 2
ggatggtagt tttgagtcac cac                                           23

<210> SEQ ID NO 3
<211> LENGTH: 23
<212> TYPE: DNA
<213> ORGANISM: Artificial Sequence
<220> FEATURE:
<223> OTHER INFORMATION: CCNB1 (Cyclin B1) Primer

<400> SEQUENCE: 3
aataaggcga agatcaacat ggc                                           23

<210> SEQ ID NO 4
<211> LENGTH: 21
<212> TYPE: DNA
<213> ORGANISM: Artificial Sequence
<220> FEATURE:
<223> OTHER INFORMATION: CCNB2 (Cyclin B2) Primer

<400> SEQUENCE: 4
ttggctggta caagtccact c                                             21

<210> SEQ ID NO 5
<211> LENGTH: 22
<212> TYPE: DNA
<213> ORGANISM: Artificial Sequence
<220> FEATURE:
<223> OTHER INFORMATION: CCNB3 (Cyclin B3) Primer

<400> SEQUENCE: 5
atgaaggcag tatgcaagaa gg                                            22

<210> SEQ ID NO 6
<211> LENGTH: 20
<212> TYPE: DNA
<213> ORGANISM: Artificial Sequence
<220> FEATURE:
<223> OTHER INFORMATION: CCND1 (Cyclin D1) Primer

<400> SEQUENCE: 6
caatgacccc gcacgatttc                                               20

<210> SEQ ID NO 7
<211> LENGTH: 20
<212> TYPE: DNA
<213> ORGANISM: Artificial Sequence

```
<220> FEATURE:
<223> OTHER INFORMATION: CCND2 (Cyclin D2) Primer

<400> SEQUENCE: 7
tttgccatgt acccaccgtc                                              20

<210> SEQ ID NO 8
<211> LENGTH: 19
<212> TYPE: DNA
<213> ORGANISM: Artificial Sequence
<220> FEATURE:
<223> OTHER INFORMATION: CCND3 (Cyclin D3) Primer

<400> SEQUENCE: 8
tacccgccat ccatgatcg                                               19

<210> SEQ ID NO 9
<211> LENGTH: 19
<212> TYPE: DNA
<213> ORGANISM: Artificial Sequence
<220> FEATURE:
<223> OTHER INFORMATION: CCNE1 (Cyclin E1) Primer

<400> SEQUENCE: 9
actcaacgtg caagcctcg                                               19

<210> SEQ ID NO 10
<211> LENGTH: 22
<212> TYPE: DNA
<213> ORGANISM: Artificial Sequence
<220> FEATURE:
<223> OTHER INFORMATION: CCNE2 (Cyclin E2) Primer

<400> SEQUENCE: 10
tcaagacgaa gtagccgttt ac                                           22

<210> SEQ ID NO 11
<211> LENGTH: 22
<212> TYPE: DNA
<213> ORGANISM: Artificial Sequence
<220> FEATURE:
<223> OTHER INFORMATION: CDC2 (CDK1) Primer

<400> SEQUENCE: 11
ggatgtgctt atgcaggatt cc                                           22

<210> SEQ ID NO 12
<211> LENGTH: 21
<212> TYPE: DNA
<213> ORGANISM: Artificial Sequence
<220> FEATURE:
<223> OTHER INFORMATION: CDK2 Primer

<400> SEQUENCE: 12
gtacctcccc tggatgaaga t                                            21

<210> SEQ ID NO 13
<211> LENGTH: 20
<212> TYPE: DNA
<213> ORGANISM: Artificial Sequence
<220> FEATURE:
<223> OTHER INFORMATION: CDK4 Primer

<400> SEQUENCE: 13
tcagcacagt tcgtgaggtg                                              20
```

```
<210> SEQ ID NO 14
<211> LENGTH: 21
<212> TYPE: DNA
<213> ORGANISM: Artificial Sequence
<220> FEATURE:
<223> OTHER INFORMATION: CDK6 Primer

<400> SEQUENCE: 14
ccagatggct ctaacctcag t                                             21

<210> SEQ ID NO 15
<211> LENGTH: 19
<212> TYPE: DNA
<213> ORGANISM: Artificial Sequence
<220> FEATURE:
<223> OTHER INFORMATION: CDC25A Primer

<400> SEQUENCE: 15
gtgaaggcgc tatttggcg                                                19

<210> SEQ ID NO 16
<211> LENGTH: 22
<212> TYPE: DNA
<213> ORGANISM: Artificial Sequence
<220> FEATURE:
<223> OTHER INFORMATION: CDKN1A (p21) Primer

<400> SEQUENCE: 16
cgatggaact tcgactttgt ca                                            22

<210> SEQ ID NO 17
<211> LENGTH: 21
<212> TYPE: DNA
<213> ORGANISM: Artificial Sequence
<220> FEATURE:
<223> OTHER INFORMATION: CDKN1B (p27) Primer

<400> SEQUENCE: 17
taattggggc tccggctaac t                                             21

<210> SEQ ID NO 18
<211> LENGTH: 19
<212> TYPE: DNA
<213> ORGANISM: Artificial Sequence
<220> FEATURE:
<223> OTHER INFORMATION: CDKN1C (p57) Primer

<400> SEQUENCE: 18
gcggcgatca agaagctgt                                                19

<210> SEQ ID NO 19
<211> LENGTH: 19
<212> TYPE: DNA
<213> ORGANISM: Artificial Sequence
<220> FEATURE:
<223> OTHER INFORMATION: CDKN2A (p16) Primer

<400> SEQUENCE: 19
atggagcctt cggctgact                                                19

<210> SEQ ID NO 20
<211> LENGTH: 20
<212> TYPE: DNA
<213> ORGANISM: Artificial Sequence
<220> FEATURE:
<223> OTHER INFORMATION: CDKN2B (p15) Primer
```

```
<400> SEQUENCE: 20
cgttaagttt acggccaacg                                                    20

<210> SEQ ID NO 21
<211> LENGTH: 23
<212> TYPE: DNA
<213> ORGANISM: Artificial Sequence
<220> FEATURE:
<223> OTHER INFORMATION: CDKN2C (p18) Primer

<400> SEQUENCE: 21
aaacttggaa atcccgagat tgc                                                23

<210> SEQ ID NO 22
<211> LENGTH: 19
<212> TYPE: DNA
<213> ORGANISM: Artificial Sequence
<220> FEATURE:
<223> OTHER INFORMATION: CDKN2D (p19) Primer

<400> SEQUENCE: 22
agtccagtcc atgacgcag                                                     19

<210> SEQ ID NO 23
<211> LENGTH: 21
<212> TYPE: DNA
<213> ORGANISM: Artificial Sequence
<220> FEATURE:
<223> OTHER INFORMATION: c-MYC Primer

<400> SEQUENCE: 23
ccacacatca gcacaactac g                                                  21

<210> SEQ ID NO 24
<211> LENGTH: 20
<212> TYPE: DNA
<213> ORGANISM: Artificial Sequence
<220> FEATURE:
<223> OTHER INFORMATION: Cyclophilin A Primer

<400> SEQUENCE: 24
caccgtgttc ttcgacattg                                                    20

<210> SEQ ID NO 25
<211> LENGTH: 21
<212> TYPE: DNA
<213> ORGANISM: Artificial Sequence
<220> FEATURE:
<223> OTHER INFORMATION: FOXM1 Primer

<400> SEQUENCE: 25
atacgtggat tgaggaccac t                                                  21

<210> SEQ ID NO 26
<211> LENGTH: 21
<212> TYPE: DNA
<213> ORGANISM: Artificial Sequence
<220> FEATURE:
<223> OTHER INFORMATION: DYRKIA Primer

<400> SEQUENCE: 26
gccagggaga cgattctagt c                                                  21

<210> SEQ ID NO 27
```

<211> LENGTH: 21
<212> TYPE: DNA
<213> ORGANISM: Artificial Sequence
<220> FEATURE:
<223> OTHER INFORMATION: GLP1R Primer

<400> SEQUENCE: 27
ggtgcagaaa tggcgagaat a         21

<210> SEQ ID NO 28
<211> LENGTH: 23
<212> TYPE: DNA
<213> ORGANISM: Artificial Sequence
<220> FEATURE:
<223> OTHER INFORMATION: INS Primer

<400> SEQUENCE: 28
tcacacctgg tggaagctct cta        23

<210> SEQ ID NO 29
<211> LENGTH: 22
<212> TYPE: DNA
<213> ORGANISM: Artificial Sequence
<220> FEATURE:
<223> OTHER INFORMATION: ISL1 Primer

<400> SEQUENCE: 29
aggagcaact ggtagagatg ac         22

<210> SEQ ID NO 30
<211> LENGTH: 19
<212> TYPE: DNA
<213> ORGANISM: Artificial Sequence
<220> FEATURE:
<223> OTHER INFORMATION: MAFA Primer

<400> SEQUENCE: 30
gagcggctac cagcatcac            19

<210> SEQ ID NO 31
<211> LENGTH: 21
<212> TYPE: DNA
<213> ORGANISM: Artificial Sequence
<220> FEATURE:
<223> OTHER INFORMATION: MAFB Primer

<400> SEQUENCE: 31
tcaagttcga cgtgaagaag g          21

<210> SEQ ID NO 32
<211> LENGTH: 21
<212> TYPE: DNA
<213> ORGANISM: Artificial Sequence
<220> FEATURE:
<223> OTHER INFORMATION: NeuroD1 Primer

<400> SEQUENCE: 32
gtctccttcg ttcagacgct t          21

<210> SEQ ID NO 33
<211> LENGTH: 21
<212> TYPE: DNA
<213> ORGANISM: Artificial Sequence
<220> FEATURE:
<223> OTHER INFORMATION: NGN3 Primer

<400> SEQUENCE: 33
ctaagagcga gttggcactg a									21

<210> SEQ ID NO 34
<211> LENGTH: 21
<212> TYPE: DNA
<213> ORGANISM: Artificial Sequence
<220> FEATURE:
<223> OTHER INFORMATION: NKX6.1 Primer

<400> SEQUENCE: 34
acacgagacc cacttttcc g									21

<210> SEQ ID NO 35
<211> LENGTH: 19
<212> TYPE: DNA
<213> ORGANISM: Artificial Sequence
<220> FEATURE:
<223> OTHER INFORMATION: PAX4 Primer

<400> SEQUENCE: 35
agtcctgcgg gcattacag									19

<210> SEQ ID NO 36
<211> LENGTH: 20
<212> TYPE: DNA
<213> ORGANISM: Artificial Sequence
<220> FEATURE:
<223> OTHER INFORMATION: PCSK1 Primer

<400> SEQUENCE: 36
ggacctctga gtatgacccg									20

<210> SEQ ID NO 37
<211> LENGTH: 22
<212> TYPE: DNA
<213> ORGANISM: Artificial Sequence
<220> FEATURE:
<223> OTHER INFORMATION: PCSK2 Primer

<400> SEQUENCE: 37
gggaaaggtg ttaccattgg aa									22

<210> SEQ ID NO 38
<211> LENGTH: 22
<212> TYPE: DNA
<213> ORGANISM: Artificial Sequence
<220> FEATURE:
<223> OTHER INFORMATION: PDX1 Primer

<400> SEQUENCE: 38
tgatgtgtct ctcggtcaag tt									22

<210> SEQ ID NO 39
<211> LENGTH: 20
<212> TYPE: DNA
<213> ORGANISM: Artificial Sequence
<220> FEATURE:
<223> OTHER INFORMATION: ARX Primer

<400> SEQUENCE: 39
ctgctgaaac gcaaacagag									20

<210> SEQ ID NO 40
<211> LENGTH: 21
<212> TYPE: DNA

```
<213> ORGANISM: Artificial Sequence
<220> FEATURE:
<223> OTHER INFORMATION: SLC2A1 (GLUT1) Primer

<400> SEQUENCE: 40
ggccaagagt gtgctaaaga a                                              21

<210> SEQ ID NO 41
<211> LENGTH: 22
<212> TYPE: DNA
<213> ORGANISM: Artificial Sequence
<220> FEATURE:
<223> OTHER INFORMATION: SLC2A2 (GLUT2) Primer

<400> SEQUENCE: 41
gctgctcaac taatcaccat gc                                             22

<210> SEQ ID NO 42
<211> LENGTH: 21
<212> TYPE: DNA
<213> ORGANISM: Artificial Sequence
<220> FEATURE:
<223> OTHER INFORMATION: CCNA1 (Cyclin A1) Primer

<400> SEQUENCE: 42
gttagcagcc ctagcactgt c                                              21

<210> SEQ ID NO 43
<211> LENGTH: 23
<212> TYPE: DNA
<213> ORGANISM: Artificial Sequence
<220> FEATURE:
<223> OTHER INFORMATION: CCNA2 (Cyclin A2)

<400> SEQUENCE: 43
cacgaggata gctctcatac tgt                                            23

<210> SEQ ID NO 44
<211> LENGTH: 23
<212> TYPE: DNA
<213> ORGANISM: Artificial Sequence
<220> FEATURE:
<223> OTHER INFORMATION: CCNB1 (Cyclin B1) Primer

<400> SEQUENCE: 44
tttgttacca atgtccccaa gag                                            23

<210> SEQ ID NO 45
<211> LENGTH: 23
<212> TYPE: DNA
<213> ORGANISM: Artificial Sequence
<220> FEATURE:
<223> OTHER INFORMATION: CCNB2 (Cyclin B2)

<400> SEQUENCE: 45
tgggaactgg tataagcatt gtc                                            23

<210> SEQ ID NO 46
<211> LENGTH: 21
<212> TYPE: DNA
<213> ORGANISM: Artificial Sequence
<220> FEATURE:
<223> OTHER INFORMATION: CCNB3 (Cyclin B3) Primer

<400> SEQUENCE: 46
catccacacg aggtgagttg t                                              21
```

<210> SEQ ID NO 47
<211> LENGTH: 19
<212> TYPE: DNA
<213> ORGANISM: Artificial Sequence
<220> FEATURE:
<223> OTHER INFORMATION: CCND1 (Cyclin D1) Primer

<400> SEQUENCE: 47
catggagggc ggattggaa                                              19

<210> SEQ ID NO 48
<211> LENGTH: 19
<212> TYPE: DNA
<213> ORGANISM: Artificial Sequence
<220> FEATURE:
<223> OTHER INFORMATION: CCND2 (Cyclin D2) Primer

<400> SEQUENCE: 48
agggcatcac aagtgagcg                                              19

<210> SEQ ID NO 49
<211> LENGTH: 19
<212> TYPE: DNA
<213> ORGANISM: Artificial Sequence
<220> FEATURE:
<223> OTHER INFORMATION: CCND3 (Cyclin D3) Primer

<400> SEQUENCE: 49
aggcagtcca cttcagtgc                                              19

<210> SEQ ID NO 50
<211> LENGTH: 21
<212> TYPE: DNA
<213> ORGANISM: Artificial Sequence
<220> FEATURE:
<223> OTHER INFORMATION: CCNE1 (Cyclin E1) Primer

<400> SEQUENCE: 50
gctcaagaaa gtgctgatcc c                                           21

<210> SEQ ID NO 51
<211> LENGTH: 23
<212> TYPE: DNA
<213> ORGANISM: Artificial Sequence
<220> FEATURE:
<223> OTHER INFORMATION: CCNE2 (Cyclin E2) Primer

<400> SEQUENCE: 51
tgacatcctg ggtagttttc ctc                                         23

<210> SEQ ID NO 52
<211> LENGTH: 23
<212> TYPE: DNA
<213> ORGANISM: Artificial Sequence
<220> FEATURE:
<223> OTHER INFORMATION: CDC2 (CDK1) Primer

<400> SEQUENCE: 52
catgtactga ccaggaggga tag                                         23

<210> SEQ ID NO 53
<211> LENGTH: 21
<212> TYPE: DNA
<213> ORGANISM: Artificial Sequence
<220> FEATURE:

<223> OTHER INFORMATION: CDK2 Primer

<400> SEQUENCE: 53
cgaaatccgc ttgttagggt c                                              21

<210> SEQ ID NO 54
<211> LENGTH: 20
<212> TYPE: DNA
<213> ORGANISM: Artificial Sequence
<220> FEATURE:
<223> OTHER INFORMATION: CDK4 Primer

<400> SEQUENCE: 54
gtccatcagc cggacaacat                                                20

<210> SEQ ID NO 55
<211> LENGTH: 22
<212> TYPE: DNA
<213> ORGANISM: Artificial Sequence
<220> FEATURE:
<223> OTHER INFORMATION: CDK6 Primer

<400> SEQUENCE: 55
aacttccacg aaaaagaggc tt                                             22

<210> SEQ ID NO 56
<211> LENGTH: 21
<212> TYPE: DNA
<213> ORGANISM: Artificial Sequence
<220> FEATURE:
<223> OTHER INFORMATION: CDC25A Primer

<400> SEQUENCE: 56
tggttgctca taatcactgc c                                              21

<210> SEQ ID NO 57
<211> LENGTH: 21
<212> TYPE: DNA
<213> ORGANISM: Artificial Sequence
<220> FEATURE:
<223> OTHER INFORMATION: CDKN1A (p21) Primer

<400> SEQUENCE: 57
gcacaagggt acaagacagt g                                              21

<210> SEQ ID NO 58
<211> LENGTH: 21
<212> TYPE: DNA
<213> ORGANISM: Artificial Sequence
<220> FEATURE:
<223> OTHER INFORMATION: CDKN1B (p27) Primer

<400> SEQUENCE: 58
tgcaggtcgc ttccttattc c                                              21

<210> SEQ ID NO 59
<211> LENGTH: 21
<212> TYPE: DNA
<213> ORGANISM: Artificial Sequence
<220> FEATURE:
<223> OTHER INFORMATION: CDKN1C (p57) Primer

<400> SEQUENCE: 59
gcttggcgaa gaaatcggag a                                              21

```
<210> SEQ ID NO 60
<211> LENGTH: 21
<212> TYPE: DNA
<213> ORGANISM: Artificial Sequence
<220> FEATURE:
<223> OTHER INFORMATION: CDKN2A (p16) Primer

<400> SEQUENCE: 60
gtaactattc ggtgcgttgg g                                        21

<210> SEQ ID NO 61
<211> LENGTH: 19
<212> TYPE: DNA
<213> ORGANISM: Artificial Sequence
<220> FEATURE:
<223> OTHER INFORMATION: CDKN2B (p15) Primer

<400> SEQUENCE: 61
ggtgagagtg gcagggtct                                           19

<210> SEQ ID NO 62
<211> LENGTH: 22
<212> TYPE: DNA
<213> ORGANISM: Artificial Sequence
<220> FEATURE:
<223> OTHER INFORMATION: CDKN2C (p18) Primer

<400> SEQUENCE: 62
cgaaaccagt tcggtctttc aa                                       22

<210> SEQ ID NO 63
<211> LENGTH: 21
<212> TYPE: DNA
<213> ORGANISM: Artificial Sequence
<220> FEATURE:
<223> OTHER INFORMATION: CDKN2D (p19) primer

<400> SEQUENCE: 63
atcaggcacg ttgacatcag c                                        21

<210> SEQ ID NO 64
<211> LENGTH: 21
<212> TYPE: DNA
<213> ORGANISM: Artificial Sequence
<220> FEATURE:
<223> OTHER INFORMATION: c-MYC Primer

<400> SEQUENCE: 64
cagcaggata gtccttccga g                                        21

<210> SEQ ID NO 65
<211> LENGTH: 20
<212> TYPE: DNA
<213> ORGANISM: Artificial Sequence
<220> FEATURE:
<223> OTHER INFORMATION: Cyclophilin A Primer

<400> SEQUENCE: 65
tgaagtcacc accctgacac                                          20

<210> SEQ ID NO 66
<211> LENGTH: 21
<212> TYPE: DNA
<213> ORGANISM: Artificial Sequence
<220> FEATURE:
<223> OTHER INFORMATION: FOXM1 Primer
```

<400> SEQUENCE: 66
tccaatgtca agtagcggtt g                                              21

<210> SEQ ID NO 67
<211> LENGTH: 20
<212> TYPE: DNA
<213> ORGANISM: Artificial Sequence
<220> FEATURE:
<223> OTHER INFORMATION: DYRK1A Primer

<400> SEQUENCE: 67
aacccattct tgctccacac                                                20

<210> SEQ ID NO 68
<211> LENGTH: 21
<212> TYPE: DNA
<213> ORGANISM: Artificial Sequence
<220> FEATURE:
<223> OTHER INFORMATION: GLP1R Primer

<400> SEQUENCE: 68
ccggttgcag aacaagtctg t                                              21

<210> SEQ ID NO 69
<211> LENGTH: 24
<212> TYPE: DNA
<213> ORGANISM: Artificial Sequence
<220> FEATURE:
<223> OTHER INFORMATION: INS Primer

<400> SEQUENCE: 69
acaatgccac gcttctgcag ggac                                           24

<210> SEQ ID NO 70
<211> LENGTH: 21
<212> TYPE: DNA
<213> ORGANISM: Artificial Sequence
<220> FEATURE:
<223> OTHER INFORMATION: ISLI Primer

<400> SEQUENCE: 70
gtccttgcac cgcttgtttt g                                              21

<210> SEQ ID NO 71
<211> LENGTH: 21
<212> TYPE: DNA
<213> ORGANISM: Artificial Sequence
<220> FEATURE:
<223> OTHER INFORMATION: MAFA Primer

<400> SEQUENCE: 71
ctctggagtt ggcacttctc g                                              21

<210> SEQ ID NO 72
<211> LENGTH: 21
<212> TYPE: DNA
<213> ORGANISM: Artificial Sequence
<220> FEATURE:
<223> OTHER INFORMATION: MAFB Primer

<400> SEQUENCE: 72
gttcatctgc tggtagttgc t                                              21

<210> SEQ ID NO 73
<211> LENGTH: 21

```
<212> TYPE: DNA
<213> ORGANISM: Artificial Sequence
<220> FEATURE:
<223> OTHER INFORMATION: NeuroD1 Primer

<400> SEQUENCE: 73
aaagtccgag gattgagttg c                                          21

<210> SEQ ID NO 74
<211> LENGTH: 21
<212> TYPE: DNA
<213> ORGANISM: Artificial Sequence
<220> FEATURE:
<223> OTHER INFORMATION: NGN3 Primer

<400> SEQUENCE: 74
gaggttgtgc attcgattgc g                                          21

<210> SEQ ID NO 75
<211> LENGTH: 23
<212> TYPE: DNA
<213> ORGANISM: Artificial Sequence
<220> FEATURE:
<223> OTHER INFORMATION: NKX6.1 Primer

<400> SEQUENCE: 75
tgctggactt gtgcttcttc aac                                        23

<210> SEQ ID NO 76
<211> LENGTH: 22
<212> TYPE: DNA
<213> ORGANISM: Artificial Sequence
<220> FEATURE:
<223> OTHER INFORMATION: PAX4 Primer

<400> SEQUENCE: 76
gggagaagat agtccgattc cg                                         22

<210> SEQ ID NO 77
<211> LENGTH: 21
<212> TYPE: DNA
<213> ORGANISM: Artificial Sequence
<220> FEATURE:
<223> OTHER INFORMATION: PCSK1 Primer

<400> SEQUENCE: 77
agctttggca tttagcaagc c                                          21

<210> SEQ ID NO 78
<211> LENGTH: 21
<212> TYPE: DNA
<213> ORGANISM: Artificial Sequence
<220> FEATURE:
<223> OTHER INFORMATION: PCSK2 Primer

<400> SEQUENCE: 78
ccagtcatct gtgtaccgag g                                          21

<210> SEQ ID NO 79
<211> LENGTH: 21
<212> TYPE: DNA
<213> ORGANISM: Artificial Sequence
<220> FEATURE:
<223> OTHER INFORMATION: PDX1 Primer

<400> SEQUENCE: 79
```

```
accaaagctc acgcgtggaa a                                          21

<210> SEQ ID NO 80
<211> LENGTH: 21
<212> TYPE: DNA
<213> ORGANISM: Artificial Sequence
<220> FEATURE:
<223> OTHER INFORMATION: ARX Primer

<400> SEQUENCE: 80
cgacggttct ggaaccagac c                                          21

<210> SEQ ID NO 81
<211> LENGTH: 20
<212> TYPE: DNA
<213> ORGANISM: Artificial Sequence
<220> FEATURE:
<223> OTHER INFORMATION: SLC2A1 (GLUT1) Primer

<400> SEQUENCE: 81
acagcgttga tgccagacag                                            20

<210> SEQ ID NO 82
<211> LENGTH: 22
<212> TYPE: DNA
<213> ORGANISM: Artificial Sequence
<220> FEATURE:
<223> OTHER INFORMATION: SLC2A2 (GLUT2) Primer

<400> SEQUENCE: 82
tggtcccaat tttgaaaacc cc                                         22
```